(12) United States Patent
Greaves et al.

(10) Patent No.: US 7,300,471 B2
(45) Date of Patent: *Nov. 27, 2007

(54) COMPOSITION COMPRISING AT LEAST ONE MIXED DYE BASED ON AT LEAST ONE CHROMOPHORE OF AZO OR TRI(HETERO) ARYLMETHANE TYPE, DYEING PROCESS AND MIXED DYES.

(75) Inventors: Andrew Greaves, Montevrain (FR); Hervé David, Joinville le Pont (FR); Henri Samain, Bievres (FR)

(73) Assignee: L'Oreal S.A. (FR)

( * ) Notice: Subject to any disclaimer, the term of this patent is extended or adjusted under 35 U.S.C. 154(b) by 335 days.

This patent is subject to a terminal disclaimer.

(21) Appl. No.: 11/066,459

(22) Filed: Feb. 28, 2005

(65) Prior Publication Data

US 2005/0241074 A1    Nov. 3, 2005

Related U.S. Application Data

(60) Provisional application No. 60/568,270, filed on May 6, 2004.

(30) Foreign Application Priority Data

Feb. 27, 2004 (FR) .................................. 04 50380

(51) Int. Cl.
  A61K 7/13    (2006.01)
(52) U.S. Cl. ...................... 8/405; 8/406; 8/407; 8/410; 8/411; 8/423; 8/426; 8/437; 8/565; 8/566; 8/567; 8/568; 8/570; 8/573; 8/574; 8/608; 534/269.4; 548/301.7
(58) Field of Classification Search .................... 8/405, 8/406, 407, 410, 411, 423, 426, 437, 565, 8/566, 567, 568, 570, 573, 574, 608; 534/269.4; 548/301.7
See application file for complete search history.

(56) References Cited

U.S. PATENT DOCUMENTS

| | | |
|---|---|---|
| 3,100,739 A | 8/1963 | Kaiser et al. |
| 3,423,427 A | 1/1969 | Anthony et al. |
| 3,524,842 A | 8/1970 | Grossmann et al. |
| 3,578,386 A | 5/1971 | Kaliopissis et al. |
| 3,617,163 A | 11/1971 | Kalopissis et al. |
| 3,652,556 A | 3/1972 | Kühlthau et al. |
| 3,817,698 A | 6/1974 | Kalopissis et al. |
| 3,867,456 A | 2/1975 | Kalopissis et al. |
| 3,955,918 A | 5/1976 | Lang |
| 3,985,499 A | 10/1976 | Lang et al. |
| 3,995,088 A | 11/1976 | Garner et al. |
| 4,025,301 A | 5/1977 | Lang |
| 4,054,718 A | 10/1977 | Garner et al. |
| 4,151,162 A | 4/1979 | Lang et al. |
| 4,153,065 A | 5/1979 | Lang |
| 4,226,784 A | 10/1980 | Kalopissis et al. |
| 4,661,115 A | 4/1987 | Orth et al. |
| 4,670,385 A | 6/1987 | Babb et al. |
| 4,823,985 A | 4/1989 | Grollier et al. |
| 4,886,517 A | 12/1989 | Bugaut et al. |
| 5,094,688 A | 3/1992 | Eckstein et al. |
| 5,097,034 A | 3/1992 | Eckstein |
| 5,122,605 A | 6/1992 | Pedrazzi |
| 5,708,151 A * | 1/1998 | Mockli ....................... 534/608 |
| 5,821,347 A | 10/1998 | Dannheim |
| 5,879,413 A | 3/1999 | Pengilly et al. |
| 5,919,273 A | 7/1999 | Rondeau et al. |
| 5,980,587 A | 11/1999 | Samain |
| 5,993,490 A | 11/1999 | Rondeau et al. |
| 6,045,591 A | 4/2000 | Deneulenacre |
| 6,136,042 A | 10/2000 | Maubru |
| 6,179,881 B1 | 1/2001 | Henrion et al. |
| 6,297,362 B1 | 10/2001 | Kunde et al. |
| 6,368,360 B2 | 4/2002 | Samain |
| 6,458,167 B1 | 10/2002 | Genet et al. |
| 6,468,316 B1 | 10/2002 | Genet et al. |
| 6,492,502 B2 | 12/2002 | Henrion et al. |
| 6,592,634 B1 | 7/2003 | Reichert et al. |
| 6,712,861 B2 | 3/2004 | Rondeau |
| 6,797,013 B1 | 9/2004 | Cotteret et al. |
| 6,863,883 B1 | 3/2005 | Tsujino et al. |
| 6,884,265 B2 | 4/2005 | Vidal et al. |
| 7,056,346 B1 | 6/2006 | Maubru |

(Continued)

FOREIGN PATENT DOCUMENTS

BE       702 239       2/1968

(Continued)

OTHER PUBLICATIONS

STIC Search Report dated Mar. 21, 2007.*
French Search Report for FR 0450380 (French priority application for the present application), dated Oct. 6, 2004.
English language abstract of DE 12 54 118, Nov. 16, 1967.
English language abstract of DE 25 27 638, May 6, 1976.
English language abstract of DE 33 35 956 A1, Apr. 18, 1985.
English language abstract of DE 41 37 005 A1, May 13, 1993.
English language abstract of DE 42 20 388 A1, Dec. 23, 1993.
English language abstract of JP 60-215882, Oct. 29, 1985.
English language abstract of JP 2002-47153, Feb. 12, 2002.
V.V. Stashkevich et al., "Bisformazans and Bistetrazolium Salts, Derivatives of Quaternary Salts of Quinaldine," Journal of General Chemistry of the USSR, Consultants Bureau, New York, vol. 40, No. 1, pp. 178-183, 1970.

(Continued)

*Primary Examiner*—Eisa Elhilo
(74) *Attorney, Agent, or Firm*—Finnegan, Henderson, Farabow, Garrett & Dunner LLP

(57) ABSTRACT

Disclosed herein are a dye composition comprising at least one mixed dye comprising at least one chromophore chosen from chromophores of the azo family and the tri(hetero) arylmethane family; and the mixed dyes. Further disclosed herein are a process for dyeing keratin fibers, such as human keratin fibers, using the composition, and a device comprising the composition.

42 Claims, No Drawings

U.S. PATENT DOCUMENTS

| | | |
|---|---|---|
| 7,172,633 B2 * | 2/2007 | Samain et al. ............... 8/405 |
| 2001/0001332 A1 | 5/2001 | Henrion et al. |
| 2001/0001333 A1 | 5/2001 | Samain |
| 2002/0004956 A1 | 1/2002 | Rondeau |
| 2002/0165368 A1 | 11/2002 | Henrion et al. |
| 2003/0000023 A9 | 1/2003 | Rondeau |
| 2003/0163879 A1 | 9/2003 | Brennan et al. |
| 2003/0233713 A1 | 12/2003 | Quinn et al. |
| 2004/0187225 A1 | 9/2004 | Vidal et al. |

FOREIGN PATENT DOCUMENTS

| | | |
|---|---|---|
| DE | 1 254 118 | 11/1967 |
| DE | 25 27 638 | 5/1976 |
| DE | 25 38 363 | 5/1976 |
| DE | 33 35 956 A1 | 4/1985 |
| DE | 41 37 005 A1 | 5/1993 |
| DE | 42 20 388 A1 | 12/1993 |
| DE | 198 45 640 A1 | 4/2000 |
| EP | 0 850 636 A1 | 7/1998 |
| EP | 0 850 637 A1 | 7/1998 |
| EP | 0 918 053 A1 | 5/1999 |
| EP | 0 920 856 A1 | 6/1999 |
| EP | 1 062 940 A1 | 12/2000 |
| EP | 1 133 976 A2 | 9/2001 |
| EP | 1 153 598 B1 | 11/2001 |
| EP | 1 175 893 A2 | 1/2002 |
| FR | 1 221 122 | 5/1960 |
| FR | 1 516 943 | 3/1968 |
| FR | 1 540 423 | 9/1968 |
| FR | 1 560 664 | 3/1969 |
| FR | 1 567 219 | 5/1969 |
| FR | 2 189 006 | 1/1974 |
| FR | 2 275 462 | 1/1976 |
| FR | 2 285 851 | 4/1976 |
| FR | 2 570 946 A1 | 4/1986 |
| FR | 2 586 913 A1 | 3/1987 |
| FR | 2 757 385 A1 | 6/1998 |
| FR | 2 788 433 A1 | 7/2000 |
| GB | 738 585 | 10/1955 |
| GB | 822 846 | 11/1959 |
| GB | 1 047 796 | 11/1966 |
| GB | 1 139 408 | 1/1969 |
| GB | 1 163 385 | 9/1969 |
| GB | 1 195 386 | 6/1970 |
| GB | 1 514 466 | 6/1978 |
| JP | 60-215882 | 10/1985 |
| JP | 61-218512 | 9/1986 |
| JP | 2-292370 | 12/1990 |
| JP | 10-502946 | 3/1998 |
| JP | 2000-505841 | 5/2000 |
| JP | 2000-204026 | 7/2000 |
| JP | 2000-281921 | 10/2000 |
| JP | 2001-316231 | 11/2001 |
| JP | 2002-37718 | 2/2002 |
| JP | 2002-47153 | 2/2002 |
| JP | 2003-300847 | 10/2003 |
| WO | WO 95/01772 | 1/1995 |
| WO | WO 95/15144 | 6/1995 |
| WO | WO 97/44004 | 11/1997 |
| WO | WO 99/48465 | 9/1999 |
| WO | WO 01/66646 A1 | 9/2001 |
| WO | WO 02/078596 A2 | 10/2002 |
| WO | WO 03/018021 A1 | 3/2003 |
| WO | WO 03/029359 A1 | 4/2003 |
| WO | WO 03/030909 A1 | 4/2003 |

OTHER PUBLICATIONS

Guido Alberti et al., "Cationic Dyes for Acrylic Fibres. V. Cationic Dyes Derived from Several Heterocyclic Amines with Two or More Heteroatoms," Annali di Chimica, vol. 65, pp. 305-314, 1975.

Alexandru T. Balaban et al., "Reactions of Pyrylium Salts with Nucleophiles, XX. Synthesis of 4-(n-pyridinium)-4'-dialkylaminoazobenzene and of 4-(4-dialkylaminophenylazo)-4'-(n-pyridinium)-biphenyl Derivatives," Revue Roumaine de Chmie, vol. 33, No. 4, pp. 377-383 (1988).

Richard Neidlein et al, "Synthese von substituierten Pyridiniumsalzen," Monatshefte für Chemie, vol. 106, pp. 643-648 (1975).

Von Alfred Kreutzberger et al., "Antikonvulsiva, IV, 2,4,6-Gemischtfunktionell substituierte 1,3,5-Triazine," Chemiker-Zeitung, vol. 111, pp. 241-245 (1987).

Von Eberhard Seidler et al., "Die Eignung verschiedener Ditetrazoliumsalze als Reduktionsindikatoren in der Enzymhistochemie," Acta Histochem. Bd., vol. 61, pp. 48-52 (1978).

A.F. Kuzentsova et al., "The Determination of Thickness of a Histological Section by Interference Microscopy," Tsitologiya, vol. 10, No. 3, pp. 403-405 (1968).

G. Alberti, "Ricerche Sui Coloranti Cationici Per Fibra Agrilica," La Chimica E L'Industria, vol. 56, No. 9, pp. 600-602 (1974).

V. V. Stashkevich et al., "Bisformazans and Bistetrazolium Salts, Derivatives of quaternary Salts of Quinaldine," Journal of General Chemistry of the USSR, vol. 40, No. 1, pp. 178-183 (1970).

Hsien-Ju Tien et al., "Synthesis of New Azo Dyestuff Containing a Sydnone Ring," Journal of the Chinese Chemical Society, vol. 45, pp. 209-211 (1998).

Guido Alberti et al., "Thermodynamic Features in Acrylic Fiber Dyeing with Basic Dyes," Textile Research Journal, vol. 54, pp. 105-107 (1984).

Feng-Wen Yen et al., "The Design and Synthesis of Bisazo Series Compound Used in Organophotoconductor," MRL Bull. Res. Dev., vol. 6, No. 2, pp. 21-27 (1992).

Guido Viscardi et al., "Disperse and Cationic Azo Dyes from Heterocyclic Intermediates," Dyes and Pigments, vol. 19, pp. 69-79 (1992).

Piero Savarino et al., "Disperse and Cationic Dyes from Aminophenyl-X-Axolo-Pyridines," Dyes and Pigments, vol. 11, pp. 163-172 (1989).

Robert M. Schelkun, "Subtype-Selective N-Methyl-D-aspartate Receptor Antagonists: Benzimidazalone and Hydantoin as Phenol Replacements," Journal of Medicinal Chemistry, vol. 43, No. 9, pp. 1892-1897 (2000).

* cited by examiner

COMPOSITION COMPRISING AT LEAST ONE MIXED DYE BASED ON AT LEAST ONE CHROMOPHORE OF AZO OR TRI(HETERO) ARYLMETHANE TYPE, DYEING PROCESS AND MIXED DYES.

This application claims benefit of U.S. Provisional Application No. 60/568,270, filed May 6, 2004, and of French Patent Application No. 04/50380, filed Feb. 27, 2004, both of which are incorporated herein by reference.

The present disclosure relates to a dye composition comprising one or more mixed dyes comprising at least one chromophore chosen from chromophores of azo type and chromophores of tri(hetero)arylmethane type, and also to a process for dyeing keratin fibers, such as human keratin fibers, using the composition. The present disclosure also relates to the mixed dyes per se.

It is known practice to dye keratin fibers such as human hair with dye compositions comprising direct dyes. The direct dyes are colored and coloring molecules that have affinity for the fibers. It is known practice, for example, to use direct dyes of the nitrobenzene type, anthraquinone dyes, nitropyridines or dyes of the azo, xanthene, acridine, azine or triarylmethane type.

These dyes are usually applied to the fibers, optionally in the presence of an oxidizing agent, if it is desired to obtain simultaneous lightening of the fibers. Once the action time has elapsed, the fibers are rinsed, optionally washed, and dried.

The colorations resulting from the use of direct dyes may be temporary or semi-permanent colorations, since the nature of the interactions that bind the direct dyes to the keratin fiber, and their desorption from the surface and/or from the core of the fiber, are responsible for their weak dyeing power and their relatively poor wash-fastness or perspiration-fastness.

An additional difficulty may also arise, associated with the fact that, in order to obtain a particular color, it is necessary in most cases, if not all cases, to mix several dyes. However, each dye does not have the same affinity for the fiber, which is reflected either by heterogeneous colorations or by changing of the color over time, for example, after washing the fibers one or more times, exposure to sunlight, etc.

Therefore, disclosed herein are direct dyes that do not have at least one of the drawbacks of the existing direct dyes.

For example, disclosed herein are direct dyes that can afford varied shades without any problem of changing of the color over time.

Disclosed herein is a dye composition comprising, in a medium suitable for dyeing keratin fibers such as human keratin fibers, at least one mixed dye comprising at least two different chromophores, wherein at least one of the chromophores is chosen from chromophores of the azo family and chromophores of the tri(hetero)arylmethane family; and the chromophores are linked together via at least one linker that stops delocalization of the electrons of each of the chromophores. The mixed dyes whose chromophores are all of azo type are not in accordance with the present disclosure.

Further disclosed herein is a process for dyeing keratin fibers such as human keratin fibers, comprising applying the abovementioned dye composition to the keratin fibers, optionally in the presence of at least one oxidizing agent, leaving it to act for a time that is sufficient to obtain the desired coloration, optionally rinsing the keratin fibers, optionally washing and rinsing again the fibers and then drying the fibers or leaving the fibers to dry.

Even further disclosed herein are mixed dyes comprising at least two different chromophores, wherein at least one of the chromophores is chosen from chromophores of the azo family and chromophores of the tri(hetero)arylmethane family; and the chromophores are linked together via at least one linker that stops delocalization of the electrons of each of the chromophores, with the exception of the following four compounds. In addition, the mixed dyes whose chromophores are all of azo type are not in accordance with the present disclosure.

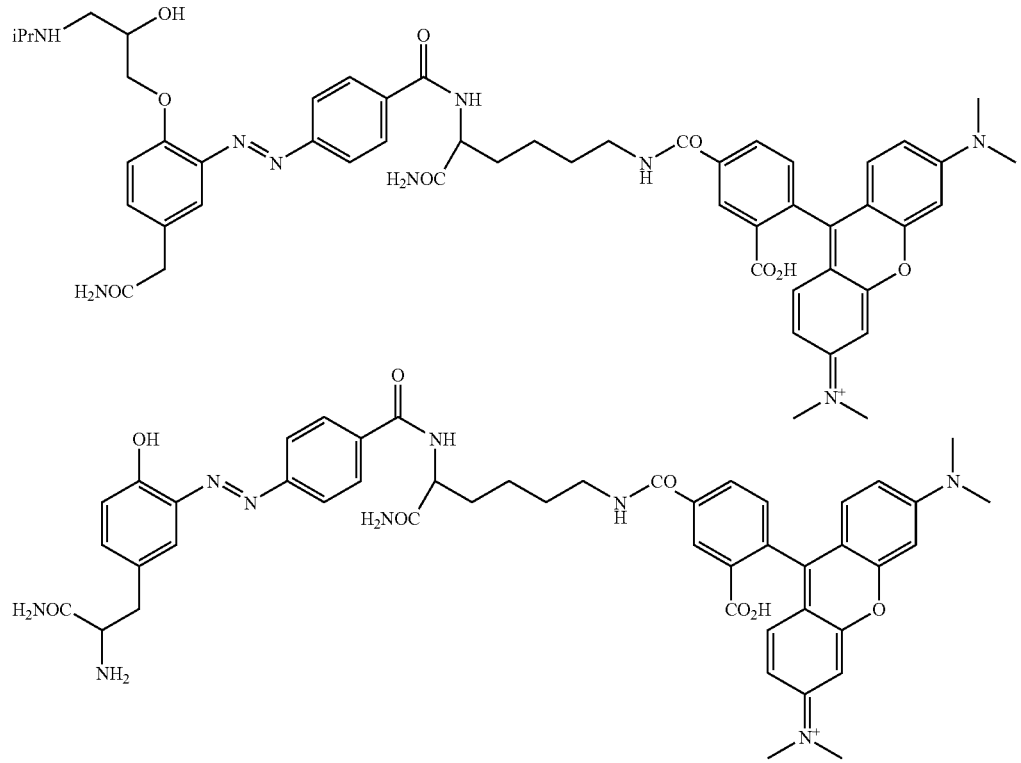

-continued

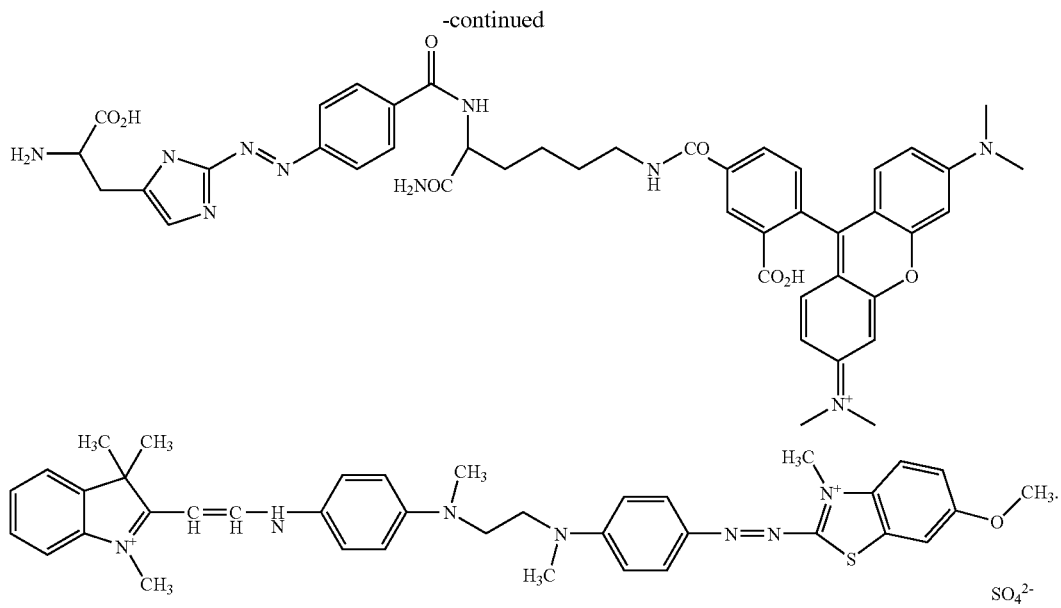

It has been found that the dye composition as disclosed herein makes it possible to obtain strong, light-stable colors that may be resistant to bad weather, washing and perspiration, and show good fastness over time.

Other characteristics and advantages of the present disclosure will emerge more clearly on reading the description and the examples below.

As used herein, and unless otherwise indicated, the term "substituted alkyl, substituted aryl (or aromatic) or substituted heteroaryl (or heteroaromatic) radical" means an alkyl, aryl or heteroaryl radical bearing at least one entity chosen from a hydroxyl radical; halogen atoms such as chlorine and fluorine; linear and branched, substituted and unsubstituted $C_1$-$C_8$ such as $C_1$-$C_4$ alkoxy radicals; linear and branched, substituted and unsubstituted monohydroxyalkoxy radicals in which the alkyl portion is of $C_1$-$C_8$ such as $C_1$-$C_4$; linear and branched, substituted and unsubstituted $C_2$-$C_8$ such as $C_2$-$C_4$ polyhydroxyalkoxy radicals; amino radicals substituted with at least one alkyl radical chosen from linear and branched, substituted and unsubstituted $C_1$-$C_8$ such as $C_1$-$C_6$ alkyl radicals, which may be identical or different, and/or with at least one optionally substituted, such as $C_6$ aryl radical; a thiol radical; linear and branched, substituted and unsubstituted $C_1$-$C_8$ such as $C_1$-$C_4$ alkylthio radicals; a carboxylic radical in acid or salified form (for example, with an alkali metal or a substituted or unsubstituted ammonium); linear and branched, substituted and unsubstituted alkoxycarbonyl radicals in which the alkyl portion is of $C_1$-$C_8$ such as $C_1$-$C_4$; alkylamide radicals in which the alkyl portion is chosen from linear and branched, substituted and unsubstituted and of $C_1$-$C_8$ such as $C_1$-$C_4$; alkylcarbamyl radicals in which the alkyl portion is chosen from linear and branched, substituted and unsubstituted and of $C_1$-$C_8$ such as $C_1$-$C_4$; a nitro radical; a sulfonyl radical; linear and branched, substituted and unsubstituted $C_1$-$C_8$ such as $C_1$-$C_4$ alkylsulfonyl radicals; a sulfonylamino radical; and alkylsulfonylamido radicals in which the alkyl portion is chosen from linear and branched, substituted and unsubstituted and of $C_1$-$C_8$ such as $C_1$-$C_4$.

As disclosed herein, a heteroaromatic, or heteroaryl, radical means an aromatic radical in which at least one of the carbon atoms is replaced with a hetero atom, such as a nitrogen, oxygen or sulfur atom.

Furthermore, when it is indicated that the alkyl or aryl radical or the alkyl or aryl portion of a radical substituting another radical, is itself substituted, this means that it comprises at least one substituent chosen from hydroxyl groups; amino groups; amino groups substituted with at least one alkyl radical chosen from linear and branched $C_1$-$C_4$ alkyl radicals, which may be identical or different, optionally bearing at least one hydroxyl group; and linear and branched $C_1$-$C_4$ alkoxy radicals optionally bearing at least one hydroxyl group.

When mention is made of amino radicals bearing two substituents chosen from optionally substituted alkyl radicals, it means that the alkyl radicals can also form, with the nitrogen atom to which they are attached, a 5- or 6-membered ring, at least one of the carbon atoms of which may be replaced with at least one atom chosen from nitrogen, oxygen and sulfur atoms.

Furthermore, unless otherwise indicated, the limits delimiting the extent of a range of values are included in this range of values.

In addition, since the mixed dyes as disclosed herein are, for example, cationic, their counterions are chosen from cosmetically acceptable anions, of mineral or organic nature. Examples of anions of mineral nature that may be mentioned include halides, for instance chlorides or bromides; hydroxides; sulfates; hydrogen sulfates; carbonates; and hydrogen carbonates.

Examples of anions of organic nature that are suitable include anions such as acetate; citrate; tartrate; alkyl sulfates for which the linear or branched alkyl portion is of $C_1$-$C_6$, for instance the methosulfate or ethosulfate ion; alkylsulfonates for which the linear or branched alkyl portion is of $C_1$-$C_6$; arylsulfonates for which the aryl portion, such as phenyl, is optionally substituted with at least one alkyl radical chosen from $C_1$-$C_4$ alkyl radicals.

The Mixed Dyes

As disclosed herein, the at least one mixed dye comprises at least two different chromophores, wherein at least one of the chromophores is chosen from chromophores of the azo family and chromophores of the tri(hetero)arylmethane family, wherein the chromophores are linked together via at least one linker that stops delocalization of the electrons of each of the chromophores. The mixed dyes whose chromophores are all of azo type do not form part of the present disclosure.

In one embodiment, at least one of the chromophores of the mixed dye bears at least one cationic charge.

As used herein, the term "chromophore" means a radical derived from a dye, i.e., a radical of a molecule that absorbs in the visible range from 400 to 800 nm. This absorbance of the dye does not require either any prior oxidation of the dye, or any association with (an)other chemical species.

When it is mentioned that the chromophores are different, this means that at least two of them, such as all of them, differ in their chemical structure. Such chromophores may be chromophores derived from different families or from the same family provided that they have different chemical structures. For example, the chromophores may be chosen from the same family of dyes but differ in the chemical structure of the radicals constituting them.

In one embodiment, the at least one mixed dye comprises two to four chromophores such as two to three chromophores.

When the at least one mixed dye comprises more than two chromophores, at least one of these chromophores is different from the other(s).

For example, the at least one mixed dye comprises two chromophores.

In one embodiment, at least one of the cationic chromophore is a chromophore comprising at least one quaternized nitrogen atom.

Furthermore, the at least one cationic charge may or may not be engaged in a ring.

Moreover, as indicated above, in one embodiment, at least one of the chromophores of the mixed dye comprises at least one cationic charge, and in some cases only one cationic charge.

For example, each of the chromophores comprises at least one cationic charge, such as only one cationic charge.

In another embodiment, the at least one mixed dye has an overall cationic charge, under the conditions of use of this mixed dye.

The at least one mixed dye present in the composition disclosed herein comprises at least one chromophore chosen from chromophores of the azo family and chromophores of the tri(hetero)arylmethane family.

The chromophores of the azo family are chosen from compounds comprising at least one —N=N— sequence, the two nitrogen atoms of which are not simultaneously engaged in a ring. However, it is not excluded for one of the two nitrogen atoms of the —N=N— sequence to be engaged in a ring.

In one embodiment, the at least one mixed dye comprises at least one cationic azo chromophore.

Such cationic azo chromophores are described, for example, in documents EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1221 122, DE 4 220 388, DE 4 137 005, WO 01/66646, U.S. Pat. No. 5,708,151, WO 95/01772, WO 95/15144, GB 1 195 386, U.S. Pat. No. 3,524,842, U.S. Pat. No. 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 37783; Text. Res. J. (1984), 54(2), 105-7; Chim. Ind. (Milan) (1974), 56(9), 600-3; Khim. Tekhnol. (1979), 22(5), 54853; Ger. Monatsh. Chem. (1975), 106(3), 6438; MRL Bull. Res. Dev. (1992), 6(2), 21-7; Lihua Jianyan, Huaxue Fence (1993), 29(4), 2334; Ann. Chim. (Rome) (1975), 65(5-6), 305-14; Dyes Pigm. (1992), 19(1), 69-79; and Dyes Pigm. (1989), 11(3), 163-72.

Examples that may be mentioned include the chromophores of the azo family of formula (I) below, and also the tautomeric forms thereof:

$$A_1-[N=N-(A_3)_y]_x-A_2 \quad (I)$$

wherein:

x is an integer ranging from 1 to 3;

y is 0 or 1;

for example, if y is equal to 0, then x is equal to 1;

$A_1$ and $A_2$, which may be identical or different, are each chosen from $C_6$-$C_{30}$ aromatic radicals and 5- to 30-membered heteroaromatic radicals, comprising at least one hetero atom chosen from nitrogen, oxygen and sulfur atoms; wherein at least one of the groups $A_1$ and $A_2$ is substituted;

$A_1$ or $A_2$ is linked to the linker of the mixed dye;

$A_3$ is chosen from monoaromatic and polyaromatic $C_6$-$C_{30}$ divalent radicals, which are optionally substituted, for example, with one or more entities, which may be identical or different, chosen from linear and branched $C_1$-$C_6$ alkyl radicals; linear and branched $C_1$-$C_6$ alkoxy radicals; a hydroxyl radical; an amino radical; an amino radical substituted with at least one alkyl radical chosen from linear and branched $C_1$-$C_6$ alkyl radicals, which may be identical or different, optionally bearing at least one hydroxyl radical; a nitro radical; halogen atoms; $C_1$-$C_{12}$ alkylsulfonamido (alkyl-$SO_2$—NH—), $C_1$-$C_{12}$ alkylsulfamoyl (alkyl-NH—$SO_2$—), acyloxy in which the alkyl portion is of $C_1$-$C_{12}$; alkoxycarbonyl radicals in which the alkyl portion is of $C_1$-$C_{12}$; and a carboxyl radical.

For example, $A_1$ and $A_2$, which may be identical or different, are each chosen from $C_6$-$C_{30}$ aromatic radicals and 5- to 30-membered heteroaromatic radicals, comprising at least one hetero atom chosen from nitrogen, oxygen and sulfur atoms; wherein the $C_6$-$C_{30}$ aromatic radicals and 5- to 30-membered heteroaromatic radicals are optionally substituted with at least one entity chosen from linear and branched, substituted and unsubstituted $C_1$-$C_8$ alkyl radicals; $C_5$ and $C_6$ (hetero)aromatic radicals, which are optionally substituted with at least one alkoxy radical chosen from linear and branched $C_1$-$C_6$ alkoxy radicals; an amino radical; an amino radical substituted with at least one alkyl radical chosen from linear and branched $C_1$-$C_6$ alkyl radicals, which may be identical or different, optionally bearing at least one hydroxyl group; an amido radical; a hydroxyl radical; halogen atoms; a nitro radical; and a cyano radical.

In one embodiment, at least one of the groups $A_1$ and $A_2$ is cationic.

In another embodiment, the chromophores of the azo family are chosen from those of formula (I) wherein x is 1 and y is 0.

For example, the chromophores of the azo family are chosen from those of formula (I) with x=1 and y=0, and also the tautomeric forms thereof, wherein:

$A_1$ is chosen from radicals of formulae (II), (III), and (IV)

Formula (II)

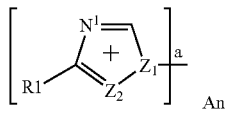

Formula (III)

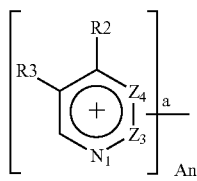

Formula (IV)

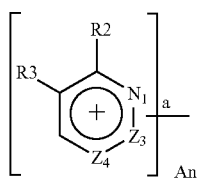

wherein the bond a is linked to the azo group either via the ring or via $N^1$ (or $N_1$), $Z_1$, $Z_2$, $Z_3$, $Z_4$, $R_1$, $R_2$ or $R_3$;

$Z_1$ is chosen from oxygen and sulfur atoms, a radical $NR_4$ and a radical $CR_5$, $Z_2$ is chosen from a nitrogen atom and a radical $CR_6$, $Z_3$ is chosen from a nitrogen atom and a radical $CR_7$, $Z_4$ is chosen from a nitrogen atom and a radical $CR_8$, $R_5$ and $R_6$ can together form an aromatic ring, An is a cosmetically acceptable anion, $A_2$ is an optionally substituted, optionally cationic group chosen from $C_6$-$C_{30}$ aromatic and 5- to 30-membered heteroaromatic groups, linked to the azo group either via the ring or one of its substituents.

For example, $A_2$ is a carbon-based aromatic group or a pyridine group of formula (V):

Formula (V)

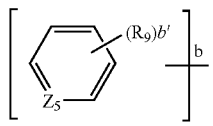

wherein:

the bond b is linked to the azo group via the ring;

$Z_5$ is chosen from a nitrogen atom and a radical $CR_{10}$;

$R_1$, $R_2$, $R_3$, $R_5$, $R_6$, $R_7$, $R_8$, $R_9$ and $R_{10}$, which may be identical or different, are each chosen from a hydrogen atom; linear and branched, optionally substituted $C_1$-$C_8$ alkyl radicals; optionally substituted 5- and 6-membered (hetero)aryl radicals; halogen atoms; a hydroxyl group; linear and branched, optionally substituted $C_1$-$C_8$ alkoxy radicals; an amino radical; an amino radical substituted with at least one alkyl radical chosen from linear and branched $C_1$-$C_6$ alkyl radicals, which may be identical or different, optionally bearing at least one hydroxyl group; a nitro group; a cyano group; $C_1$-$C_{12}$ alkylsulfonamido (alkyl-$SO_2$—NH—); $C_1$-$C_{12}$ alkylsulfamoyl (alkyl-NH—$SO_2$—); acyloxy in which the alkyl portion is of $C_1$-$C_{12}$; alkoxycarbonyl in which the alkyl portion is of $C_1$-$C_{12}$; and a carboxyl group;

$R_4$ is chosen from linear and branched, optionally substituted $C_1$-$C_8$ alkyl radicals;

$R_1$ with $R_6$, and $R_7$ with $R_8$ may form an aromatic ring;

the coefficient b' is equal to 4;

An is a cosmetically acceptable anion of organic or mineral nature.

For example, $R_1$, $R_2$, $R_3$, $R_5$, $R_6$, $R_7$, $R_8$, $R_9$ and $R_{10}$, which may be identical or different, are each chosen from a hydrogen atom, linear and branched $C_1$-$C_4$ alkyl radicals, optionally substituted with at least one halogen atom, a nitro group, a cyano group, an amido group (—$CONH_2$), a $C_1$-$C_4$ alkoxy group; a hydroxyl group; linear and branched $C_1$-$C_8$ alkoxy radicals; an amino radical; an amino radical substituted with at least one alkyl radical chosen from linear and branched $C_1$-$C_4$ alkyl radicals, which may be identical or different, optionally bearing at least one hydroxyl group.

For example, $R_4$ is chosen from linear and branched, optionally substituted $C_1$-$C_4$ alkyl radicals.

In one embodiment, $Z_1$ is a radical $NR_4$, $Z_2$ is a radical $CR_6$, and the azo group is linked to the group of formula (II) via the ring.

In another embodiment, the group $A_1$ is of formula (III) or (IV) and the azo group is linked via the ring or $Z_3$, wherein $Z_3$ is a radical $CR_7$.

In addition, the chromophore is linked to the linker via the group $A_1$ or the group $A_2$.

Whether the chromophore and the linker are linked via the group $A_1$ or via the group $A_2$, the bond may be made either via one of the ring members of the rings of the groups of formulae (II) to (IV) or of the (hetero)aromatic group $A_2$, such as the group of formula (V), or via one of the substituents borne by the ring members of the abovementioned rings.

For example, if the chromophore and the linker are linked via the group $A_1$, the bond may be obtained, for example, via the nitrogen atom $N^1$ (or $N_1$), or one of the radicals $R_1$, $R_2$, $R_3$, $R_4$, $R_5$, $R_6$, $R_7$ and $R_8$. In one embodiment, the bonding takes place via the nitrogen atom $N^1$ (or $N_1$).

In the case where the chromophore and the linker are not linked via the nitrogen atom $N^1$ (or $N_1$), then the nitrogen atom $N^1$ (or $N_1$) optionally bears a radical, which is identical to or different from one of the radicals $R_1$ to $R_{10}$, such as via a linear or branched, optionally substituted $C_1$-$C_4$ alkyl radical.

In a first embodiment, when the chromophore and the linker are linked via the group $A_2$, such as via a group $A_2$ of formula (V), then the chromophore and the linker may be linked via one of the radicals $R_9$ and $R_{10}$ or via the ring, such as with, in the case of linking via a ring, the presence of an oxygen or nitrogen atom directly linked to the aromatic ring. In accordance with this embodiment, the chromophore and the linker are linked via a radical $R_9$. For example, $R_9$ is linked to the ring via a nitrogen or oxygen atom.

In a second embodiment, the chromophore and the linker are linked via the group $A_1$ such as via the nitrogen atom $N^1$ (or $N_1$).

In a third embodiment, the chromophore and the linker are linked via the group $A_1$ such as via the group $Z_1$, for example, the radical C—$R_5$, further, for example, directly via this carbon atom. According to this embodiment, $R_1$ and $R_6$ may together form a 6-membered aromatic ring.

In the case where the chromophore is linked to the linker via the group $A_2$, at least one of the nitrogen atoms of formulae (II) to (IV) optionally bears a linear, branched or cyclic $C_1$-$C_{12}$ alkyl radical, optionally substituted with at least one hydroxyl group, a $C_1$-$C_8$ alkoxy group, an amino group, an amino group substituted with at least one alkyl radical chosen from linear and branched $C_1$-$C_8$ alkyl radicals, which may be identical or different, optionally bearing at least one hydroxyl group.

The chromophores of the tri(hetero)arylmethane family are chosen, for example, from the compounds of formulae (VI) to (VIII) below:

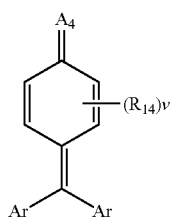

(VI)

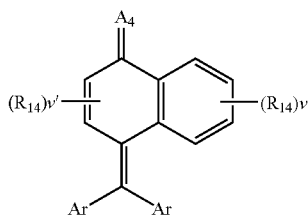

(VII)

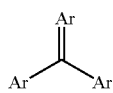

(VIII)

wherein:
Ar, which may be identical or different, is chosen from an optionally substituted aryl radical, such as phenyl or naphthyl and an optionally substituted heterocycle;
$A_4$ is chosen from O, N—$R_{15}$, and $N^+(R_{16})_2$ wherein $R_{15}$ and $R_{16}$, which may be identical or different, are each chosen from a hydrogen atom, linear and branched $C_1$-$C_8$ alkyl radicals, which are optionally substituted with, for example, at least one hydroxyl; an amido group (—$CONH_2$), $C_1$-$C_4$ alkoxy groups; an amino radical; an amino radical substituted with at least one alkyl radical chosen from linear and branched $C_1$-$C_4$ alkyl radicals, which may be identical or different, optionally bearing at least one hydroxyl group;
$R_{14}$, which may be identical or different, is chosen from a hydrogen atom; halogen atoms, such as chlorine and fluorine; a sulfonylamino group; a hydroxyl group; linear and branched, optionally substituted $C_1$-$C_8$ alkyl radicals; linear and branched, optionally substituted $C_1$-$C_8$ alkoxy radicals; linear and branched, optionally substituted $C_1$-$C_8$ alkylthio radicals; an amino radical; an amino radical substituted with at least one alkyl radical chosen from linear and branched $C_1$-$C_8$ alkyl radicals, which may be identical or different, optionally bearing at least one hydroxyl group; a heterocyclic radical; a nitro group; a cyano group; an optionally substituted aryl radical, such as of $C_6$; an acyl group; linear and branched $C_1$-$C_8$ alkoxycarbonyl radicals; a carboxamido group; —$CO_2H$; —$SO_3H$; —$PO_3H_2$; and —$PO_4H_2$;
v is equal to 4; and v' is equal to 2.

For example, when Ar is a heterocycle, this heterocycle may be chosen from substituted and unsubstituted heterocycles of the type such as thiophene, benzothiophene, furan, benzofuran, indole, indoline, carbazole, pyridine, dehydroquinoline, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperonyl, piperazine, azetidine, pyrrolidine or aziridine.

Furthermore, the radicals Ar may be substituted, for example, with at least one entity chosen from halogen atoms, such as chlorine and fluorine; a sulfonylamino group; a hydroxyl radical; linear and branched, optionally substituted $C_1$-$C_8$ alkyl radicals; linear and branched, optionally substituted $C_1$-$C_8$ alkoxy radicals; linear and branched, optionally substituted $C_1$-$C_8$ alkylthio radicals; an amino radical; an amino radical substituted with at least one alkyl radical chosen from linear and branched $C_1$-$C_8$ alkyl radicals, which may be identical or different, optionally bearing at least one hydroxyl group; a heterocyclic radical; a nitro group; a cyano group; an optionally substituted aryl radical, such as of $C_6$; an acyl group; linear and branched $C_1$-$C_8$ alkoxycarbonyl radicals; a carboxamido group; —$CO_2H$; —$SO_3H$; —$PO_3H_2$; and —$PO_4H_2$.

The chromophore may be linked to the linker via one of the groups $A_4$, $R_{14}$, $R_{15}$, $R_{16}$ or Ar, or via a ring. In the case of linking via a ring, the radical borne by the ring represents a single bond between the chromophore and the linker.

The at least one mixed dye as disclosed herein may also comprise at least one chromophore of the methine family.

The chromophores of the methine family are, for example, compounds comprising at least one sequence chosen from >C=C< and —N=C<, the two atoms of which are not simultaneously engaged in a ring. However, one of the nitrogen or carbon atoms of the sequences may be engaged in a ring.

For example, the chromophores of the methine family are derived from chromophores of methine, azomethine, mono- and di-arylmethane, indamine (or diphenylamine), indophenol, indoaniline, carbocyanin, azacarbocyanin and isomers thereof, diazacarbocyanin and isomers thereof, tetraazacarbocyanin or hemicyanin type.

Further, for example, among the chromophores of the methine family, mention may be made of the chromophores of formula (IX) below, and also the tautomeric forms thereof:

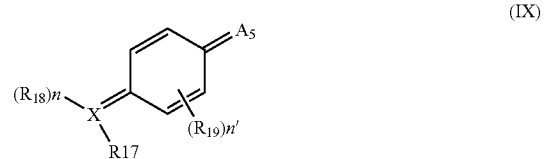

(IX)

wherein:
$R_{17}$ and $R_{18}$, which may be identical or different, are each chosen from a hydrogen atom; $C_6$-$C_{30}$ aryl radicals, ($C_1$-$C_8$)alkylaryl radicals, wherein the aryl portion is optionally substituted with one or more groups, which may be identical or different, chosen, for example, from a hydroxyl group, linear and branched, substituted and unsubstituted $C_1$-$C_4$ alkoxy groups, amino groups, amino groups substituted with at least one alkyl radical chosen from linear and branched $C_1$-$C_4$ alkyl radicals, which may be identical or different, optionally bearing at least one hydroxyl group, halogen atoms, such as chlorine; a heterocyclic radical chosen, for example, from thiophene, furan, piperonyl, indole, indoline, pyridine, carbazole, dehydroquinoline and chromone heterocycles;

$R_{17}$ and $R_{18}$ cannot simultaneously be either an aromatic radical or a heteroaromatic radical;

$R_{19}$, which may be identical or different, is each chosen from a hydrogen atom; linear and branched, optionally substituted $C_1$-$C_8$ alkyl radicals; optionally substituted $C_6$-$C_{30}$ aryl radicals; an amino radical; an amino radical substituted with at least one alkyl radical chosen from linear and branched $C_1$-$C_4$ alkyl radicals, optionally bearing at least one hydroxyl group; a hydroxyl group; linear and branched $C_1$-$C_8$ alkoxy radicals, optionally bearing at least one hydroxyl group, a $C_1$-$C_4$ alkoxy group; and halogen atoms such as chlorine;

X is a nitrogen atom or a carbon atom;

the coefficient n is 0 when X is a nitrogen atom, and is 1 when X is a carbon atom;

the coefficient n' is equal to 4;

$A_5$ is chosen from an amino group; an amino group substituted with at least one alkyl radical chosen from linear and branched $C_1$-$C_8$ alkyl radicals, which may be identical or different, optionally bearing at least one hydroxyl group, an ammonium group $N^+(R_{20})_2$, wherein $R_{20}$; which may be identical or different, is each an optionally substituted $C_1$-$C_8$ alkyl radical; a $C_6$ aryl radical, which is optionally substituted, such as with at least one entity chosen from a hydroxyl group, halogen atoms, such as chlorine and fluorine, nitro groups, cyano groups, linear and branched $C_1$-$C_4$ alkoxy groups, linear and branched $C_1$-$C_4$ monohydroxyalkoxy groups, linear and branched $C_2$-$C_4$ polyhydroxyalkoxy groups, amino groups, which are optionally substituted with at least one radical chosen from linear and branched $C_1$-$C_4$ alkyl and hydroxyalkyl radicals, which may be identical or different.

Moreover, the chromophore is linked to the linker via the group $A_5$ or via one of the radicals $R_{17}$, $R_{18}$, $R_{19}$ and $R_{20}$ or directly to the (hetero)aromatic ring(s). In the case of linking via the ring, the radical $R_{19}$ represents a single bond between the chromophore and the linker.

For example, when $R_{17}$ or $R_{18}$ is a $C_6$ aryl radical, this $C_6$ aryl radical may optionally be substituted, such as with at least one entity chosen from a hydroxyl group; an amino group; an amino group substituted with at least one alkyl radical chosen from $C_1$-$C_8$ alkyl radicals, which may be identical or different, optionally bearing at least one hydroxyl group; halogen atoms; $C_1$-$C_{12}$ alkylsulfonamido radicals (alkyl-$SO_2$—NH—); $C_1$-$C_{12}$ alkylsulfamoyl radicals (alkyl-NH—$SO_2$—); an acyloxy radical in which the alkyl portion is of $C_1$-$C_{12}$; an alkoxycarbonyl radical in which the alkyl portion is of $C_1$-$C_{12}$; and a carboxyl radical.

Chromophores that may be used herein are also chosen, for example, from those of formula (X) below:

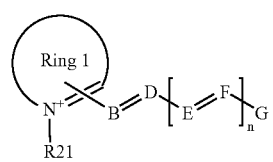

(X)

and, where appropriate, the tautomeric forms thereof;

wherein:

B, D, E and F, which may be identical or different, are each chosen from a nitrogen atom and a group C—$R_{22}$, wherein $R_{22}$, which may be identical or different, is chosen from a hydrogen atom, a $C_1$-$C_8$ alkyl radical which is optionally substituted, such as with at least one hydroxyl group; linear and branched $C_1$-$C_4$ alkoxy radicals; an amino radical; an amino radical substituted with at least one alkyl radical chosen from linear and branched $C_1$-$C_4$ alkyl radicals, which may be identical or different, optionally bearing at least one hydroxyl group; an optionally substituted $C_6$ aryl radical; and an optionally substituted 5- to 12-membered heteroaryl radical;

n=0 or 1;

G is a Ring 4 as defined below, or one of the following two residues:

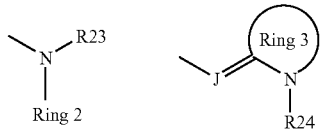

wherein:

$R_{21}$ and $R_{24}$, which may be identical or different, are each chosen from linear and branched, optionally substituted $C_1$-$C_8$ alkyl radicals; and an optionally substituted benzyl radical;

$R_{23}$ is chosen from a hydrogen atom, a $C_1$-$C_8$ alkyl radical which is optionally substituted, such as with at least one hydroxyl group, linear and branched $C_1$-$C_4$ alkoxy radicals, an amino radical, an amino radical substituted with at least one alkyl radical chosen from linear and branched $C_1$-$C_4$ alkyl radicals, which may be identical or different, optionally bearing at least one hydroxyl group; an optionally substituted $C_6$ aryl radical; and an optionally substituted $C_2$-$C_{12}$ heteroaryl radical;

J is chosen from a nitrogen atom and a group C—$R_{25}$, wherein $R_{25}$ has the same meaning as $R_{22}$;

Ring 1 is chosen from 5- to 12-membered heteroaromatic radicals, bearing at least one cationic charge on a nitrogen atom and optionally comprising at least one other hetero atom chosen from nitrogen, oxygen and sulfur atoms, wherein the 5- to 12-membered heteroaromatic radicals are optionally substituted with at least one entity chosen from linear and branched, optionally substituted $C_1$-$C_8$ alkyl radicals; linear and branched, optionally substituted $C_1$-$C_8$ alkoxy radicals; an amino radical; an amino radical substituted with at least one alkyl radical chosen from linear and branched $C_1$-$C_8$ alkyl groups, which may be identical or different, optionally bearing at least one hydroxyl group; a $C_5$-$C_6$ aromatic radical; a hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);

Ring 2 is chosen from $C_6$-$C_{12}$ aromatic radicals and 5- to 12-membered heteroaromatic radicals, comprising at least one hetero atom chosen from nitrogen, oxygen and sulfur atoms, wherein the $C_6$-$C_{12}$ aromatic radicals and the 5- to 12-membered heteroaromatic radicals are optionally substituted with at least one entity chosen from linear and branched $C_1$-$C_8$ alkyl radicals; linear and branched $C_1$-$C_8$ alkoxy radicals; an amino radical; an amino radical substituted with at least one alkyl group chosen from linear and branched $C_1$-$C_8$ alkyl groups, which may be identical or different, optionally bearing at least one hydroxyl group; a (hetero)aromatic radical, which is, for example, 5- to 6-membered; and a hydroxyl group. In one embodiment, Ring 2 is a $C_6$-$C_{30}$ aromatic radical, optionally substituted as indicated above;

Ring 3 is chosen from 5- and 6-membered heteroaromatic radicals comprising at least one hetero atom chosen from nitrogen, oxygen and sulfur atoms, wherein the 5- and 6-membered heteroaromatic radicals are optionally substituted with at least one entity chosen from linear and branched $C_1$-$C_8$ alkyl radicals; linear and branched $C_1$-$C_8$ alkoxy radicals; an amino radical; an amino radical substituted with at least one alkyl radical chosen from linear and branched $C_1$-$C_8$ alkyl radicals, which may be identical or different, optionally bearing at least one hydroxyl group; a $C_5$-$C_6$ aromatic radical; a hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);

Ring 4 is chosen from $C_6$-$C_{12}$ aromatic radicals and 5- to 12-membered heteroaromatic radicals, comprising at least one hetero atom chosen from nitrogen, oxygen and sulfur atoms; wherein the $C_6$-$C_{12}$ aromatic radicals and the 5- to 12-membered heteroaromatic radicals are optionally substituted with at least one entity chosen from linear and branched $C_1$-$C_8$ alkyl radicals; linear and branched $C_1$-$C_8$ alkoxy radicals; an amino radical; an amino radical substituted with at least one alkyl radical chosen from linear and branched $C_1$-$C_8$ alkyl radicals, which may be identical or different, optionally bearing at least one hydroxyl group; a (hetero)aromatic radical, which is, for example, 5- or 6-membered; and a hydroxyl group; provided that when n is 1 and G is a ring, then B, D, E and F cannot simultaneously be a nitrogen atom; and that when n is 0 and G is a ring, then B and D are not simultaneously a nitrogen atom.

Moreover, the chromophore is linked to the linker via one of the radicals $R_{21}$, $R_{22}$, $R_{23}$, $R_{24}$ and $R_{25}$ or the rings. In this case of linking via the ring, the radical borne by the ring represents a single bond between the chromophore and the linker.

Formula (X) includes the positional isomers corresponding to the various possibilities of insertion of the bond of B onto Ring 1 relative to the quaternized nitrogen atom.

In one embodiment, the chromophore of the methine family is chosen from the compounds of the following formulae, and also the tautomeric forms thereof:

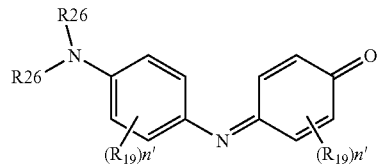
Indamines (diphenylamines)

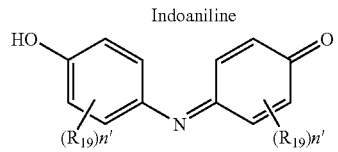
Diphenylmethanes

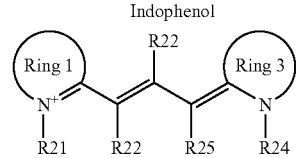
Indoaniline

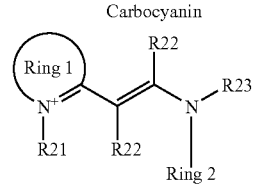
Indophenol

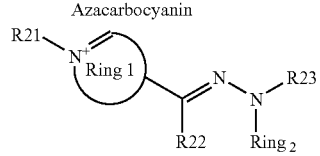
Carbocyanin

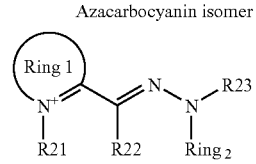
Azacarbocyanin

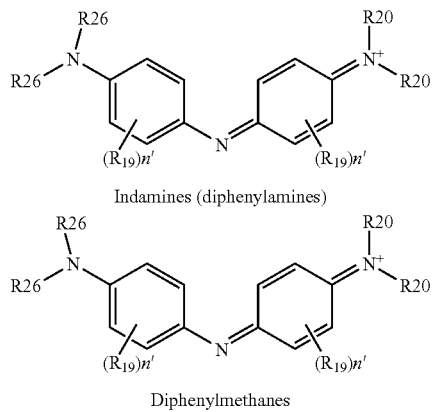
Azacarbocyanin isomer

Diazacarbocyanin

Diazacarbocyanin isomer

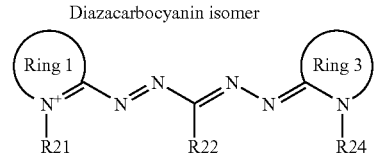
Tetraazacarbocyanin

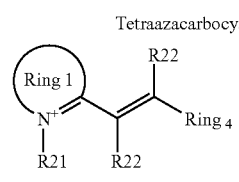
Hemicyanin wherein:

$R_{26}$, which may be identical or different, is chosen from a hydrogen atom, an optionally substituted $C_1$-$C_8$ alkyl radical; a $C_6$ aryl radical, which is optionally substituted, for example, with at least one hydroxyl group, halogen atoms, such as chlorine and fluorine, nitro groups, cyano groups, linear and branched $C_1$-$C_4$ alkoxy groups, linear and branched $C_1$-$C_4$ monohydroxyalkoxy groups, linear and branched $C_2$-$C_4$ polyhydroxyalkoxy groups, amino groups, which may be optionally substituted with at least one radical chosen from linear and branched $C_1$-$C_4$ alkyl and hydroxyalkyl radicals, which may be identical or different;

$R_{20}$, $R_{21}$, $R_{22}$, $R_{23}$, $R_{24}$, $R_{25}$, $R_{26}$, Ring 1, Ring 2, Ring 3 and Ring 4 are defined as above.

For example, Ring 1 is an imidazolium, pyridinium or indolinium ring, optionally substituted as indicated above.

For example, Ring 3 is an imidazole, pyridine or indoline ring, optionally substituted as indicated above.

For example, Ring 2 is a $C_6$ aromatic radical, optionally substituted as indicated above.

For example, Ring 4 is a $C_6$ aromatic radical, optionally substituted as indicated above.

The chromophore may be linked to the linker via one of the groups $R_{19}$, $R_{20}$, $R_{21}$, $R_{22}$, $R_{23}$, $R_{24}$ and $R_{25}$ or via an aromatic or heteroaromatic ring. In the case of attachment via a ring, the radical borne on the ring represents a single bond between the chromophore and the linker.

In one embodiment, the chromophore is chosen from the compounds of formula (X) such as diazacarbocyanins and isomers thereof, and hemicyanins. For example, $R_{22}$, which may be identical or different, is chosen from a hydrogen atom, a $C_1$-$C_8$ alkyl radical, which is optionally substituted, for example, with at least one hydroxyl group; an optionally substituted $C_6$ aryl radical; n=0; G is a Ring 4, or —N($R_{23}$)-Ring 2 wherein $R_{23}$ is chosen from a hydrogen atom, a $C_1$-$C_8$ alkyl radical, which is optionally substituted, for example, with at least one hydroxyl group; the Ring 2 and Ring 4, which may be identical or different, are each an optionally substituted $C_6$ aromatic radical.

In this embodiment, the chromophore and the linker are linked via the radical $R_{21}$.

The chromophores described above may be prepared according to the teaching of the following patent applications and patents: GB 822 846; DE 1 254 118; GB 1 047 796; U.S. Pat. No. 3,652,556; U.S. Pat. No. 3,423,427; BE 702 239; GB 702 240; U.S. Pat. No. 3,995,088; U.S. Pat. No. 4,054,718; U.S. Pat. No. 4,670,385; U.S. Pat. No. 5,094,688; U.S. Pat. No. 5,097,034.

The at least one mixed dye disclosed herein may also comprise at least one chromophore of the carbonyl family.

Among the chromophores of the carbonyl family, examples that may be mentioned include chromophores derived from dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

For example, the chromophores of the carbonyl family are chosen from those of formula (XI) below:

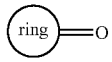

(XI)

wherein the ring is a 5- or 6-membered ring, at least one of the ring members of which is optionally replaced with a hetero atom chosen from oxygen, nitrogen and sulfur atoms, or with an additional carbonyl functional group; wherein the ring is optionally substituted with at least one entity chosen from optionally substituted linear and branched $C_1$-$C_8$ alkyl radicals; a hydroxyl radical; halogen atoms, such as chlorine; and nitro, cyano, amino and alkylamino groups; wherein the ring is optionally fused with at least one $C_6$ aromatic ring, which is possibly fused with at least one aromatic ring, at least one of the carbon atoms of which is optionally replaced with at least one hetero atom chosen from oxygen, nitrogen and sulfur atoms.

Moreover, the chromophore is linked to the linker via one of the radicals substituting the rings or via a ring. In the case of linking via a ring, the radical borne by the ring represents a single bond between the chromophore and the linker.

In one embodiment, the chromophores of the carbonyl family are chosen from those of the following formulae, and also the tautomeric forms:

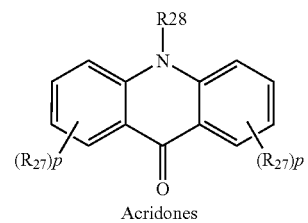

Acridones

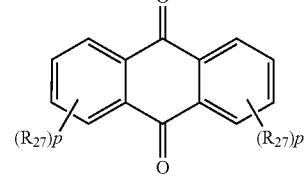

Anthraquinones

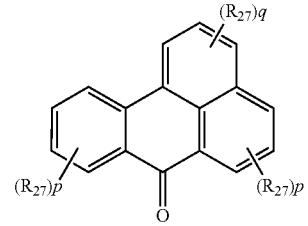

Benzanthrones

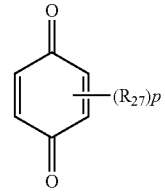

Benzoqionones

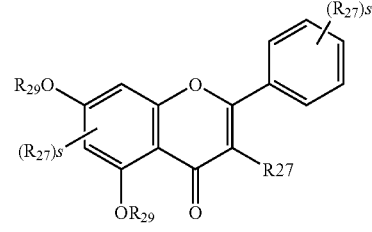

Flavones

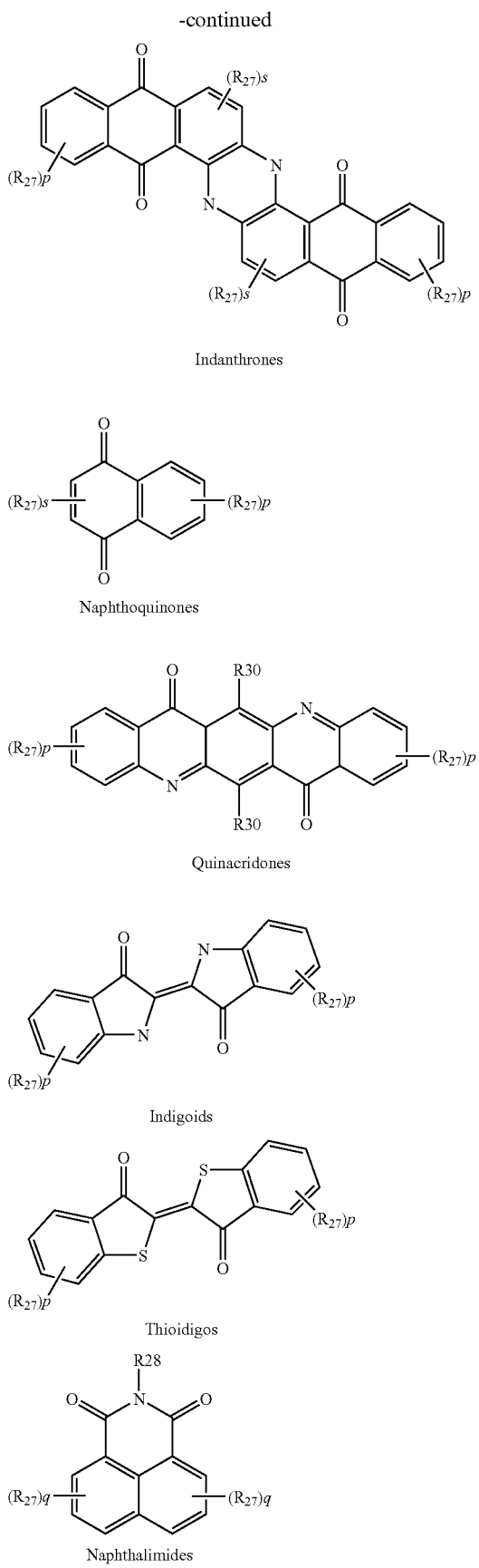

Indanthrones

Naphthoquinones

Quinacridones

Indigoids

Thioidigos

Naphthalimides

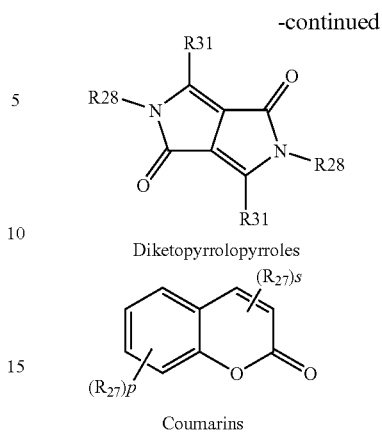

Diketopyrrolopyrroles

Coumarins wherein:

$R_{27}$, $R_{28}$, $R_{30}$ and $R_{31}$, which may be identical or different, are each chosen from a hydrogen atom; linear and branched, optionally substituted $C_1$-$C_8$ alkyl radicals; a hydroxyl group; linear and branched $C_1$-$C_8$ alkoxy radicals; an amino radical; an amino radical substituted with at least one alkyl radical chosen from linear and branched $C_1$-$C_8$ alkyl radicals, which may be identical or different, optionally bearing at least one hydroxyl group; halogen atoms such as chlorine and fluorine; a nitro group; and a cyano group;

$R_{29}$ is chosen from a hydrogen atom and linear and branched, optionally substituted $C_1$-$C_8$ alkyl radicals; $R_{31}$, which may be identical or different, is a $C_6$ aryl radical, which is optionally substituted, for example, with at least one entity chosen from a hydroxyl group, an amino radical, an amino radical substituted with at least one alkyl radical chosen from linear and branched $C_1$-$C_8$ alkyl radicals, which may be identical or different, optionally bearing at least one hydroxyl group, linear and branched $C_1$-$C_8$ alkoxy radicals optionally bearing at least one hydroxyl group, halogen atoms, such as chlorine and fluorine, a nitro group, and a cyano group;

p is equal to 4; q is equal to 3; and s is equal to 2.

The chromophore may be linked to the linker via one of the radicals $R_{27}$, $R_{28}$, $R_{29}$, $R_{30}$ or $R_{31}$ or via one of the aromatic or heteroaromatic rings. In the case of linking via a ring, the radical borne by the ring represents a single bond between the chromophore and the linker.

The at least one mixed dye as disclosed herein may furthermore comprise at least one chromophore of the cyclic azine family.

For example, the chromophore of the cyclic azine family is chosen from the radicals derived from dyes chosen from azine, xanthene, thioxanthene, fluorindine, acridine, (di)oxazine, (di)thiazine and pyronine.

Among the chromophores of the cyclic azine family that may be mentioned, examples include those of formula (XII) below, and also the tautomeric forms thereof:

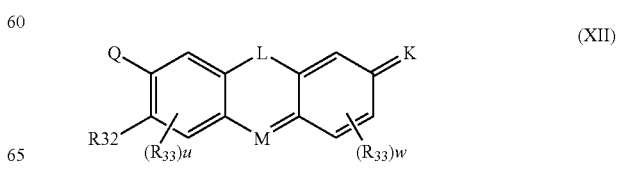

(XII)

wherein:

L is chosen from a hetero atom chosen, for example, from oxygen and sulfur atoms; an NH group; and a group N—$R_{34}$, M is chosen from a hetero atom chosen, for example, from oxygen, sulfur and nitrogen atoms; a group $N^+$—$R_{34}$; a CH group; and a group C—$R_{35}$;

Q and K, which may be identical or different, are each chosen from a hydroxyl group; an amino radical; an amino radical substituted with at least one alkyl radical chosen from linear and branched $C_1$-$C_8$ alkyl radicals, which may be identical or different, optionally bearing at least one hydroxyl group; an optionally substituted aryl radical; an optionally substituted ($C_1$-$C_8$)alkylaryl radical; an ammonium group of the type $N^+(R_{36})_t$, wherein t equals to 2 for K and to 3 for Q, $R_{36}$, which may be identical or different, is chosen from a hydrogen atom; linear and branched $C_1$-$C_8$ alkyl radicals, optionally bearing at least one hydroxyl group; an optionally substituted aryl radical, a ($C_1$-$C_8$) alkylaryl radical, wherein the aryl portion is optionally substituted; an optionally substituted linear or branched $C_1$-$C_8$ alkyl radical, and an optionally substituted linear or branched $C_1$-$C_8$ alkoxy radical; provided that Q and K are not simultaneously an ammonium group of the type $N^+$ $(R_{36})_t$;

$R_{32}$ and $R_{33}$, which may be identical or different, are each chosen from a hydrogen atom; an optionally substituted linear or branched $C_1$-$C_8$ alkyl radical; an amino radical; an amino radical optionally substituted with one or more radicals, which may be identical or different, chosen from linear and branched, optionally substituted $C_1$-$C_8$ alkyl radicals, optionally substituted phenyl radicals; and halogen atoms, such as chlorine and fluorine;

in the case where Q is a substituted or unsubstituted amino radical, or a hydroxyl group, $R_{32}$ may be an alkylamino or alkoxy radical forming, with the nitrogen or oxygen atom of the radical M, a 6-membered ring, optionally fused with an aromatic radical, wherein the aromatic radical is optionally substituted with at least one amino group or an amino group that is optionally substituted with one or more radicals, which may be identical or different, chosen from optionally substituted linear and branched $C_1$-$C_8$ alkyl radicals and optionally substituted phenyl radicals;

$R_{34}$ and $R_{35}$, which may be identical or different, are each chosen from linear and branched $C_1$-$C_8$ alkyl radicals, which are optionally substituted, for example, with at least one entity chosen from a hydroxyl group; linear and branched $C_1$-$C_8$ alkoxy radicals; an amino radical; and an amino radical substituted with at least one alkyl radical chosen from linear and branched $C_1$-$C_8$ alkyl radicals, which may be identical or different, optionally bearing at least one hydroxyl radical.

$R_{34}$ and $R_{35}$, which may be identical or different, may also be chosen from aryl radicals, such as an aryl radical of $C_6$, which are optionally substituted, for example, with at least one entity chosen from linear and branched $C_1$-$C_8$ alkyl radicals; a hydroxyl group; linear and branched $C_1$-$C_8$ alkoxy radicals; an amino radical; an amino radical substituted with at least one alkyl radical chosen from linear and branched $C_1$-$C_8$ alkyl radicals, which may be identical or different, optionally bearing at least one hydroxyl group; halogen atoms such as chlorine and fluorine; a nitro group; and a cyano group. For example, $R_{34}$ and $R_{35}$, which may be identical or different, are each chosen from linear $C_1$-$C_4$ alkyl radicals and an optionally substituted aryl radical.

The coefficient u ranges from 0 to 2; and the coefficient w ranges from 0 to 3.

The chromophore is, for example, linked to the linker via one of the radicals $R_{32}$, $R_{33}$, $R_{34}$, $R_{35}$ or $R_{36}$, or via a ring.

In the case of linking via a ring, the radical borne by the ring represents a single bond between the chromophore and the linker.

In one embodiment, the chromophore of the cyclic azine family is of the formulae below, and also, where appropriate, the tautomeric forms thereof:

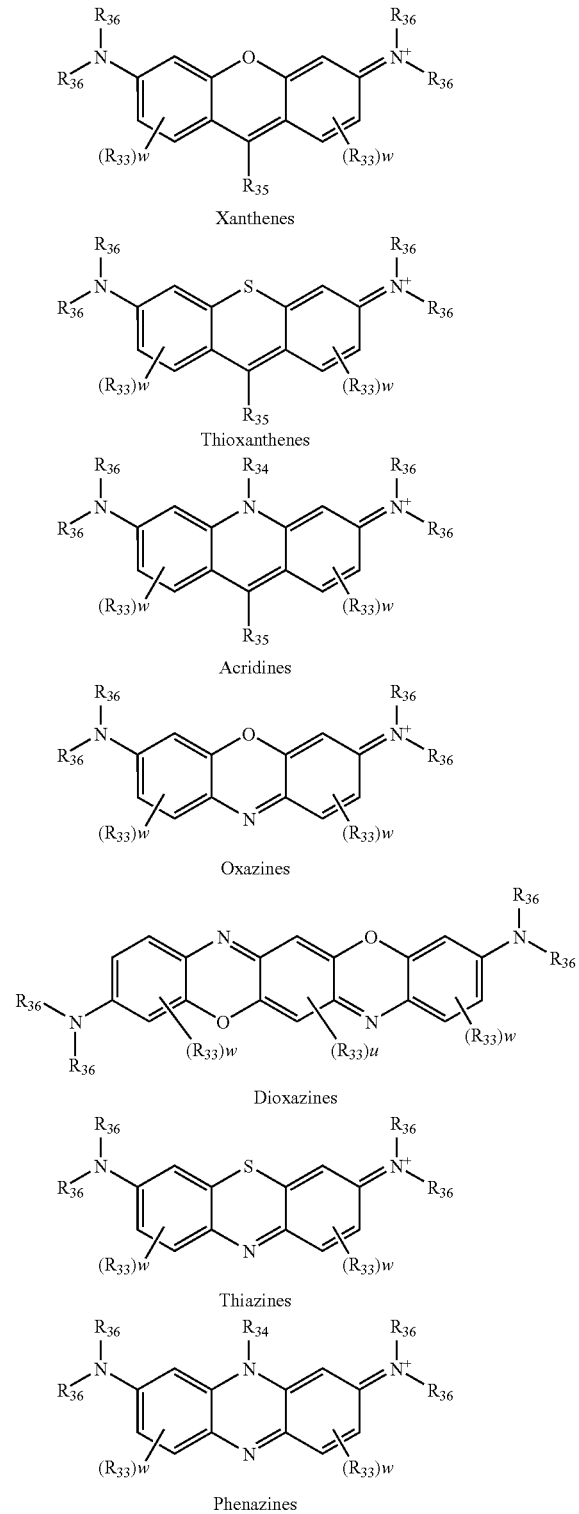

Xanthenes

Thioxanthenes

Acridines

Oxazines

Dioxazines

Thiazines

Phenazines wherein the radicals $R_{33}$, $R_{34}$, $R_{35}$ or $R_{36}$ and the coefficients u and w are defined above.

The chromophore is linked to the linker via one of the radicals $R_{33}$, $R_{34}$, $R_{35}$ or $R_{36}$, or via a ring. In this case of linking via a ring, the radical borne by the ring represents a single bond between the chromophore and the linker.

The at least one mixed dye may also comprise at least one chromophore of the family of (hetero)aromatic nitro compounds.

Examples that may be mentioned include the compounds corresponding to formulae (XIII) and (XIV) below, and also the tautomeric forms thereof:

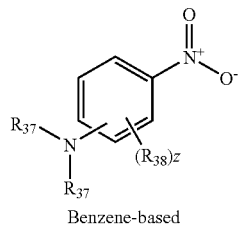

Benzene-based

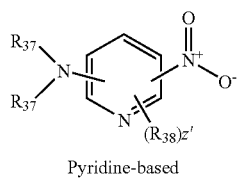

Pyridine-based wherein $R_{37}$, which may be identical or different, is chosen from a hydrogen atom; linear and branched $C_1$-$C_8$ alkyl radicals, optionally bearing at least one hydroxyl group; an optionally substituted aryl radical, a ($C_1$-$C_8$)alkylaryl radical, wherein the aryl portion is optionally substituted; linear and branched, optionally substituted $C_1$-$C_8$ alkyl radicals, and linear and branched, optionally substituted $C_1$-$C_8$ alkoxy radicals;

$R_{38}$, which may be identical or different, is chosen from a hydrogen atom; linear and branched, optionally substituted $C_1$-$C_4$ alkyl radicals; linear and branched, optionally substituted $C_1$-$C_8$ alkoxy radicals; an optionally substituted $C_6$ aryl radical; an amino radical; an amino radical substituted with at least one radical chosen from linear and branched $C_1$-$C_8$ such as $C_1$-$C_4$ alkyl radicals, which may be identical or different, which are optionally substituted, for example, with at least one hydroxyl group, linear and branched $C_1$-$C_4$ alkoxy radicals, linear and branched $C_1$-$C_4$ thioalkyl group, and linear and branched $C_1$-$C_4$ alkylsulfonamido groups; optionally substituted $C_6$ aryl radicals; optionally substituted 5- to 6-membered heteroaryl radicals; a hydroxyl group; a nitro group; and a cyano group; wherein the coefficient z is equal to 4 and the coefficient z' is equal to 3.

In addition, the chromophore is linked to the linker via $R_{37}$ or $R_{38}$, or via the ring. In the case of linking via a ring, the radical borne by the ring represents a single bond between the chromophore and the linker.

Thus, as examples of the mixed dyes comprising two chromophores mention may be made of the following mixed dyes:
azo-linker-azine,
azo-linker-methine,
azo-linker-carbonyl,
azo-linker-nitro,
azo-linker-tri(hetero)arylmethane,
tri(hetero)arylmethane-linker-azine,
tri(hetero)arylmethane-linker-methine,
tri(hetero)arylmethane-linker-carbonyl,
tri(hetero)arylmethane-linker-nitro, and
tri(hetero)arylmethane-linker-tri(hetero)arylmethane.

As mentioned previously, the chromophores of the mixed dye are linked together via at least one linker that stops delocalization of the electrons of each of the chromophores.

Thus, the at least one linker comprises at least one atom that isolates each of the chromophores of the mixed dye.

For example, the bond between the radical and the linker is made via a nitrogen or oxygen atom.

The linker may be cationic or non-cationic.

Furthermore, the linker may be divalent, trivalent or tetravalent.

In one embodiment, the linker is chosen from linear and branched $C_1$-$C_{20}$ such as $C_1$-$C_{12}$ hydrocarbon-based chains, for example, an alkyl chain, wherein at least one of the carbon atoms of the chain is possibly replaced with a hetero atom such as sulfur, nitrogen and oxygen atoms, provided that the chain does not comprise two adjacent hetero atoms; or with a saturated or unsaturated 5- or 6-membered heterocycle such as comprising at least two nitrogen atoms; wherein the hydrocarbon-based chains are possibly unsaturated or comprise an arylene radical. The linker may also be chosen from an arylene radical; a divalent terephthalamide radical; and a divalent or trivalent radical, for example, of triazine type.

For example, the linker is chosen from linear and branched $C_1$-$C_{20}$ such as $C_1$-$C_{12}$ alkyl chains, at least one of the carbon atoms of which may be replaced with a saturated or unsaturated 5- or 6-membered heterocycle, such as comprising at least two nitrogen atoms.

The mixed dyes as disclosed herein may be prepared according to chemical reactions that are known per se, starting with functionalized chromophores capable of reacting with the chosen linker.

For example, when the linker is a triazine group, then the chromophore comprises at least one reactive group chosen from amino, OH and SH groups, and the synthesis is performed, for example, according to the schemes below:

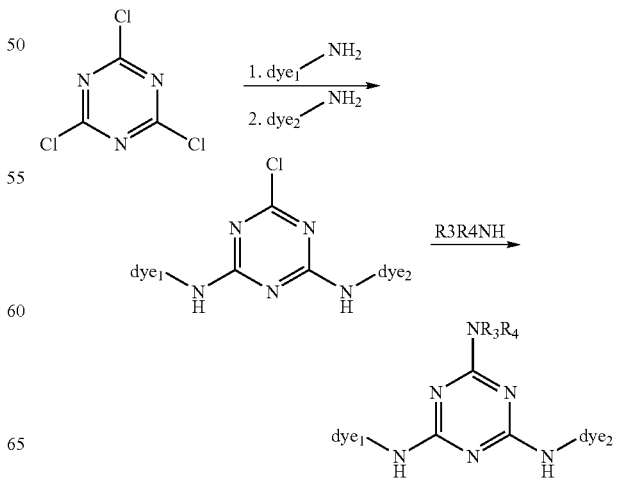

-continued

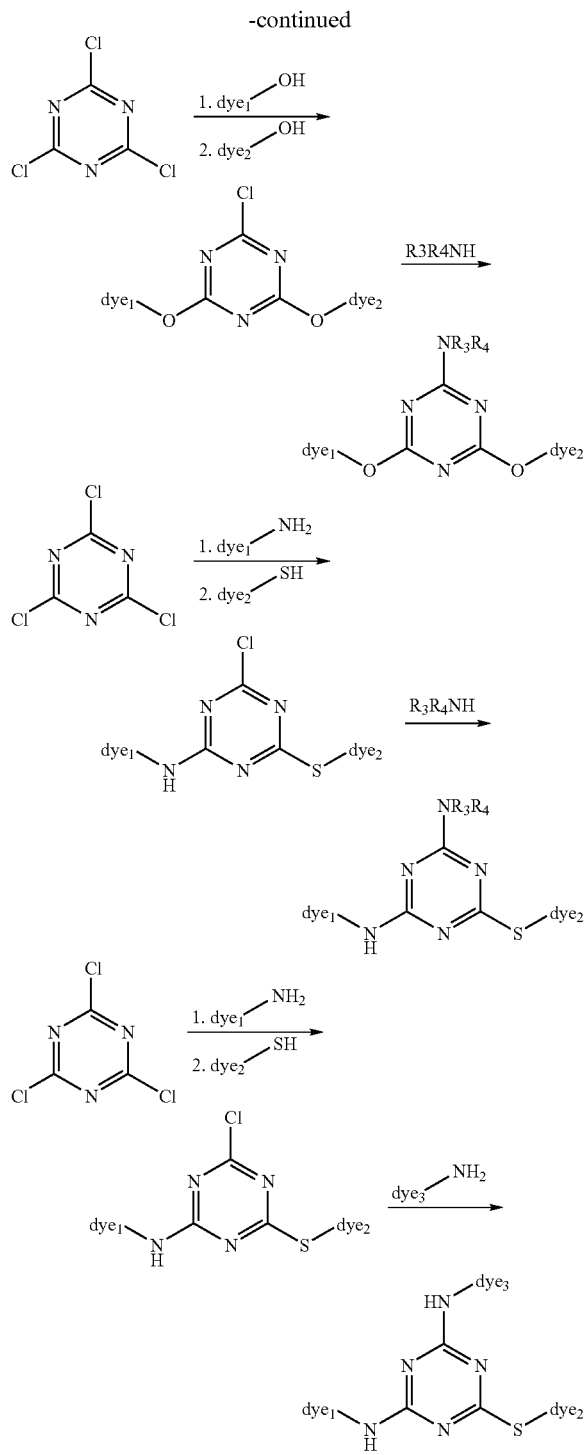

According to a first reaction, a first chromophore is mixed with the compound capable of forming the linker, for example, trichlorotriazine. When this reaction is complete, a second chromophore is added to the reaction medium. This sequence may be repeated as many times as there are reactive groups on the compound capable of forming the linker.

For the preparation of a mixed dye Dye 1-linker-Dye 2, the molar ratio of the linker relative to Dye 1 generally ranges from 0.5:1 to 10:1 such as equal to 1:1. This ratio may be modified when more than one linker or several chromophores are used.

The reaction temperature generally ranges from −100° C. to +130° C. such as from −5° C. to 100° C. The reaction time depends on the reactivity of the species present and the reaction temperature. In general, the reaction time ranges from 10 minutes to 8 hours such as from 30 minutes to 4 hours.

For example, the pH of the reaction mixture ranges from 2 to 12.

The reaction may also be performed in water and/or in one or more organic solvents.

Several publications describe the reaction for the chemical combination between two identical chromophores. Examples that may be mentioned include the documents ISBN 0901956759, WO 02/78596, DE 198 45 640 and U.S. Pat. No. 5,708,151.

In addition, the reactions or the reactions of a linker with two different compounds, which may or may not be dyes, have been described in the literature, for example in WO 03/029359, DE 3 335 956, WO 03/30909, WO 03/18021, Journal of Medicinal Chemistry 43(9), 2000, 1892-97; Chemiker Zeitung 117(7-8), 1987, 241-5.

According to another possibility, the mixed dye may be obtained according to the following reaction scheme:

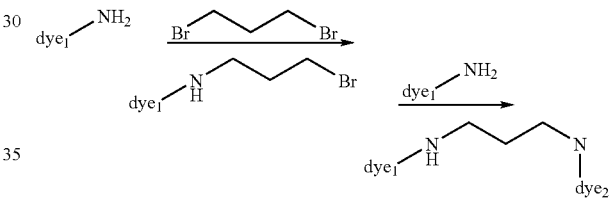

According to a first reaction, a first chromophore is mixed with the compound capable of forming the linker, for example, dibromopropane. When this reaction is complete, a second chromophore is added to the reaction medium. This sequence may be repeated as many times as there are reactive groups on the compound capable of forming the linker.

For the preparation of a mixed dye Dye 1-linker-Dye 2, the molar ratio of the linker relative to Dye 1 generally ranges from 0.1:1 to 10:1, such as equal to 0.5:1. This ratio may be modified when more than one linker or several chromophores are used.

The reaction temperature generally ranges from −100° C. to +30° C. such as from −5° C. to 100° C. The reaction time depends on the reactivity of the species present and the reaction temperature. In general, the reaction time ranges from 10 minutes to 24 hours such as from 30 minutes to 4 hours.

The reaction may be performed in water and/or in one or more organic solvents.

For example, the pH of the reaction mixture ranges from 2 to 12.

The composition as disclosed herein usually comprises the at least one mixed dye in an amount ranging, for example, from 0.001% to 20% by weight, such as from 0.005% to 10% by weight and further such as from 0.01% to 5% by weight, relative to the total weight of the composition.

In one embodiment, the dye composition disclosed herein does not comprise any mixed dye chosen from the following compounds:

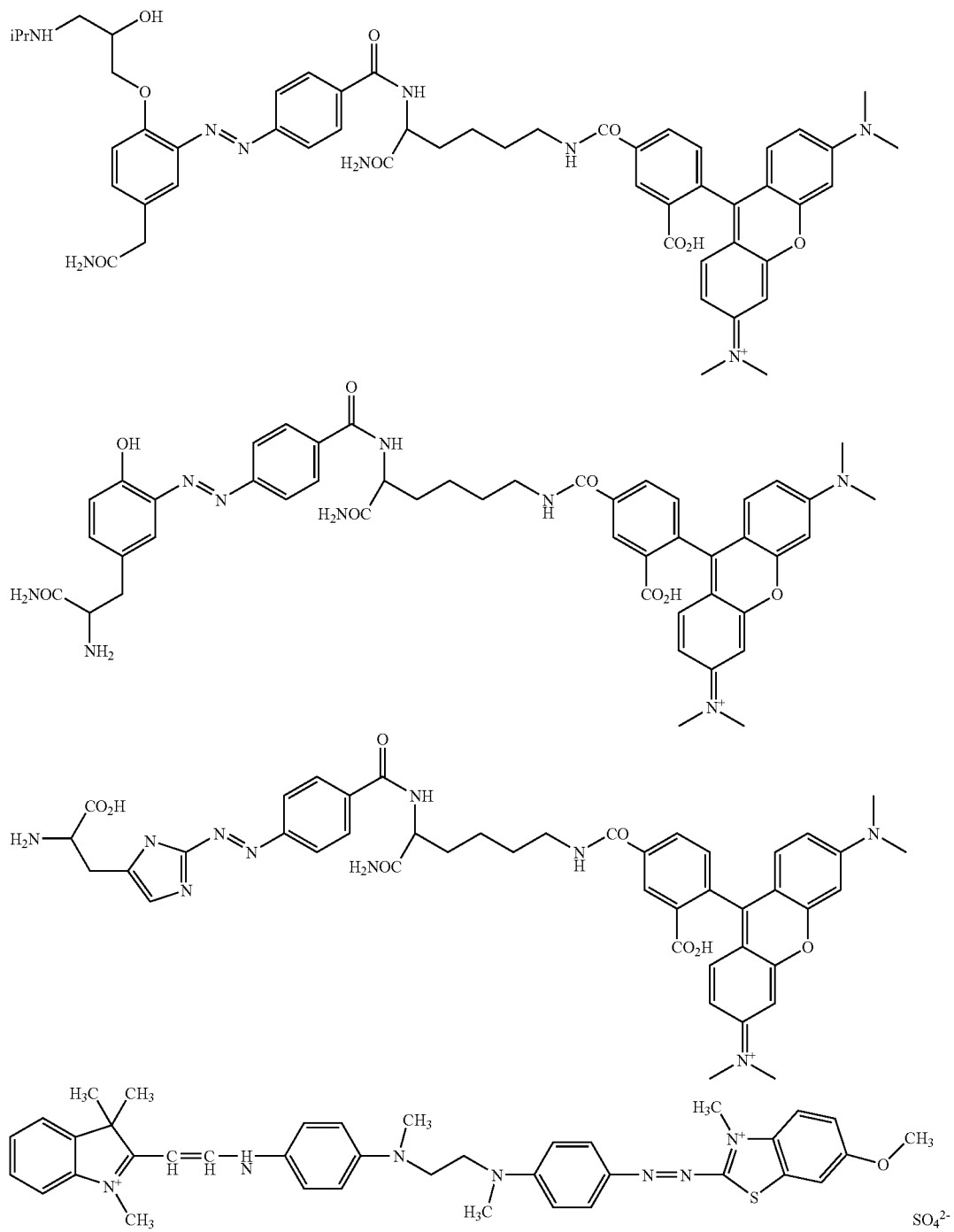

The dye composition as disclosed herein may comprise at least one additional direct dye other than the mixed dye described hereinabove.

The direct dyes conventionally used in the field of dyeing keratin fibers, such as human keratin fibers, may be used.

In this respect, mention may be made, for example, of nitrobenzene dyes, azo direct dyes and methine direct dyes.

These direct dyes may be of nonionic, anionic or cationic nature. In one embodiment, these additional direct dyes are of cationic nature.

In one embodiment, the dye composition comprises at least one direct dye in an amount ranging from 0.001% to 10% by weight relative to the total weight of the dye composition.

The dye composition as disclosed herein may also comprise at least one dye ingredient chosen from oxidation bases and couplers conventionally used for dyeing keratin fibers, such as human keratin fibers.

Among the oxidation bases that may be mentioned, examples include para-phenylenediamines, bis(phenyl)alkylenediamines, para-aminophenols, ortho-aminophenols and heterocyclicbases, and the addition salts thereof.

The at least one oxidation base may be present in the composition disclosed herein in an amount ranging, for example, from 0.001% to 10% by weight, such as from 0.005% to 6% by weight, relative to the total weight of the dye composition.

Among the couplers that may be used, mention may be made, for example, of meta-phenylenediamines, meta-aminophenols, meta-diphenols, naphthalene-based couplers and heterocyclic couplers, and the addition salts thereof.

In the composition disclosed herein, the at least one coupler is present in an amount ranging, for example, from 0.001% to 10% by weight such as from 0.005% to 6% by weight relative to the total weight of the dye composition.

In general, the addition salts, for example, of the oxidation bases and the couplers that may be used herein are chosen, for example, from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines and alkanolamines.

The medium suitable for dyeing, also known as the dye support, is a cosmetic medium that generally comprises water or a mixture of water and at least one organic solvent to dissolve the compounds that would not be sufficiently soluble in water.

Examples of organic solvents that may be mentioned include linear or branched such as saturated monoalcohols comprising from 2 to 10 carbon atoms, such as ethanol and isopropanol; aromatic alcohols such as benzyl alcohol and phenylethyl alcohol; polyols or polyol ethers, for instance ethylene glycol monomethyl, monoethyl or monobutyl ether, propylene glycol or ethers thereof, for instance propylene glycol monomethyl ether, butylene glycol, dipropylene glycol, hexylene glycol (2-methyl-2,4-pentanediol), neopentyl glycol and 3-methyl-1,5-pentanediol; and also diethylene glycol alkyl ethers, such as $C_1$-$C_4$ alkyl ethers, for instance diethylene glycol monoethyl ether or monobutyl ether, alone or as a mixture.

The at least one solvent may be present in an amount ranging, for example, from 1% to 40% by weight, such as from 5% to 30% by weight, relative to the total weight of the dye composition.

The dye composition as disclosed herein may also comprise at least one adjuvant chosen from various adjuvants conventionally used in compositions for dyeing keratin fibers, such as human keratin fibers, for example, the hair, such as anionic, cationic, nonionic, amphoteric or zwitterionic surfactants or mixtures thereof; anionic, cationic, nonionic, amphoteric or zwitterionic polymers or mixtures thereof; mineral or organic thickeners, and for example, anionic, cationic, nonionic and amphoteric associative polymeric thickeners; antioxidants; penetrating agents; sequestering agents; fragrances; buffers; dispersants; conditioning agents, for instance volatile or non-volatile, modified or unmodified silicones; film-forming agents; ceramides, pseudoceramides; preserving agents; opacifiers, etc.

The at least one adjuvant may be present in an amount ranging, for example, from 0.01% to 20% by weight relative to the weight of the composition.

The composition disclosed herein may also comprise at least one oxidizing agent.

The oxidizing agents conventionally used for the oxidation dyeing of keratin fibers such as human keratin fibres include, for example, hydrogen peroxide, urea peroxide, alkali metal bromates or ferricyanides, persalts such as perborates and persulfates of alkali metals or of alkaline-earth metals, such as sodium, potassium or magnesium, alone or as mixtures, peracids and oxidase enzymes, among which mention may be made, for example, of peroxidases, two-electron oxidoreductases such as uricases, and four-electron oxygenases, for instance laccases. In one embodiment, hydrogen peroxide is used.

The composition disclosed herein may furthermore comprise at least one alkaline agent, which may be chosen from those conventionally used in cosmetics.

Among these alkaline agents, examples that may be mentioned include aqueous ammonia, alkaline carbonates, alkanolamines such as monoethanolamine, diethanolamine and triethanolamine, and also derivatives thereof, sodium hydroxide, potassium hydroxide and the compounds of formula (A) below:

wherein W is a propylene residue optionally substituted with a hydroxyl group or a $C_1$-$C_4$ alkyl radical; $R_a$, $R_b$, $R_c$ and $R_d$, which may be identical or different, are each chosen from a hydrogen atom and $C_1$-$C_4$ alkyl and $C_1$-$C_4$ hydroxyalkyl radicals.

The pH of the dye composition disclosed herein ranges, for example, from 8 to 11.

A person skilled in the art will take care to select this or these optional additional compound(s) such that the advantageous properties intrinsically associated with the composition disclosed herein are not, or are not substantially, adversely affected by the envisaged addition(s).

The dye composition disclosed herein may be in various forms, such as in the form of liquids, creams or gels, or in any other form that is suitable for dyeing keratin fibers, such as human keratin fibres, for example, the hair.

The process disclosed herein is a process comprising applying the composition as defined above to the wet or dry fibers.

In a first embodiment, the composition applied to the keratin fibers does not comprise any oxidizing agent. This embodiment is suitable, for example, when the dye composition comprises at least one mixed dye as disclosed herein and optionally at least one additional direct dye.

According to a second embodiment, the process is performed with at least one oxidizing agent. This embodiment is suitable irrespective of the nature of the dyes present (mixed dye, additional direct dye, oxidation bases and/or couplers). Such a process allows lightening of the treated fiber to be obtained.

According to this second embodiment, the at least one oxidizing agent may be added to the dye composition at the time of use, or it may be used starting with an oxidizing composition comprising it, which is applied simultaneously with or sequentially to the dye composition comprising the mixed dye. In this latter case, the at least one oxidizing agent is present in a composition different from the one comprising the mixed dye.

For example, the composition comprising the mixed dye is mixed, such as at the time of use, with a composition comprising, in a medium suitable for dyeing, at least one oxidizing agent, wherein this at least one oxidizing agent is present in an amount sufficient to obtain the desired lightening.

The mixture obtained is then applied to the keratin fibers.

After an action time that is sufficient to obtain the desired coloration, usually ranging from 3 to 50 minutes such as from 5 to 30 minutes, the keratin fibers are, for example, rinsed, and then washed with shampoo, rinsed again and then dried or left to dry.

Moreover, the composition is conventionally left to act at a temperature ranging from 15 to 80° C. such as from 15 to 40° C.

The oxidizing composition may also comprise at least one adjuvant chosen from various adjuvants conventionally used in compositions for dyeing keratin fibers, such as human keratin fibers, and as defined above.

The pH of the oxidizing composition comprising the at least one oxidizing agent is such that, after mixing with the dye composition, the pH of the resulting composition applied to the keratin fibers (i.e., the ready-to-use composition) ranges, for example, from 7 to 12 such as from 8 to 11. It may be adjusted to the desired value by acidifying or basifying agents.

Among the acidifying agents, examples that may be mentioned include mineral or organic acids, for instance hydrochloric acid, orthophosphoric acid, sulfuric acid and acetic acid.

Among the basifying compounds, reference may be made to the list given above.

The ready-to-use composition, i.e., the composition that is finally applied to the keratin fibers, may be in various forms, such as in the form of liquids, creams or gels, or in any other form that is suitable for dyeing keratin fibers, for example, human keratin fibers such as the hair.

Further disclosed herein is also a multi-compartment device, which comprises at least one first compartment comprising a dye composition comprising the at least one mixed dye as described above, and optionally at least one direct dye different from the mixed dye, optionally at least one oxidation base, optionally at least one coupler, and at least one second compartment comprising at least one oxidizing agent.

The at least one mixed dye, optionally the at least one additional direct dye, the at least one oxidation base and the at least one coupler may be in the same compartment or in several compartments, wherein the same compartment may comprise only one type of dye (mixed dye, additional direct dye or oxidation dye) or a combination of several of these dyes.

This device may be equipped with an applicator for applying the desired mixture to the fibers to be treated, such as the devices described in French patent FR 2586913.

Further disclosed herein is the mixed dye as described above, and also addition salts thereof, with the exception of the following four compounds:

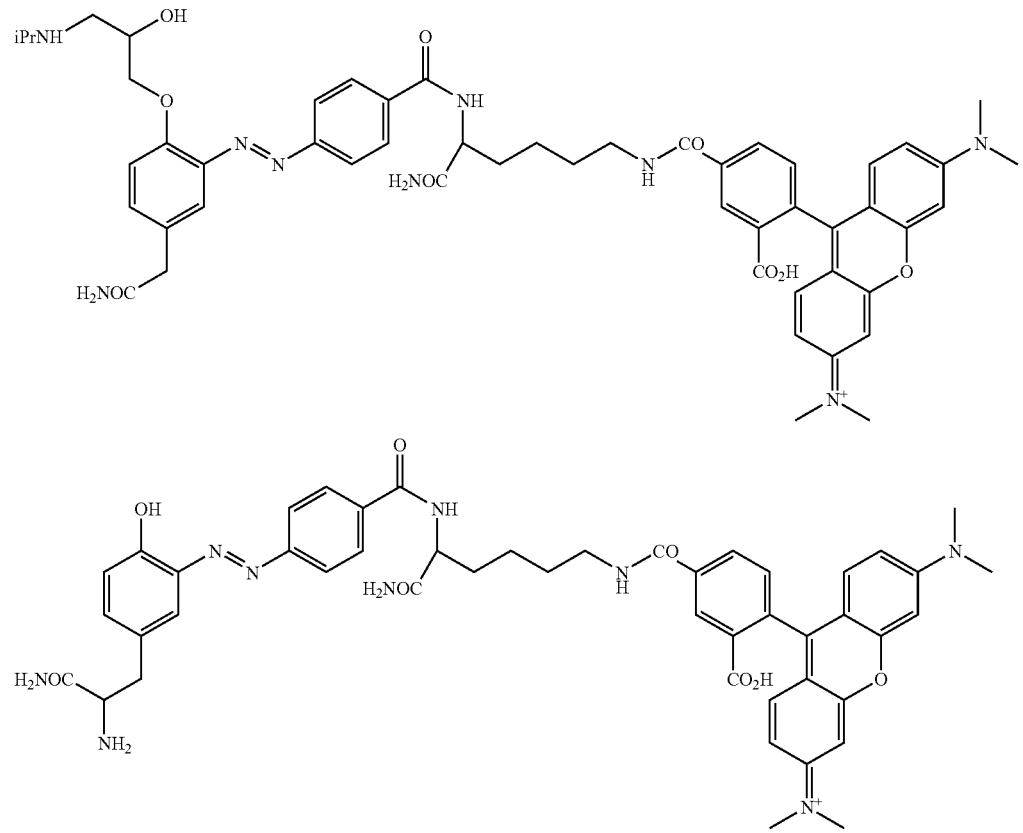

-continued

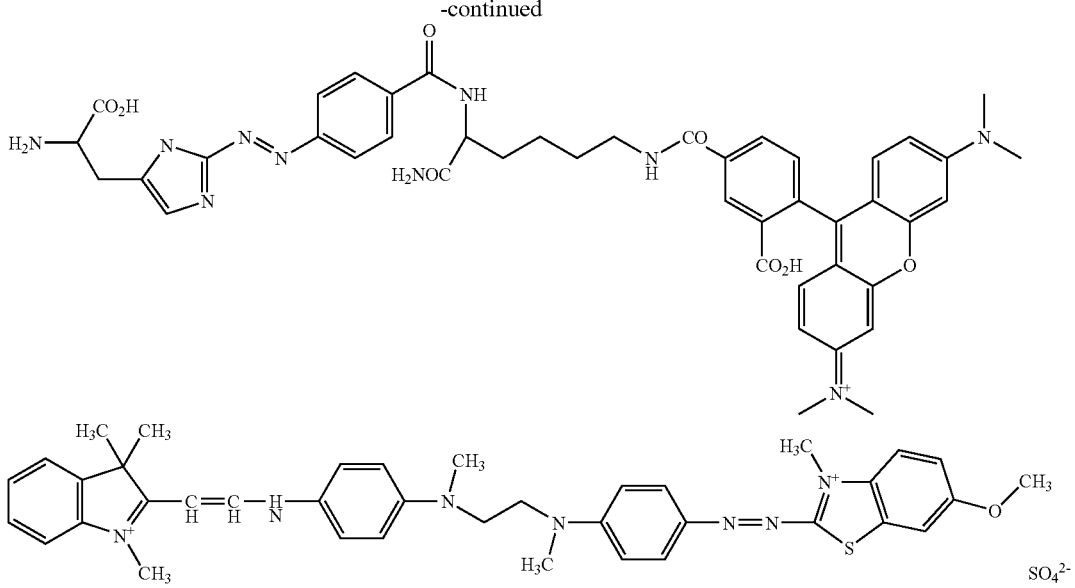

For example, the present disclosure relates to mixed dyes comprising two chromophores. In one embodiment, at least one of the two chromophores bears at least one cationic charge, for example, both chromophores bear at least one cationic charge. Moreover, in one embodiment, at least one of the chromophores is chosen from chromophores of the azo family, and the other is chosen from the dye family such as diazacarbocyanin or isomers thereof, hemicyanin or nitro (hetero)aromatics. Furthermore, for example, the linker is chosen from linear and branched $C_1$-$C_{20}$ such as $C_1$-$C_{12}$ alkyl chains, at least one of the carbon atoms of which may be replaced with a saturated or unsaturated 5- or 6-membered heterocycle, such as comprising at least two nitrogen atoms. The linker may optionally bear at least one cationic charge.

Examples of such mixed dyes that may be mentioned include those of the following formulae:

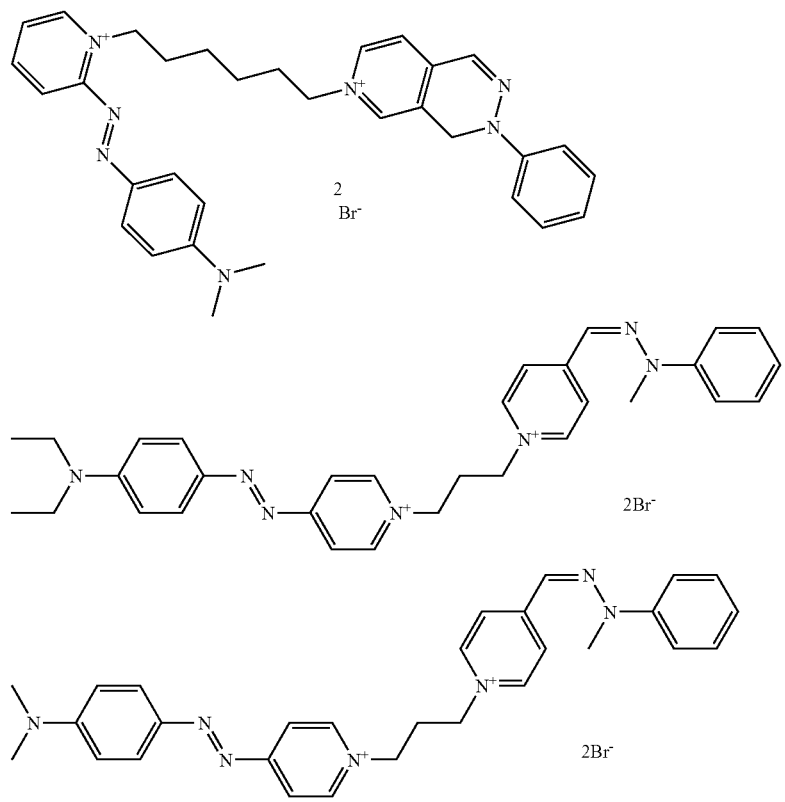

-continued
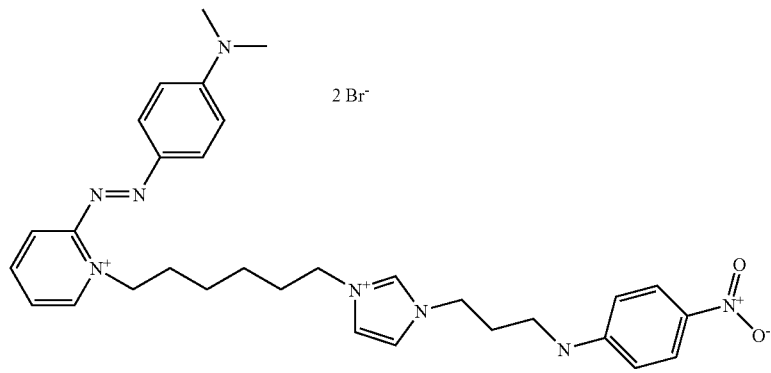
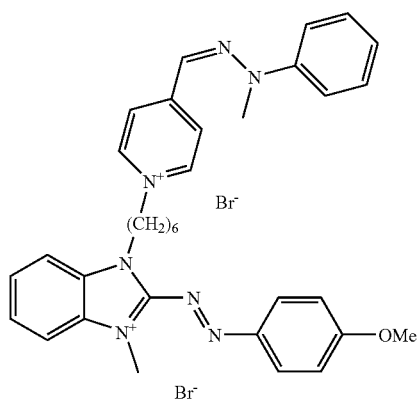
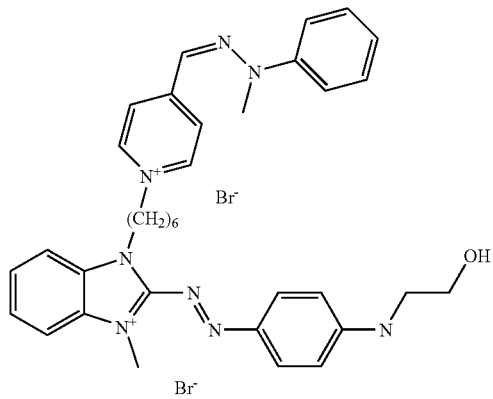
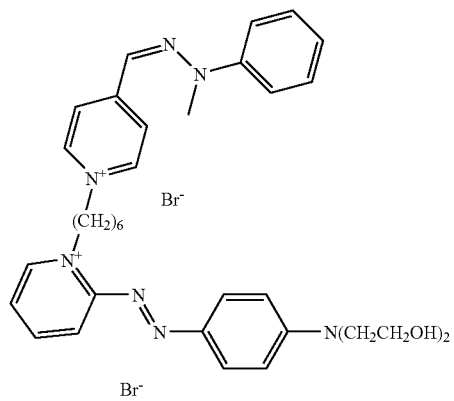

-continued
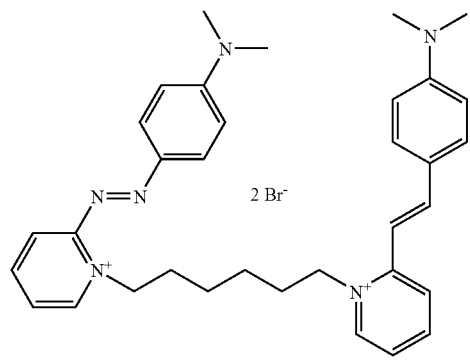
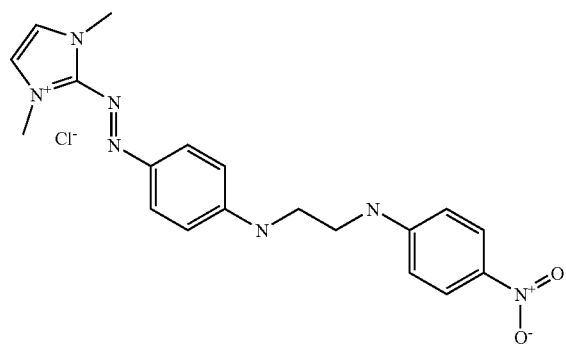
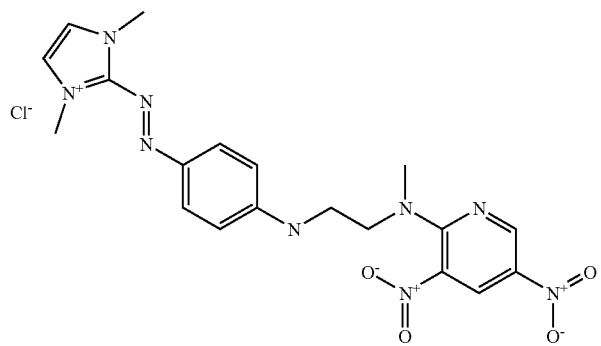
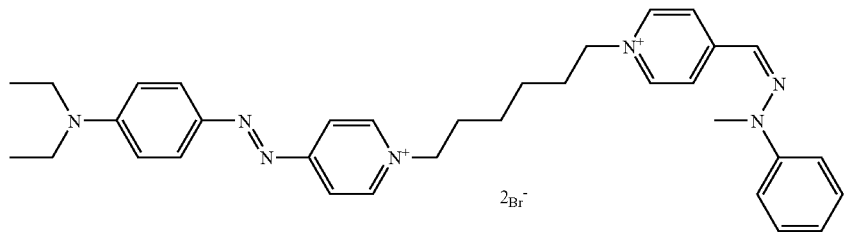
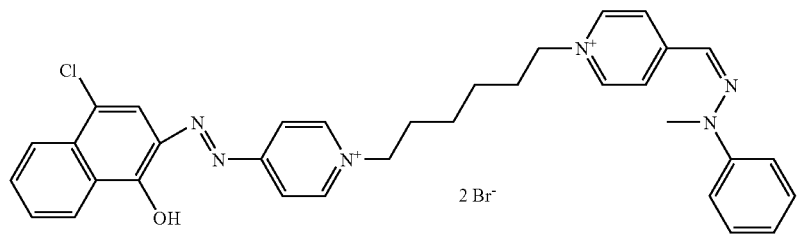

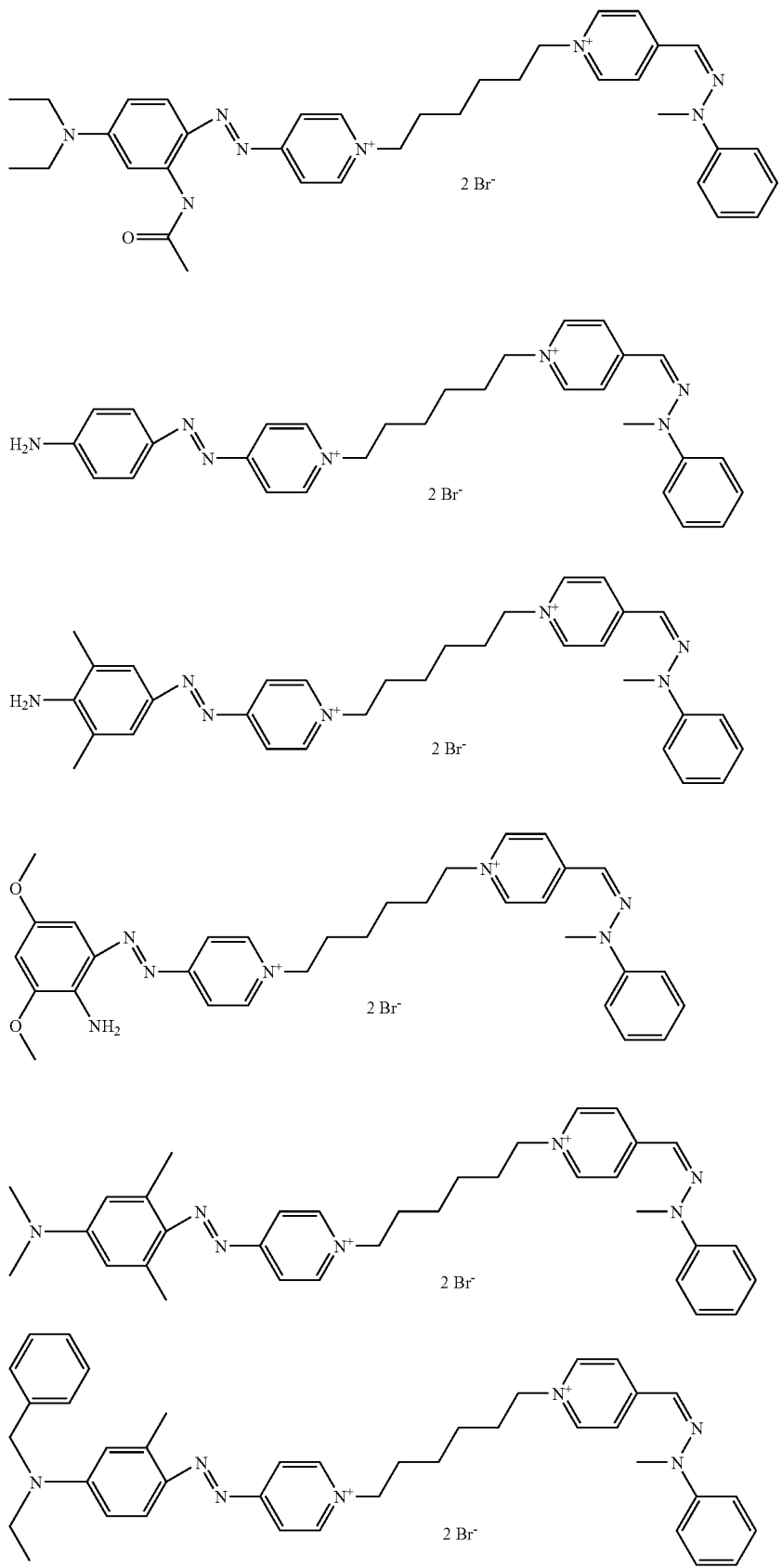

-continued

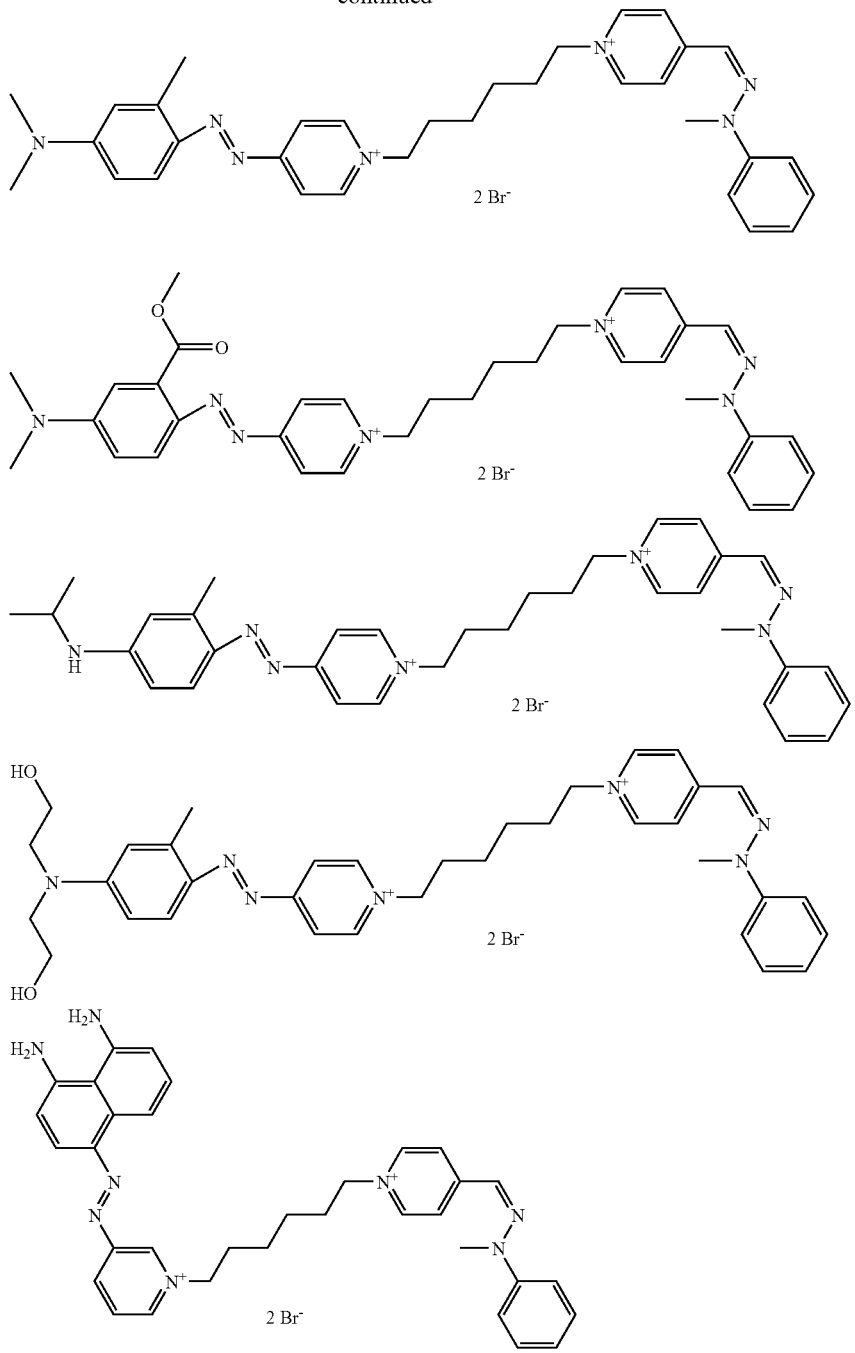

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Concrete, but in no way limiting, examples illustrating the invention are as follows.

EXAMPLE 1

Synthesis of the Mixed Dye

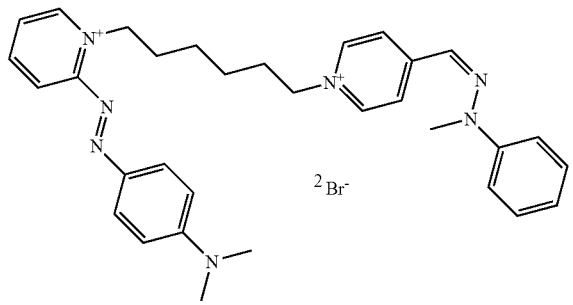

Reaction Scheme:

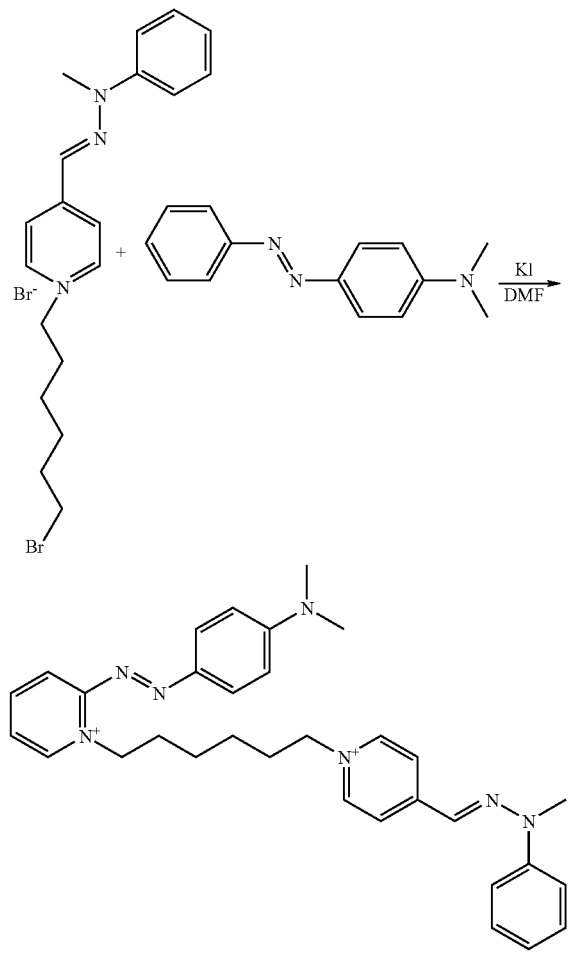

Process:

1.06 equivalents of the hydrazone dye (3 g) and 100 mg of KI were placed in 2 ml of DMF in a three-necked flask with stirring, and the mixture was heated to 95° C.

1 equivalent of the azo dye (1.49 g) dissolved in 5 ml of DMF were then added and the mixture was reacted for 24 hours.

The product was recovered by precipitation from ethyl acetate (50 ml), filtered off and dried; the product was in the form of a black powder.

The product was purified by dissolution in dichloromethane followed by precipitation in an isopropanol/ethyl acetate mixture (1/4), and was then filtered off.

The $^{13}$C and $^{1}$H NMR spectra were in accordance with the structure of the expected product.

Dyeing Applications

1. Lightening and Non-Lightening Dyeing

The mixed dye obtained in Example 1 was formulated at $4.7 \times 10^{-4}$ mol % in the dye composition A below:

| Composition A | |
|---|---|
| (50/50 $C_8/C_{10}$) alkyl polyglucoside as a buffered aqueous 60% solution | 10 g |
| Benzyl alcohol | 10 g |
| Polyethylene glycol 400 comprising 8 ethylene oxide units | 12 g |
| Mixed dye | $4.7 \times 10^{-4}$ mol |
| 20.5% aqueous ammonia | 13 g |
| Demineralized water | qs 100 g |

At the time of use, composition A was mixed either with 40 V aqueous hydrogen peroxide solution (weight for weight, pH=3.5) or with acidified water (pH=3.5).

The pH of the dye compositions after mixing ranged from 9.5 to 10.

The mixture was then applied to locks of natural grey hair (NG) or permanent-waved grey hair (PWG) comprising 90% white hairs.

The action time on the lock was 20 minutes at room temperature.

The locks were then washed with shampoo.

Dyed locks were obtained in both cases.

2. Shampoo-fastness

A dye composition according to the present disclosure was prepared using the mixed dye ($4.7 \times 10^{-4}$ mol %) and the dye support A.

Separately, a comparative dye composition was prepared, under the same experimental conditions, with the exception that the mixed dye was replaced with an equimolar mixture of the two monocationic monoazo direct dyes constituting the mixed dye.

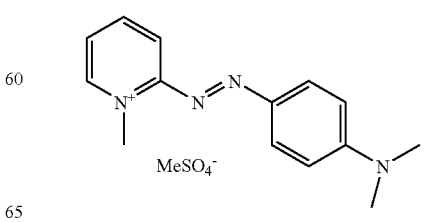

Violet Dye

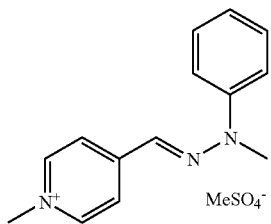

Yellow Dye

At the time of use, the above compositions were mixed with 40 V aqueous hydrogen peroxide solution (weight for weight, pH=3.5).

The pH of the dye compositions after mixing ranged from 9.5 to 10.

The mixtures were then applied to locks of permanent-waved grey hair (PWG) comprising 90% white hairs.

The action time on the locks was 20 minutes at room temperature.

The dyed locks were then shampooed six times, with intermediate drying between two shampoo washes.

The color after the six shampoo washes was compared with the initial color of the dyed lock, visually and by colorimetric measurement.

The shampoo fastness was measured on dyed permanent-waved hair according to the ΔE formula below, using the L*a*b* values measured on each type of lock before $L_0{}^*a_0{}^*b_0{}^*$ and after $L_1{}^*a_1{}^*b_1{}^*$ the six shampoo washes (Minolta CM2002 colorimeter, illuminant D65-10° CSI).

$$\Delta E = \sqrt{(L_1{}^* - L_0{}^*)^2 + (a_1{}^* - a_0{}^*)^2 + (b_1{}^* - b_0{}^*)^2}$$

The colorimetric results are shown in Table 2.

TABLE 2

| Type of hair | L* | a* | b* | Degradation |
|---|---|---|---|---|
| Composition according to the invention: | | | | |
| PWG/before shampooing | 22.9 | 15.0 | 3.9 | 2.1 |
| PWG/after shampooing | 24.7 | 16.1 | 3.9 | |
| Comparative composition: | | | | |
| PWG/before shampooing | 24.5 | 18.2 | 6.4 | 4.8 |
| PWG/after shampooing | 28.6 | 20.6 | 6.7 | |

These results show that the composition as disclosed herein had good shampoo-fastness.

In addition, its staying power was greater than that of the mixture of dyes in the comparative composition.

EXAMPLE 2

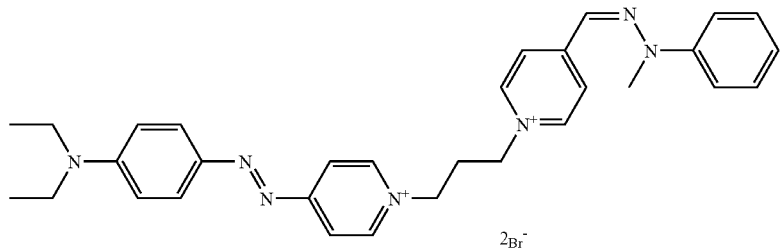

Reaction Scheme:

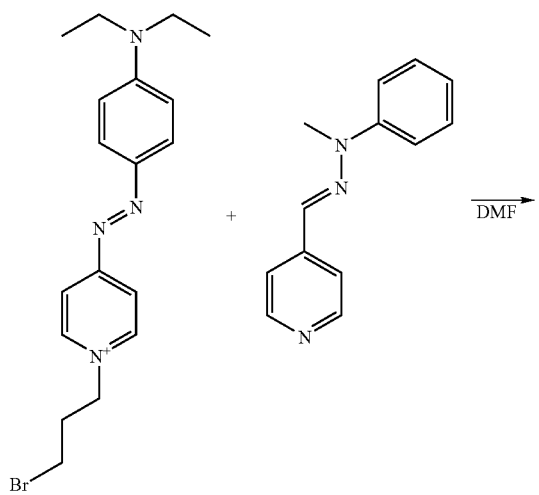

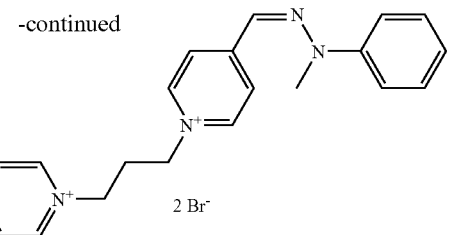

Process:

The azo compound (5 g), 100 ml of DMF and the hydrazone compound (2 g) were introduced into a three-necked flask. The mixture was reacted for 4 hours at 100° C. The product was recovered by precipitation from diisopropyl ether (250 ml). The product was filtered off and dried; it was in the form of a black powder (2 g).

The NMR and mass spectra were in accordance with the structure of the expected product.

The use of a dye composition of the same type as those described in Example 1, but comprising the dye obtained in this example, made it possible to obtain dyed locks.

EXAMPLE 3

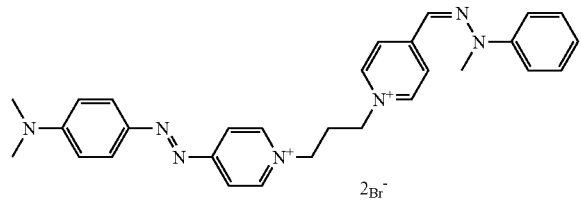

Reaction Scheme:

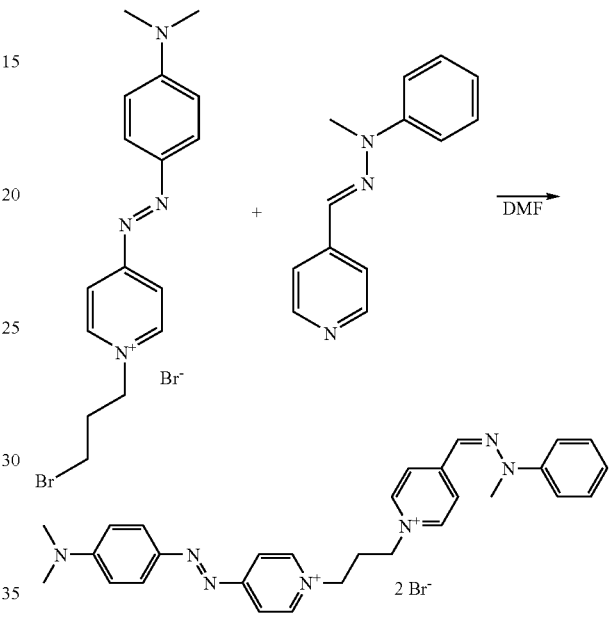

Process:

The hydrazone compound (98 mg), 10 ml of DMF and the azo compound (200 mg) were introduced into a three-necked flask. The mixture was reacted for 4 hours at 100° C. The product was recovered by precipitation from ethyl acetate (100 ml). The product was filtered off and dried; it was in the form of a black powder (200 mg).

The NMR and mass spectra were in accordance with the structure of the expected product.

The use of a dye composition of the same type as those described in Example 1, but comprising the dye obtained in this example, made it possible to obtain dyed locks.

EXAMPLE 4

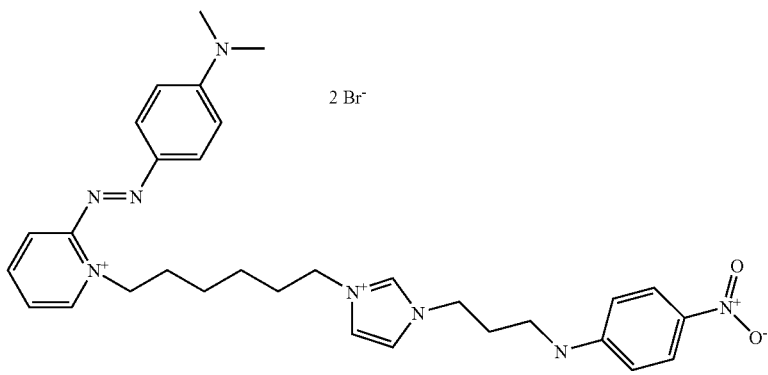

Reaction Scheme:

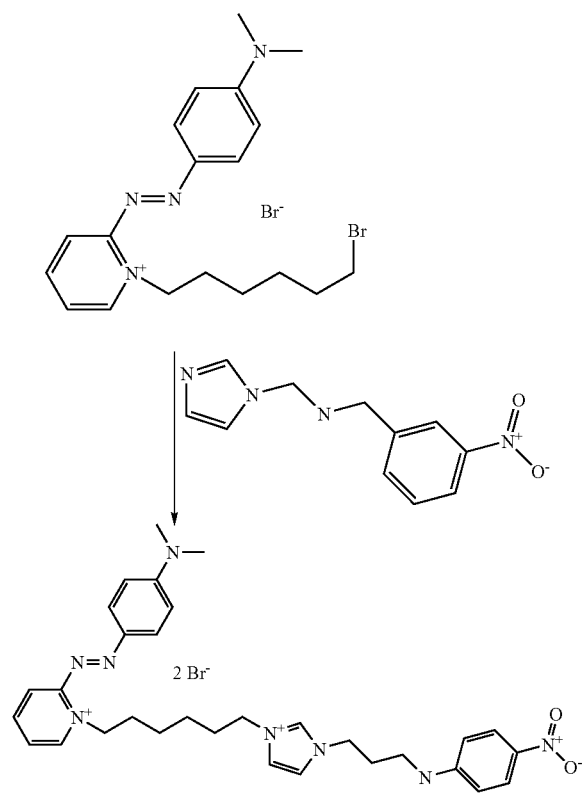

Process:

The nitro compound (3.33 g), 100 ml of DMF and the azo compound (6.16 g) were introduced into a three-necked flask. The mixture was reacted for 4 hours at 100° C. and was then evaporated to dryness.

The product was taken up in diisopropyl ether. It was filtered off and dried under vacuum.

A black powder (6 g) was obtained.

The NMR and mass spectra were in accordance with the structure of the expected product.

The use of a dye composition of the same type as those described in Example 1, but comprising the dye obtained in this example, made it possible to obtain dyed locks.

EXAMPLE 5

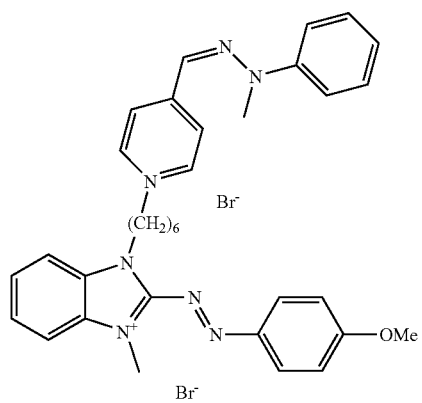

Reaction Scheme:

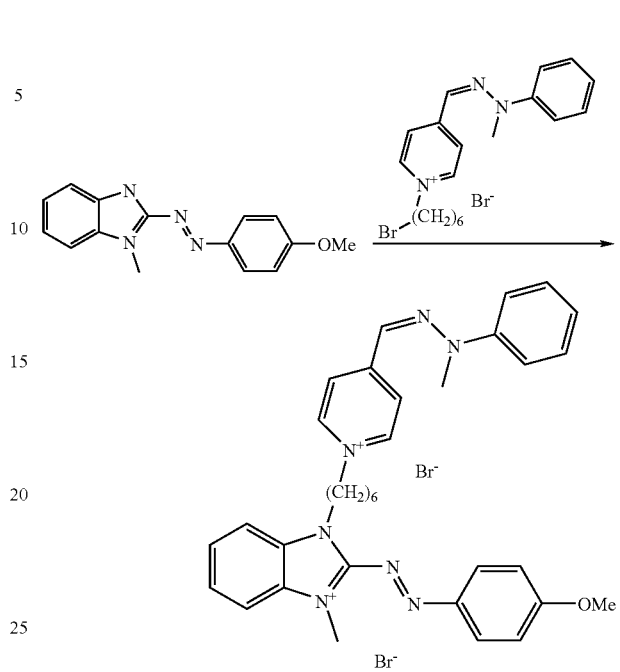

Process:

The azo compound (1.628 g) and the hydrazone compound (2.53 g) were suspended in 10 ml of dry acetonitrile, and 10 mg of potassium iodide and 1 drop of DMF were added.

The reaction mixture was maintained at 60° C. for 3 hours and a fraction of the acetonitrile was then removed by distillation.

The reaction mixture was maintained at 60° C. for a further 14 hours.

After cooling, the product (0.5 g) was isolated by precipitation from acetone.

The NMR and mass spectra were in accordance with the structure of the expected product.

The use of a dye composition of the same type as those described in Example 1, but comprising the dye obtained in this example, made it possible to obtain colored locks.

EXAMPLE 6

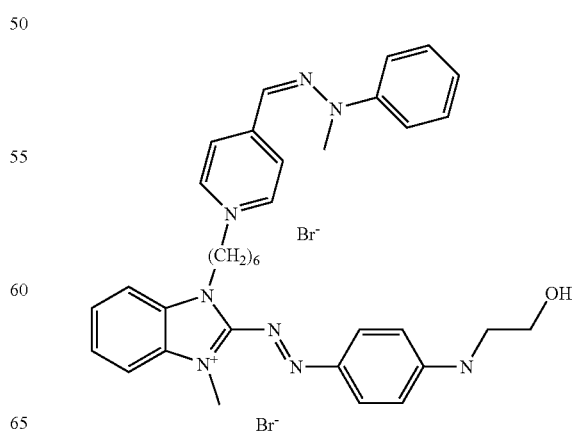

Reaction Scheme:

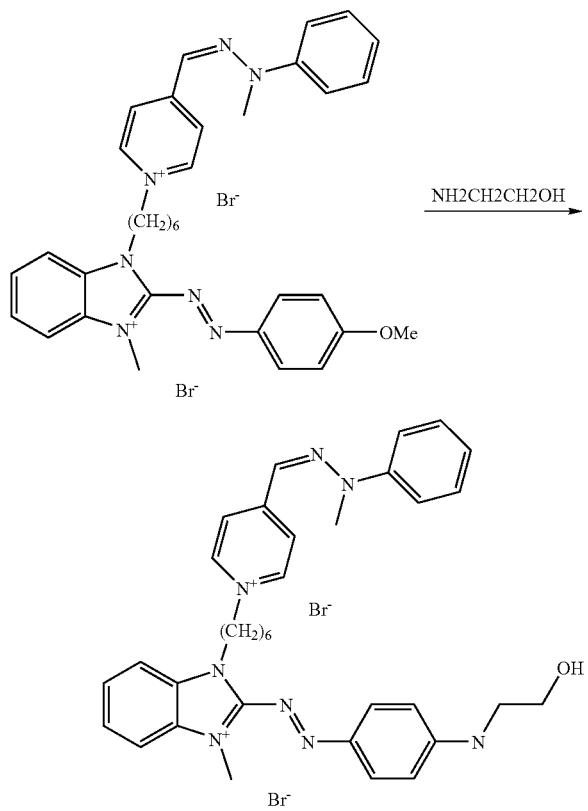

Process:

200 mg of compound obtained in Example 5 were dissolved in 2 ml of methanol, and 1 ml of a solution of methanol containing 17 mg of ethanolamine was then added.

The reaction mixture was maintained at 60° for 1 hour, cooled and diluted in acetone.

A precipitate formed. 110 mg of product were collected after filtration.

The NMR and mass spectra were in accordance with the structure of the expected product.

The use of a dye composition of the same type as those described in Example 1, but comprising the dye obtained in this example, made it possible to obtain colored locks.

EXAMPLE 7

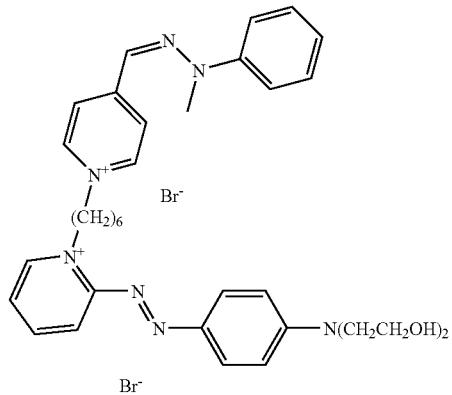

Reaction Scheme:

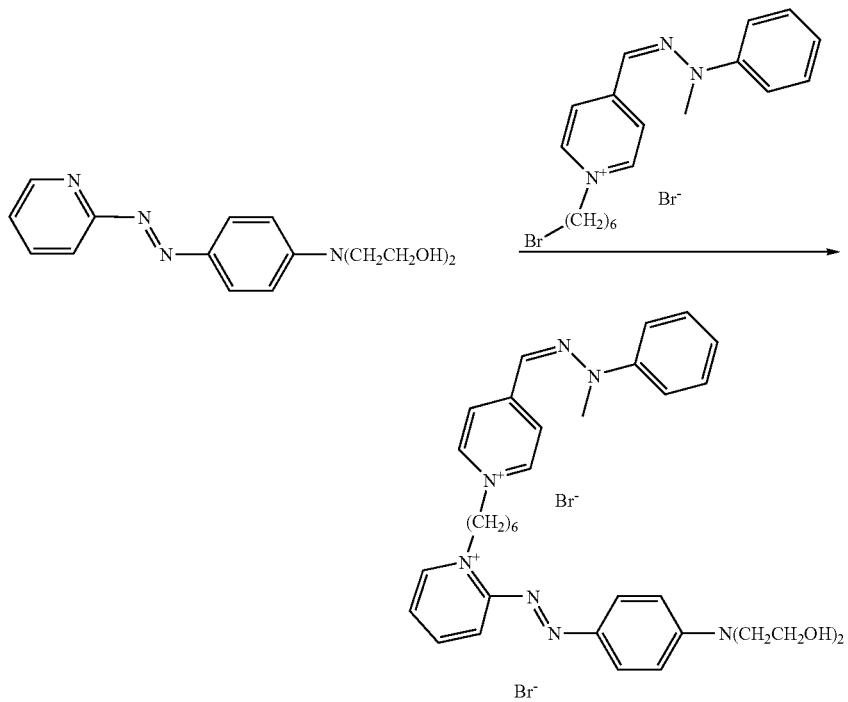

Process:

The azo compound (0.63 g) and the hydrazone compound (1.0 g) were suspended in 10 ml of dry DMF, 224 mg of potassium iodide were added and the reaction mixture was maintained at 80° C. for 18 hours.

The product (0.441 g) was isolated by precipitation from ethyl acetate.

The NMR and mass spectra were in accordance with the structure of the expected product.

The use of a dye composition of the same type as those described in Example 1, but comprising the dye obtained in this example, made it possible to obtain colored locks.

EXAMPLE 8

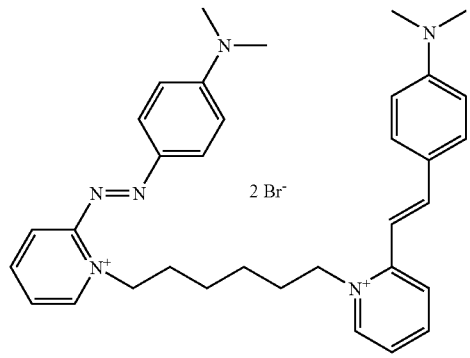

Reaction Scheme:

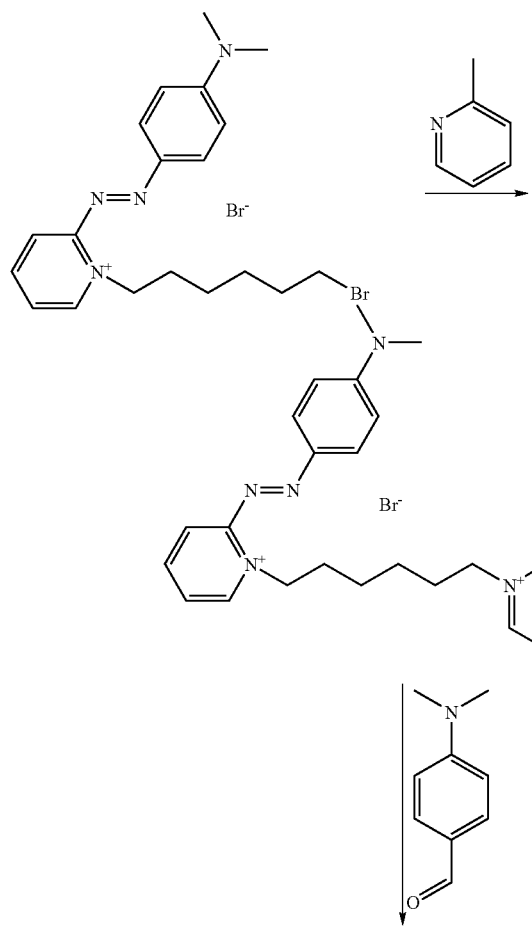

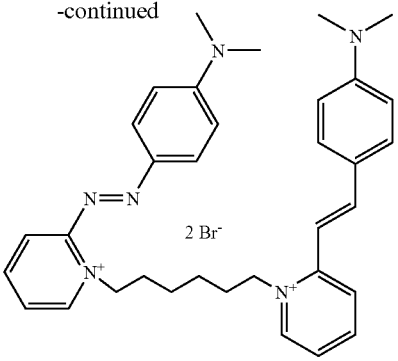

Process:

The azo compound (1.0 g), picoline (2 molar equivalents) and 30 ml of 2-propanol were introduced into a three-necked flask.

The mixture was reacted with stirring for 24 hours at 85° C. and then for 3 days at 92° C. The resulting mixture was evaporated to dryness.

The product was taken up in water and washed with dichloromethane.

The aqueous phase was evaporated to dryness. The powder was taken up in ethyl acetate. The product was filtered off and dried under vacuum.

A black powder (0.566 g) was obtained.

The NMR and mass spectra were in accordance with the structure of the intermediate.

The intermediate obtained (0.25 g), N,N-dimethyl-4-benzaldehyde (0.112 g), pyrrolidine (0.043 ml) and methanol (7 ml) were introduced into a three-necked flask.

The mixture was reacted with stirring for 3 days at room temperature.

The resulting mixture was evaporated to dryness. The residue was washed with diisopropyl ether and then with ethyl acetate.

The resulting residue was dissolved in dichloromethane (10 ml) and the product was precipitated out by addition of a solution of ethyl acetate (90 ml) and 2-propanol (10 ml).

The product was filtered off and dried under vacuum.

A black powder (0.17 g) was obtained.

The NMR and mass spectra were in accordance with the structure of the product.

The use of a dye composition of the same type as those described in Example 1, but comprising the dye obtained in this example, made it possible to obtain colored locks.

EXAMPLE 9

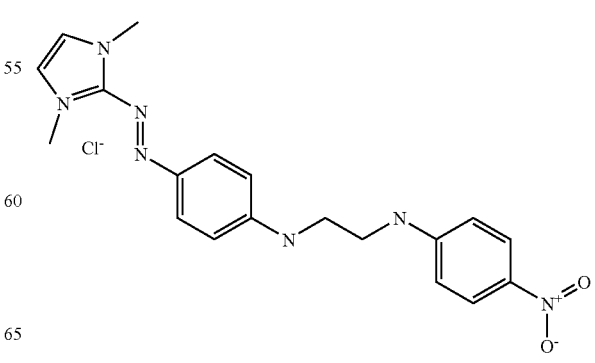

Reaction Scheme:

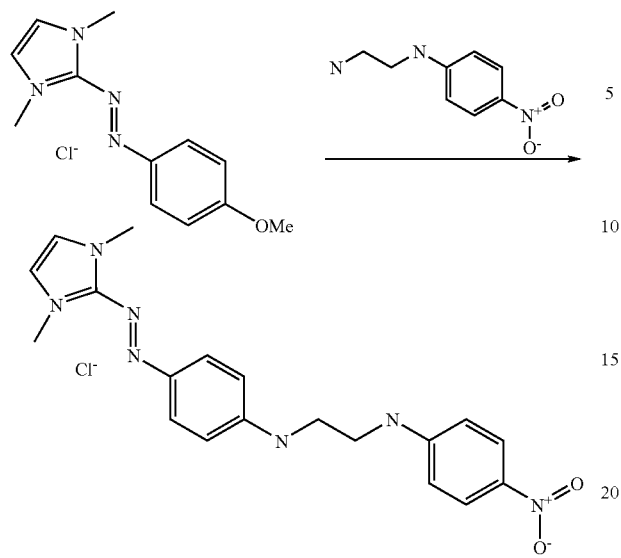

Process:

The azo compound (1.0 g), 7 ml of pentanol and the nitro compound (0.6 g) were introduced into a vial.

The mixture was reacted with stirring for 18 hours at 85° C.

The product was precipitated out by addition of ethyl acetate. The product was filtered off and dried under vacuum.

A black powder (1.3 g) was obtained.

The NMR and mass spectra were in accordance with the structure of the expected product.

The use of a dye composition of the same type as those described in Example 1, but comprising the dye obtained in this example, made it possible to obtain dyed locks.

EXAMPLE 10

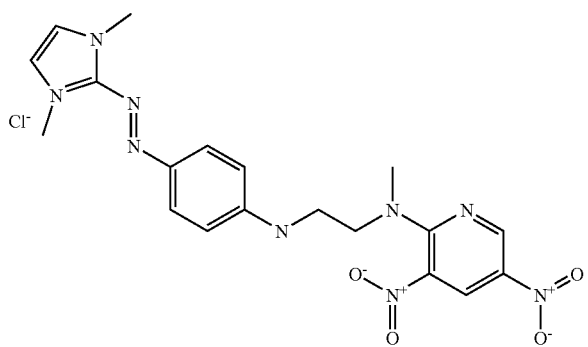

Reaction Scheme:

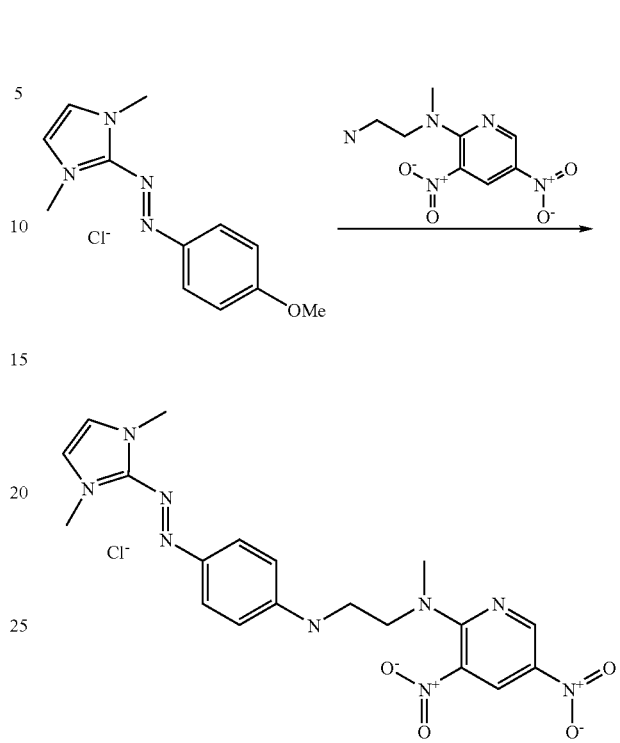

Process:

The azo compound (1.0 g), 7 ml of pentanol and the nitro compound (0.85 g) were introduced into a vial. The mixture was reacted with stirring for 18 hours at 85° C.

The nitro compound (0.42 g) was then added and the mixture was reacted with stirring for 3 hours at 90° C. Finally, the nitro compound (0.85 g) was added.

The mixture was reacted with stirring for 2 days at 90° C.

The product was precipitated out by addition of ethyl acetate. The product was filtered off, washed with ethyl acetate and dried under vacuum.

A black powder (0.84 g) was obtained.

The NMR and mass spectra were in accordance with the structure of the expected product.

The use of a dye composition of the same type as those described in Example 1, but comprising the dye obtained in this example, made it possible to obtain dyed locks.

EXAMPLE 11

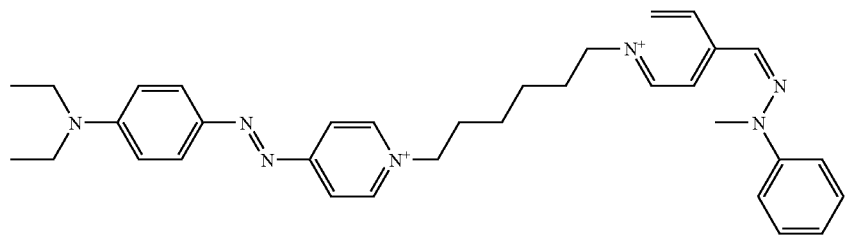

2Br⁻

Reaction Scheme:

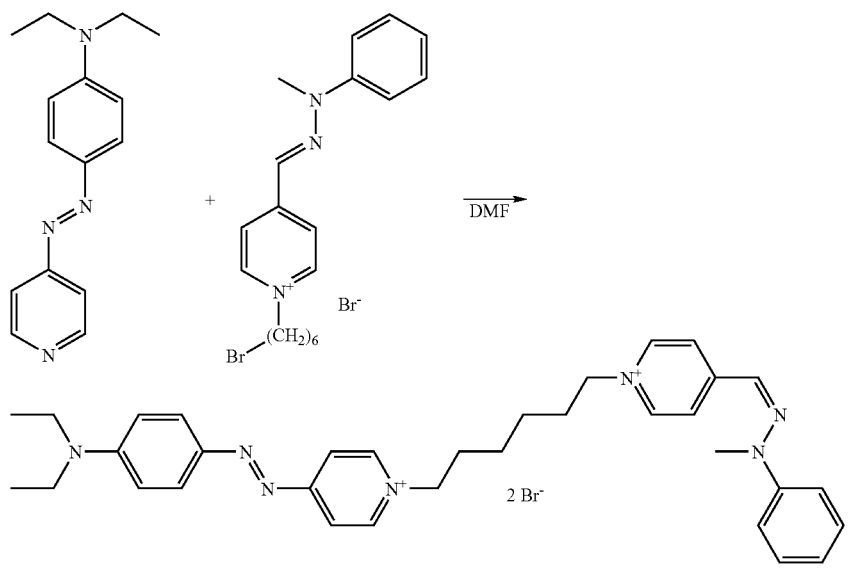

Process:

The azo product (1 g), KI (100 mg) and 5 ml of dimethylformamide (DMF) were introduced into a three-necked flask.

The mixture was stirred and heated for 5 minutes at 90° C.

The hydrazone compound (1.79 g) dissolved in 5 ml of DMF was added. The mixture was reacted with stirring for 16 hours at 90° C.

The product was precipitated from ethyl acetate (250 ml).

The product was filtered off, washed with ethyl acetate and dried under vacuum.

A black powder (2.0 g) was obtained.

The NMR and mass spectra were in accordance with the structure of the expected product.

The use of a dye composition of the same type as those described in Example 1, but comprising the dye obtained in this example, made it possible to obtain dyed locks.

The mixed dyes in Examples 12 to 23 were obtained in accordance with the procedure described in Example 11 by adapting the amounts and by replacing DMF with N-methylpyrrolidone (NMP) or with DMPU.

EXAMPLE 12

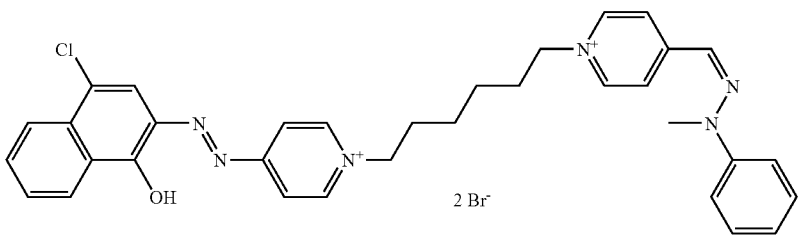

Reaction Scheme:

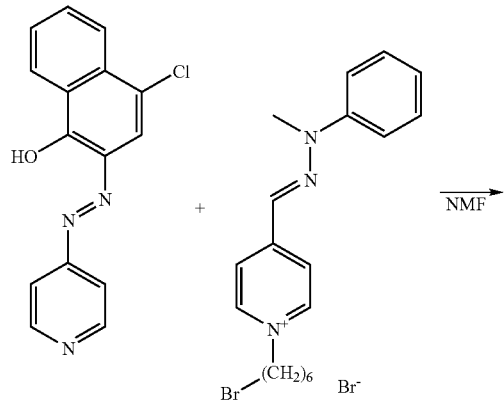

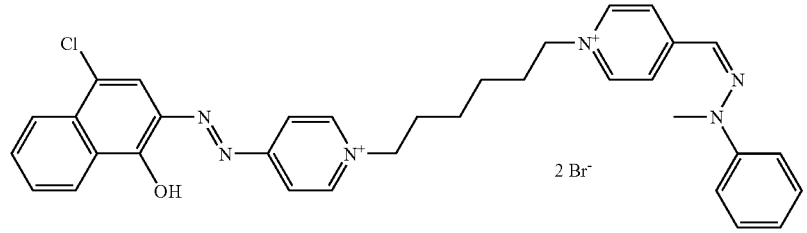
The product structure was confirmed by LC/MS analysis: molecular peak m/z=289; maximum absorption wavelength ($\lambda_{max}$): 420 nm; 566 nm; 250 nm.
EXAMPLE 13
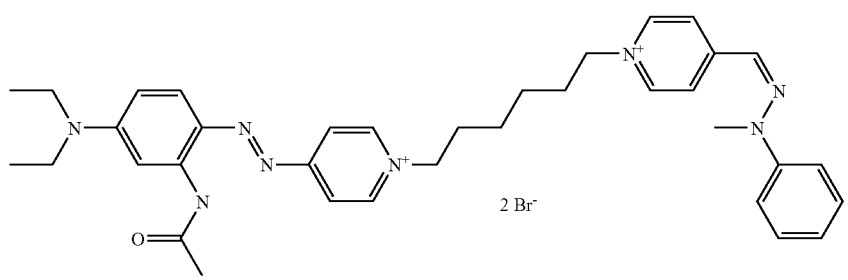
Reaction Scheme:
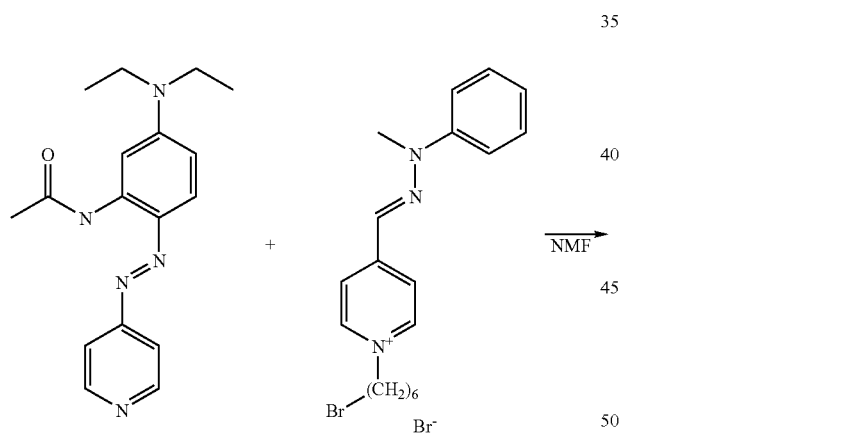
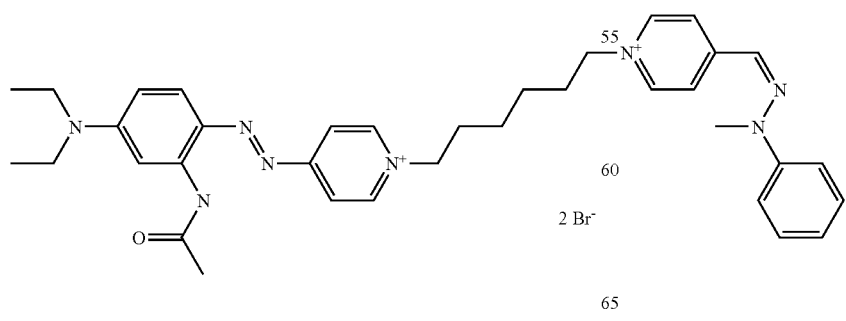

The product structure was confirmed by LC/MS analysis: molecular peak m/z=303; maximum absorption wavelength ($\lambda_{max}$): 566 nm; 420 nm; 252 nm.
EXAMPLE 14
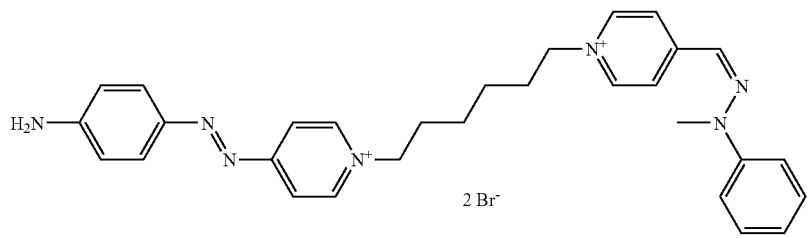
Reaction Scheme:
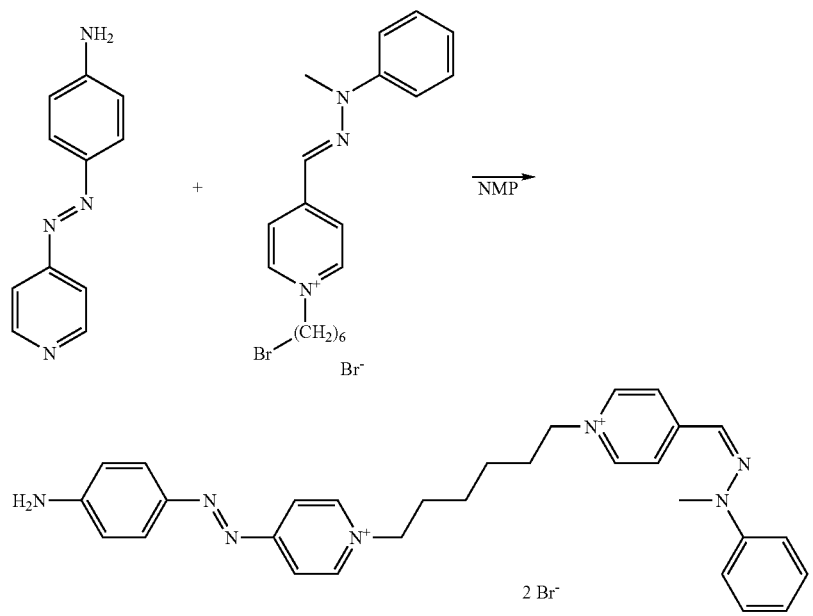
The product structure was confirmed by LC/MS analysis: molecular peak m/z=247; maximum absorption wavelength ($\lambda_{max}$): 424 nm; 518 nm; 258 nm.
EXAMPLE 15
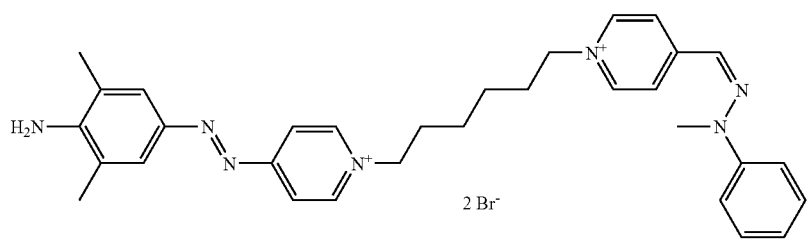

Reaction Scheme:
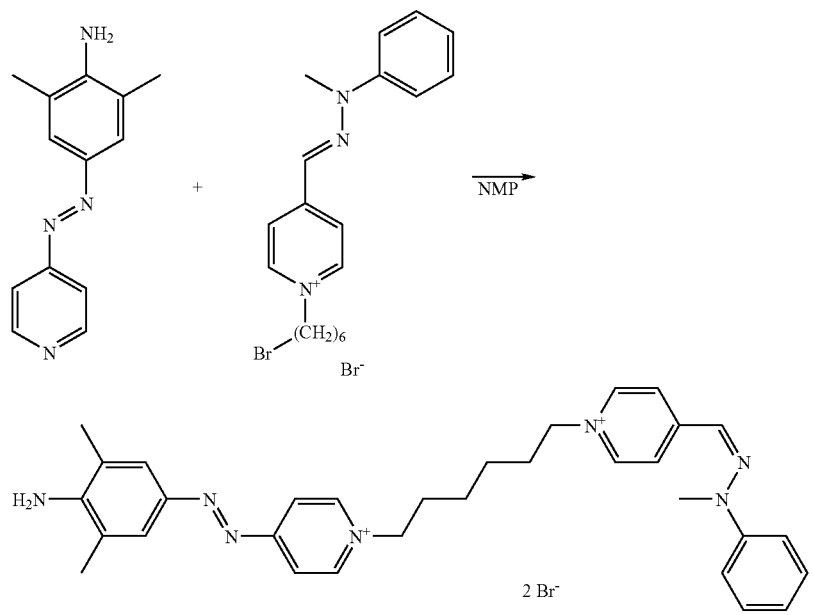
The product structure was confirmed by LC/MS analysis: molecular peak m/z=261; maximum absorption wavelength ($\lambda_{max}$): 422 nm; 538 nm; 256 nm.
EXAMPLE 16
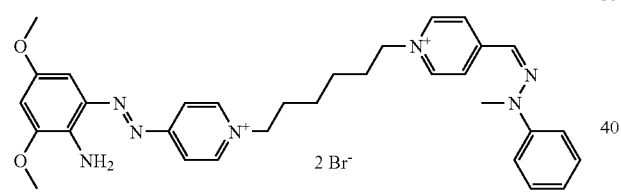
Reaction Scheme:
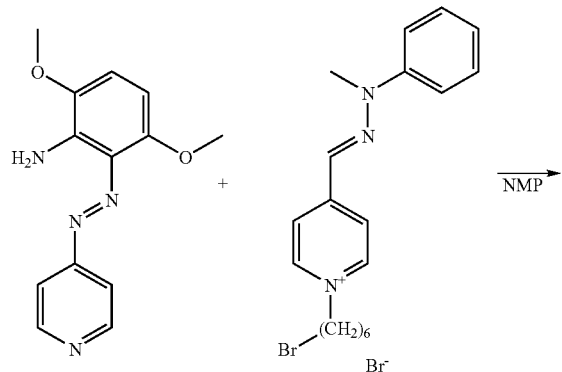

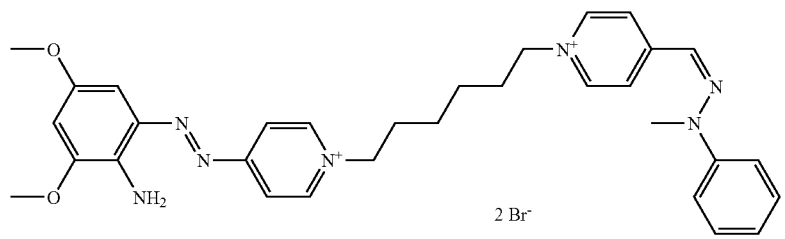
The product structure was confirmed by LC/MS analysis: molecular peak m/z=277; maximum absorption wavelength ($\lambda_{max}$): 558 nm; 416 nm; 254 nm.
EXAMPLE 17
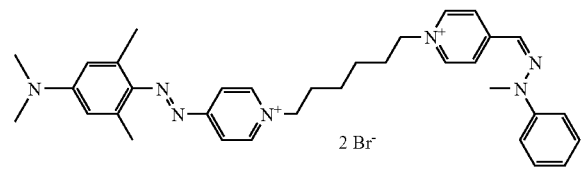
Reaction Scheme:
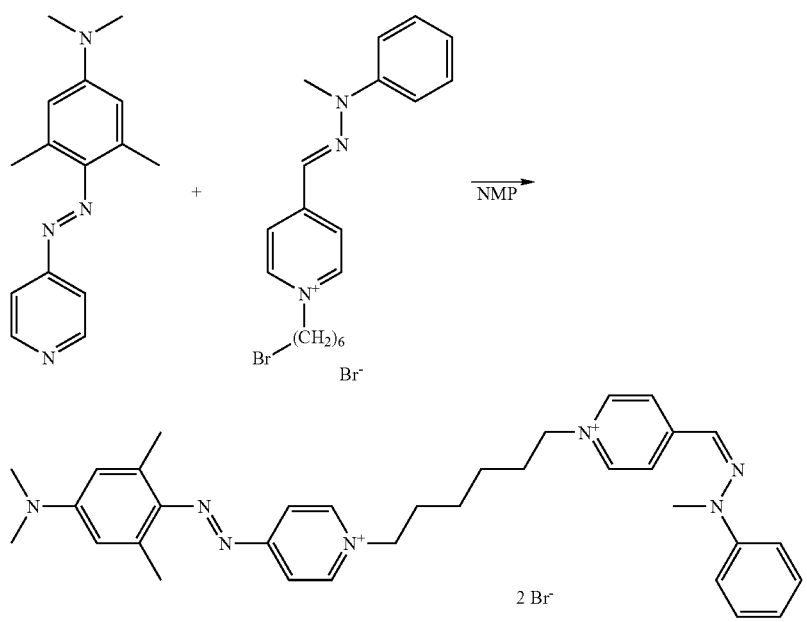
The product structure was confirmed by LC/MS analysis: molecular peak m/z=275; maximum absorption wavelength ($\lambda_{max}$): 418 nm; 552 nm; 256 nm.

EXAMPLE 18
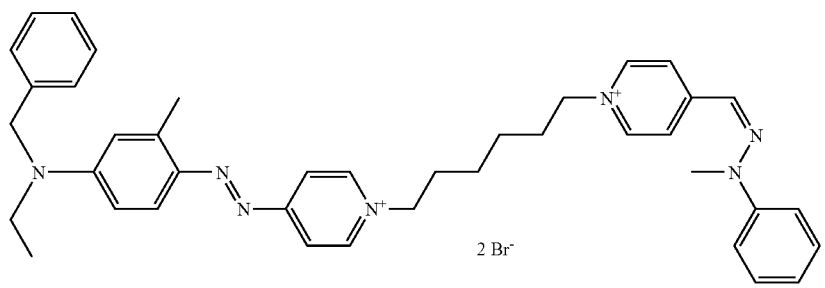
Reaction Scheme:
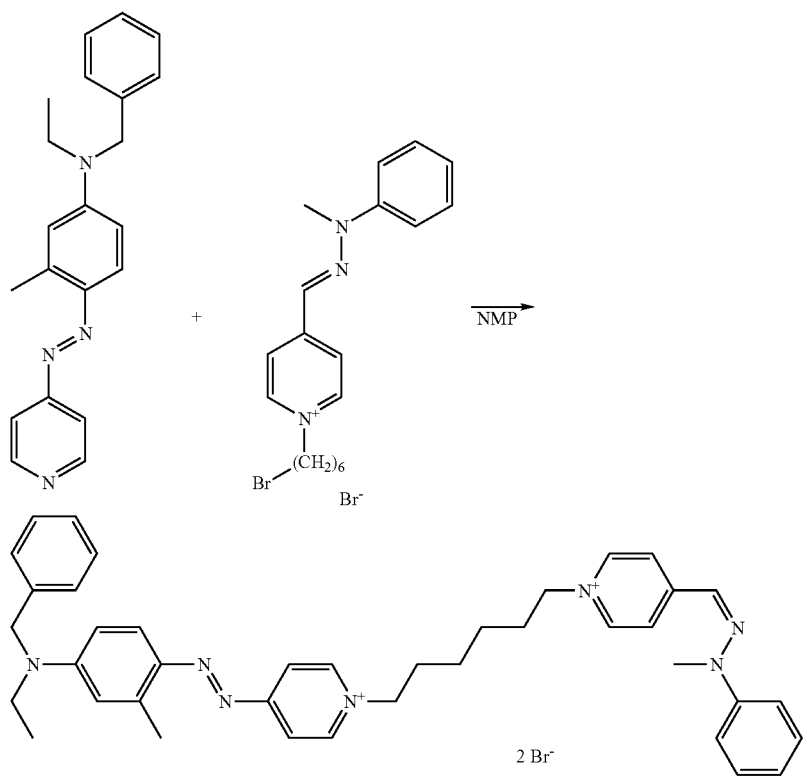
The product structure was confirmed by LC/MS analysis: molecular peak m/z=313; maximum absorption wavelength ($\lambda_{max}$): 418 nm; 568 nm; 256 nm.
EXAMPLE 19
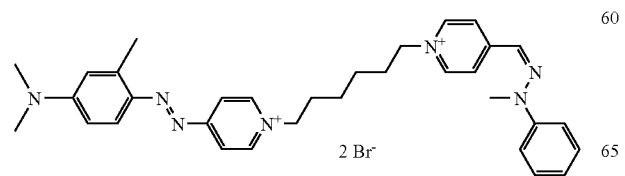

Reaction Scheme:
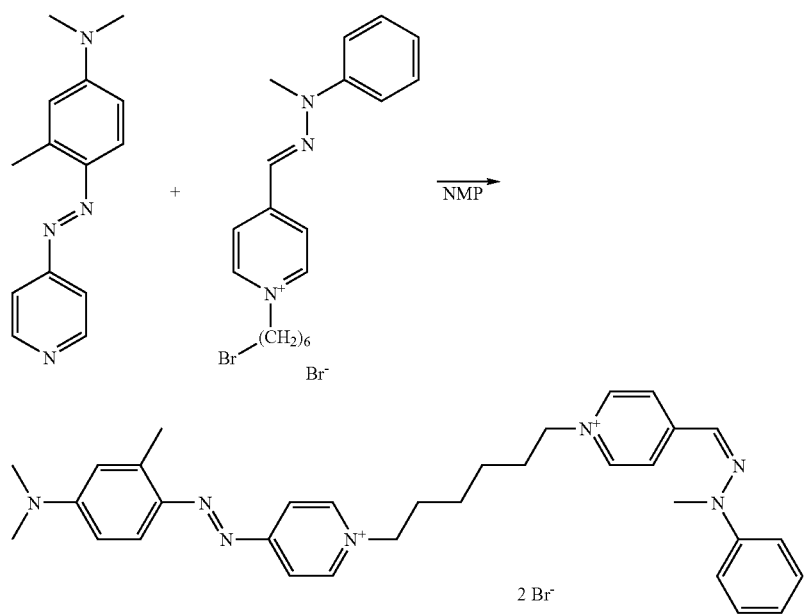
The product structure was confirmed by LC/MS analysis: molecular peak m/z=268; maximum absorption wavelength ($\lambda_{max}$): 574 nm; 420 nm; 256 nm.
EXAMPLE 20
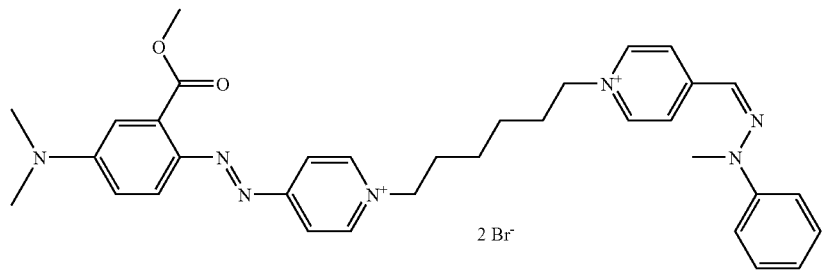
Reaction Scheme:
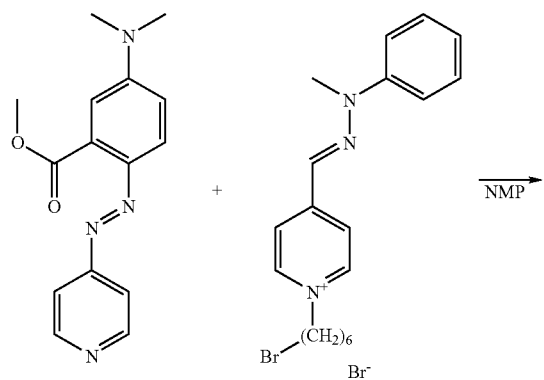

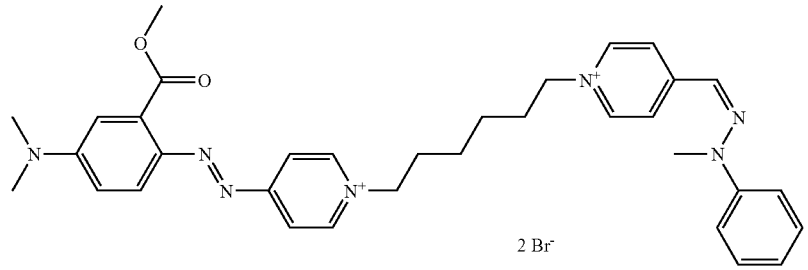
The product structure was confirmed by LC/MS analysis: molecular peak m/z=290; maximum absorption wavelength ($\lambda_{max}$): 556 nm; 420 nm; 254 nm.
EXAMPLE 21
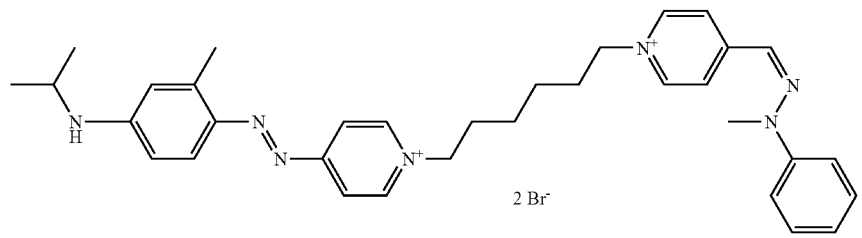
Reaction Scheme:
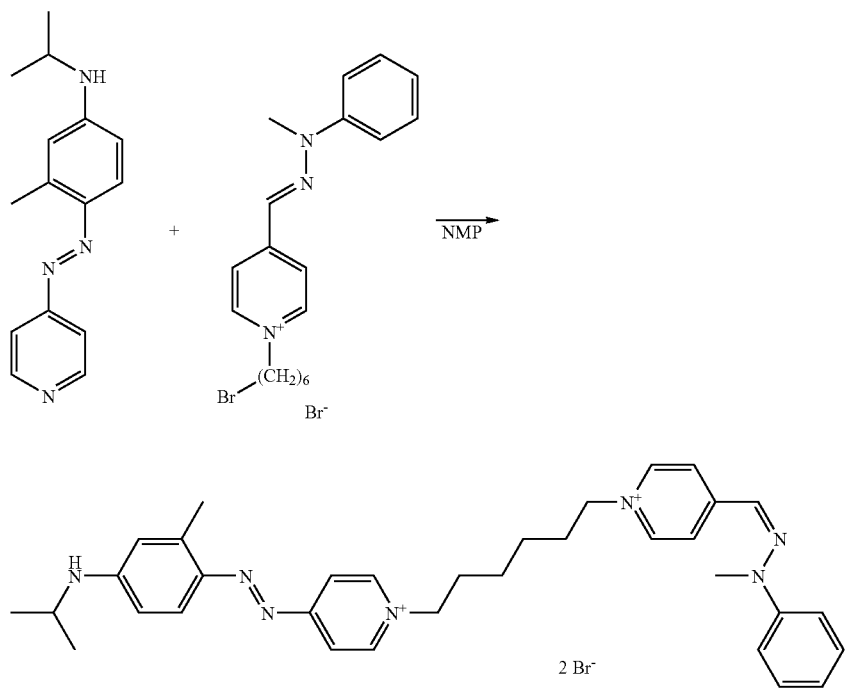
The product structure was confirmed by LC/MS analysis: molecular peak m/z=275; maximum absorption wavelength ($\lambda_{max}$): 426 nm; 562 nm; 256 nm.

EXAMPLE 22
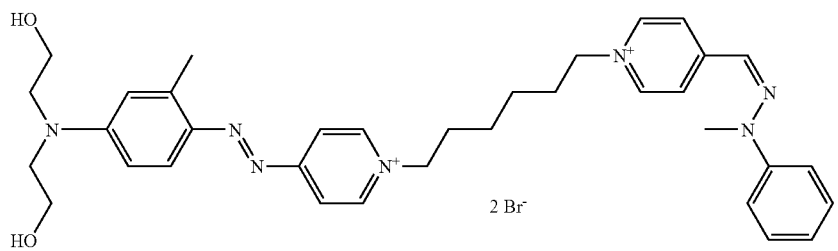
Reaction Scheme:
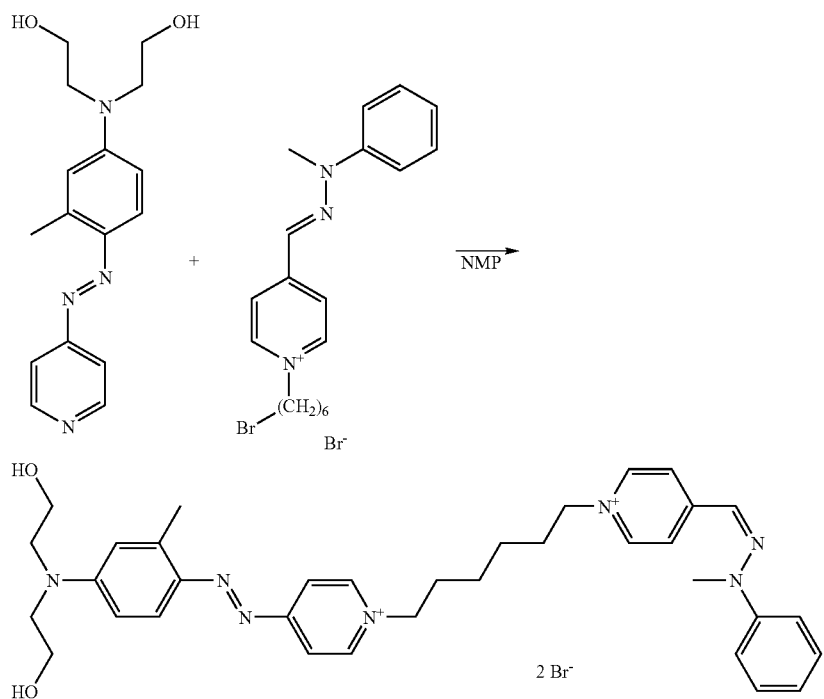
The product structure was confirmed by LC/MS analysis: molecular peak m/z=298; maximum absorption wavelength ($\lambda_{max}$): 424 nm; 572 nm; 256 nm.
EXAMPLE 23
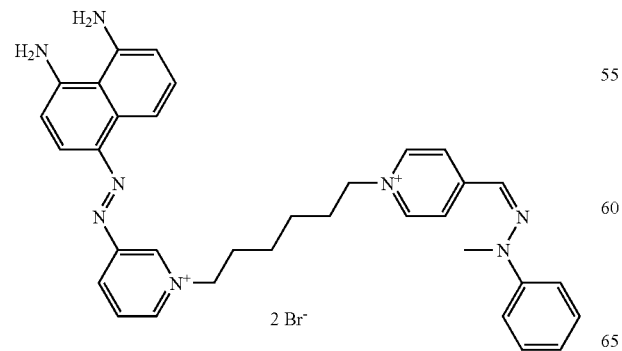

Reaction Scheme:

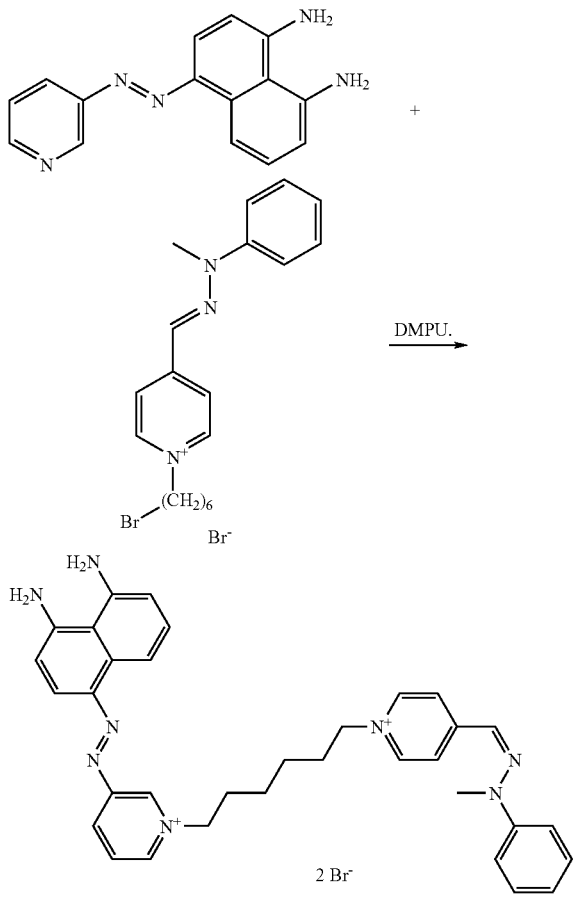

The product structure was confirmed by LC/MS analysis: molecular peak m/z=279; maximum absorption wavelength ($\lambda_{max}$): 424 nm; 572 nm.

Using dye compositions of the same kind as that described in Example 1, with each comprising the coloring agents obtained in Examples 12 to 23, allows for the procurement of colored locks of hair.

What is claimed is:

1. A dye composition comprising, in a medium suitable for dyeing keratin fibers, at least one mixed dye comprising at least two different chromophores, wherein at least one of the chromophores is chosen from the azo family and the tri(hetero)arylmethane family, wherein the chromophores are linked together via at least one linker that stops delocalization of the electrons of each of the chromophores, wherein the composition does not comprise mixed dyes whose chromophores are all of the azo family.

2. The composition according to claim 1, wherein the mixed dye comprises at least two different chromophores, at least one of which bears at least one cationic charge.

3. The composition according to claim 1, wherein the chromophores absorb in the visible range from 400 to 800 nm.

4. The composition according to claim 1, wherein the mixed dye comprises two to four chromophores.

5. The composition according to claim 2, wherein the cationic chromophore comprises at least one quaternized nitrogen atom.

6. The composition according to claim 1, wherein the chromophores of the azo family are chosen from compounds comprising at least one —N═N— sequence, the two nitrogen atoms of which are not simultaneously engaged in a ring; given that it is not excluded for one of the two nitrogen atoms of the —N═N— sequence to be engaged in a ring.

7. The composition according to claim 1, wherein the chromophores of the azo family are chosen from azo compounds of formula (I) below, and also the tautomeric forms thereof:

$$A_1\text{-}[N{=}N\text{-}(A_3)_y]_x\text{-}A_2 \qquad (I)$$

wherein:
  x is an integer ranging from 1 to 3;
  y is 0 or 1;
  $A_1$ and $A_2$, which may be identical or different, are each chosen from $C_6$-$C_{30}$ aromatic radicals and 5- to 30-membered heteroaromatic radicals, comprising at least one hetero atom chosen from nitrogen, oxygen and sulfur atoms; wherein at least one of the groups $A_1$ and $A_2$ is substituted;
  $A_1$ or $A_2$ is linked to the linker of the at least one mixed dye;
  $A_3$ is chosen from monoaromatic and polyaromatic $C_6$-$C_{30}$ divalent radicals, which are optionally substituted.

8. The composition according to claim 7, wherein $A_3$ is substituted with at least one entity, which may be identical or different, chosen from linear and branched $C_1$-$C_6$ alkyl radicals; linear and branched $C_1$-$C_6$ alkoxy radicals; a hydroxyl radical; an amino radical; an amino radical substituted with at least one alkyl radical chosen from linear and branched $C_1$-$C_6$ alkyl radicals, which may be identical or different, optionally bearing at least one hydroxyl radical; a nitro radical; halogen atoms; $C_1$-$C_{12}$ alkylsulfonamido (alkyl-SO$_2$—NH—); $C_1$-$C_{12}$ alkylsulfamoyl (alkyl-NH—SO$_2$—); acyloxy in which the alkyl portion is of $C_1$-$C_{12}$; an alkoxycarbonyl radical in which the alkyl portion is of $C_1$-$C_{12}$; and a carboxyl radical.

9. The composition according to claim 7, wherein the chromophores of the azo family are chosen from compounds of formula (I) with x=1 and y=0, and also the tautomeric forms thereof, wherein:
  $A_1$ is chosen from radicals of formulae (II) to (IV)

Formula (II)

Formula (III)

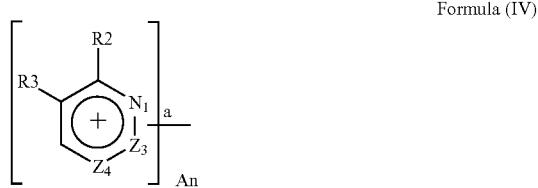

Formula (IV)

wherein:
  bond a is linked to the azo group either via the ring or via $N^1$, $N_1$, $Z_1$, $Z_2$, $Z_3$, $Z_4$, $R_1$, R $R_2$ or $R_3$;

$Z_1$ is chosen from oxygen and sulfur atoms, a radical $NR_4$ and a radical $CR_5$, $Z_2$ is chosen from a nitrogen atom and a radical $CR_6$, $Z_3$ is chosen from a nitrogen atom and a radical $CR_7$, $Z_4$ is chosen from a nitrogen atom and a radical $CR_8$, $R_1$ and $R_6$ may together form an aromatic ring, $R_7$ and $R_8$ may together form an aromatic ring, $R_1$, $R_2$, $R_3$, $R_5$, $R_6$, $R_7$, and $R_8$, which may be identical or different, are each chosen from a hydrogen atom; linear and branched, optionally substituted $C_1$-$C_8$ alkyl radicals; an optionally substituted 5- or 6-membered (hetero)aryl radical; halogen atoms; a hydroxyl group; linear and branched, optionally substituted $C_1$-$C_8$ alkoxy radicals; an amino radical; an amino radical substituted with at least one alkyl radical chosen from linear and branched $C_1$-$C_6$ alkyl radicals, which may be identical or different, optionally bearing at least one hydroxyl group; a nitro group; a cyano group; $C_1$-$C_{12}$ alkylsulfonamido (alkyl-$SO_2$—NH—); $C_1$-$C_{12}$ alkylsulfamoyl (alkyl-NH—$SO_2$—); acyloxy in which the alkyl portion is of $C_1$-$C_{12}$; alkoxycarbonyl in which the alkyl portion is of $C_1$-$C_{12}$; and a carboxyl group;

$R_4$ is chosen from linear and branched, optionally substituted $C_1$-$C_8$ alkyl radicals;

An is a cosmetically acceptable anion, and $A_2$ is an optionally substituted, optionally cationic group chosen from $C_6$-$C_{30}$ aromatic and 5- to 30-membered heteroaromatic groups, linked to the azo group either via the ring or via one of its substituents.

10. The composition according to claim 7, wherein $A_2$ is a carbon-based aromatic group or a pyridine group of formula (V):

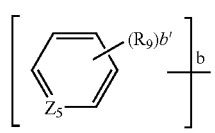

(V)

wherein:

bond b is linked to the azo group via the ring;

$Z_5$ is chosen from a nitrogen atom and a radical $CR_{10}$;

$R_9$ and $R_{10}$, which may be identical or different, are each chosen from a hydrogen atom; linear and branched, optionally substituted $C_1$-$C_8$ alkyl radicals; an optionally substituted 5- or 6-membered (hetero)aryl radical; halogen atoms; a hydroxyl group; linear and branched, optionally substituted $C_1$-$C_8$ alkoxy radicals; an amino radical; an amino radical substituted with at least one alkyl radical chosen from linear and branched $C_1$-$C_6$ alkyl radicals, which may be identical or different, optionally bearing at least one hydroxyl group; a nitro group; a cyano group; $C_1$-$C_{12}$ alkylsulfonamido (alkyl-$SO_2$—NH—); $C_1$-$C_{12}$ alkylsulfamoyl (alkyl-NH—$SO_2$—); acyloxy in which the alkyl portion is of $C_1$-$C_{12}$; alkoxycarbonyl in which the alkyl portion is of $C_1$-$C_{12}$; and a carboxyl group; and coefficient b' is equal to 4.

11. The composition according to claim 1, wherein the chromophores of the tri(hetero)arylmethane family are chosen from the compounds of formulae (VI) to (VIII) below:

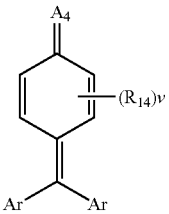

(VI)

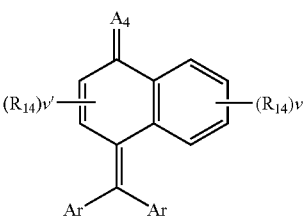

(VII)

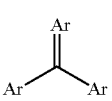

(VIII)

wherein:

Ar, which may be identical or different, is chosen from an optionally substituted aryl radical; and an optionally substituted heterocycle;

$A_4$ is chosen from O, N—$R_{15}$, and $N^+(R_{16})_2$ wherein $R_{15}$ and $R_{16}$, which may be identical or different, are each chosen from a hydrogen atom, linear and branched $C_1$-$C_8$ alkyl radicals, which are optionally substituted; an amido group (—$CONH_2$), a $C_1$-$C_4$ alkoxy group; an amino radical; an amino radical substituted with at least one alkyl radical chosen from linear and branched $C_1$-$C_4$ alkyl radicals, which may be identical or different, optionally bearing at least one hydroxyl group;

$R_{14}$, which may be identical or different, is chosen from a hydrogen atom; halogen atoms; a sulfonylamino group; a hydroxyl group; linear and branched, optionally substituted $C_1$-$C_8$ alkyl radicals; linear and branched, optionally substituted $C_1$-$C_8$ alkoxy radicals; linear and branched, optionally substituted $C_1$-$C_8$ alkylthio radicals; an amino radical; an amino radical substituted with at least one alkyl radical chosen from linear and branched $C_1$-$C_8$ alkyl radicals, which may be identical or different, optionally bearing at least one hydroxyl group; a heterocyclic radical; a nitro group; a cyano group; an optionally substituted aryl radical; an acyl group; linear and branched $C_1$-$C_8$ alkoxycarbonyl radicals; a carboxamido group; —$CO_2H$; —$SO_3H$; —$PO_3H_2$; and —$PO_4H_2$;

v is equal to 4; and v' is equal to 2.

12. The composition according to claim 1, wherein the chromophores are chosen from chromophores of the methine family, the carbonyl family, and the cyclic azine family, and chromophores of (hetero)aromatic nitro compounds.

13. The composition according to claim 12, wherein the chromophores of the methine family are chosen from compounds comprising at least one sequence chosen from >C=C< and —N=C<, the two atoms of which are not simultaneously engaged in a ring; given that it is not excluded for one of the nitrogen or carbon atoms of the sequences to be engaged in a ring.

14. The composition according to claim 12, wherein the chromophores of the methine family are chosen from radicals derived from chromophores of the families of methines, azomethines, mono- and diarylmethanes, indamines, indophenols, indoanilines, carbocyanins, azacarbocyanins and isomers thereof, diazacarbocyanins and isomers thereof, tetraazacarbocyanins and hemicyanins, and isomers thereof.

15. The composition according to claim 12, wherein the chromophores of the methine family are chosen from
(a) radicals derived from compounds of formula (IX) below, and also the tautomeric forms thereof:

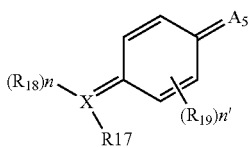

(IX)

wherein:
  $R_{17}$ and $R_{18}$, which may be identical or different, are each chosen from a hydrogen atom; a $C_6$-$C_{30}$ aryl radical, a ($C_1$-$C_8$)alkylaryl radical, wherein the aryl portion is optionally substituted; and heterocyclic radicals; provided that $R_{17}$ and $R_{18}$ are not simultaneously either an aromatic radical or a heteroaromatic radical;
  $R_{19}$, which may be identical or different, is chosen from a hydrogen atom; linear and branched, optionally substituted $C_1$-$C_8$ alkyl radicals; an optionally substituted $C_6$-$C_{30}$ aryl radical; an amino radical; an amino radical substituted with at least one radical chosen from linear and branched $C_1$-$C_4$ alkyl radicals, optionally bearing at least one hydroxyl group; a hydroxyl group; linear and branched $C_1$-$C_8$ alkoxy radicals, optionally bearing at least one hydroxyl group; a $C_1$-$C_4$ alkoxy group; and halogen atoms;
  X is chosen from a nitrogen atom and a carbon atom;
  coefficient n is 0 when X is a nitrogen atom, and is 1 when X is a carbon atom;
  coefficient n' is equal to 4;
  $A_5$ is chosen from an amino group; an amino group substituted with at least one alkyl radical chosen from linear and branched $C_1$-$C_8$ alkyl radicals, which may be identical or different, optionally bearing at least one hydroxyl group, an ammonium group $N^+(R_{20})_2$, wherein $R_{20}$, which may be identical or different, is chosen from an optionally substituted $C_1$-$C_8$ alkyl radical; and a $C_6$ aryl radical, which is optionally substituted; and
(b) radicals derived from compounds of formula (X) below:

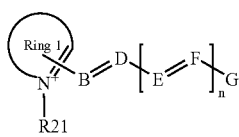

(X)

and, where appropriate, the tautomeric forms thereof;
wherein
  B, D, E and F, which may be identical or different, are each chosen from a nitrogen atom and a group C—$R_{22}$, wherein $R_{22}$, which may be identical or different, is chosen from a hydrogen atom, a $C_1$-$C_8$ alkyl radical which is optionally substituted; linear and branched $C_1$-$C_4$ alkoxy radicals; an amino radical; an amino radical substituted with at least one alkyl radical chosen from linear and branched $C_1$-$C_4$ alkyl radicals, which may be identical or different, optionally bearing at least one hydroxyl group; an optionally substituted $C_6$ aryl radical; and an optionally substituted 5- to 12-membered heteroaryl radical;
  n=0 or 1;
  G is chosen from a Ring 4 and the following residues:

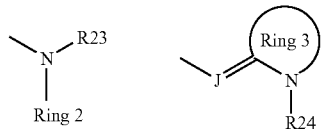

wherein:
  $R_{21}$ and $R_{24}$, which may be identical or different, are each chosen from linear and branched, optionally substituted $C_1$-$C_8$ alkyl radicals; and an optionally substituted benzyl radical;
  $R_{23}$ is chosen from a hydrogen atom, a $C_1$-$C_8$ alkyl radical which is optionally substituted, linear and branched $C_1$-$C_4$ alkoxy radicals, an amino radical, an amino radical substituted with at least one alkyl radical chosen from linear and branched $C_1$-$C_4$ alkyl radicals, which may be identical or different, optionally bearing at least one hydroxyl group; an optionally substituted $C_6$ aryl radical; and an optionally substituted $C_2$-$C_{12}$ heteroaryl radical;
  J is chosen from a nitrogen atom and a group C—$R_{25}$; wherein $R_{25}$ is chosen from a hydrogen atom, a $C_1$-$C_8$ alkyl radical which is optionally substituted; linear and branched $C_1$-$C_4$ alkoxy radicals; an amino radical; an amino radical substituted with at least one alkyl radical chosen from linear and branched $C_1$-$C_4$ alkyl radicals, which may be identical or different, optionally bearing at least one hydroxyl group; an optionally substituted $C_6$ aryl radical; and an optionally substituted 5- to 12-membered heteroaryl radical;
  Ring 1 is chosen from 5- to 12-membered heteroaromatic radicals, bearing at least one cationic charge on a nitrogen atom and optionally comprising at least one other hetero atom chosen from nitrogen, oxygen and sulfur atoms; wherein the 5- to 12-membered heteroaromatic radicals are optionally substituted with at least one entity chosen from linear and branched, substituted and unsubstituted $C_1$-$C_8$ alkyl radicals; linear and branched, substituted and unsubstituted $C_1$-$C_8$ alkoxy radicals; an amino radical; an amino radical substituted with at least one alkyl group chosen from linear and branched $C_1$-$C_8$ alkyl groups, which may be identical or different, optionally bearing at least one hydroxyl group; a $C_5$-$C_6$ aromatic radical; a hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);
  Ring 2 is chosen from $C_6$-$C_{12}$ aromatic radicals and 5- to 12-membered heteroaromatic radicals, comprising at least one hetero atom chosen from nitrogen, oxygen and sulfur atoms; wherein the $C_6$-$C_{12}$ aromatic radicals and the 5- to 12-membered heteroaromatic radicals are optionally substituted with at least one entity chosen from linear and branched $C_1$-$C_8$ alkyl radical; linear and branched $C_1$-$C_8$ alkoxy radical; an amino radical; an amino radical substituted with at least one alkyl group chosen from linear and branched $C_1$-$C_8$ alkyl groups, which may be identical or different, optionally bearing at least one hydroxyl group; a (hetero)aromatic radical; and a hydroxyl group;

Ring 3 is chosen from 5- and 6-membered heteroaromatic radicals comprising at least one hetero atom chosen from nitrogen, oxygen and sulfur atoms; wherein the 5- and 6-membered heteroaromatic radicals are optionally substituted with at least one entity chosen from linear and branched $C_1$-$C_8$ alkyl radicals; linear and branched $C_1$-$C_8$ alkoxy radicals; an amino radical; an amino radical substituted with at least one alkyl group chosen from linear and branched $C_1$-$C_8$ alkyl groups, which may be identical or different, optionally bearing at least one hydroxyl group; a $C_5$-$C_6$ aromatic radical; a hydroxyl group; an alkoxycarbonyl group; a nitro group; a cyano group; a $C_1$-$C_{12}$ alkylsulfonamido group (alkyl-$SO_2$—NH—); and a $C_1$-$C_{12}$ alkylsulfamoyl group (alkyl-NH—$SO_2$—);

Ring 4 is chosen from $C_6$-$C_{12}$ aromatic radicals and 5- to 12-membered heteroaromatic radicals, comprising at least one hetero atom chosen from nitrogen, oxygen and sulfur atoms; wherein the $C_6$-$C_{12}$ aromatic radicals and the 5- to 12-membered heteroaromatic radicals are optionally substituted with at least one entity chosen from linear and branched $C_1$-$C_8$ alkyl radicals; linear and branched $C_1$-$C_8$ alkoxy radicals; an amino radical; an amino radical substituted with at least one alkyl group chosen from linear and branched $C_1$-$C_8$ alkyl groups, which may be identical or different, optionally bearing at least one hydroxyl group; a (hetero)aromatic radical; and a hydroxyl group;

provided that when n is 1 and G is a ring, then B, D, E and F are not simultaneously a nitrogen atom; and that when n is 0 and G is a ring, then B and D are not simultaneously a nitrogen atom.

16. The composition according to claim 15, wherein, in defining $R_{17}$ and $R_{18}$, the aryl portion of the ($C_1$-$C_8$)alkylaryl radical is optionally substituted with at least one entity chosen from a hydroxyl group, linear and branched, substituted and unsubstituted $C_1$-$C_4$ alkoxy groups, an amino group, an amino group substituted with at least one alkyl radical chosen from linear and branched $C_1$-$C_4$ alkyl radicals, which may be identical or different, optionally bearing at least one hydroxyl group, and halogen atoms.

17. The composition according to claim 15, wherein, in defining $R_{17}$ and $R_{18}$, the heterocyclic radicals are chosen from thiophene, furan, piperonyl, indole, indoline, pyridine, carbazole, dehydroquinoline and chromone heterocycles.

18. The composition according to claim 15, wherein, in defining $R_{20}$, the $C_6$ aryl radical is optionally substituted with at least one entity chosen from a hydroxyl group, halogen atoms, a nitro group, a cyano group, linear and branched $C_1$-$C_4$ alkoxy groups, linear and branched $C_1$-$C_4$ monohydroxyalkoxy groups, linear and branched $C_2$-$C_4$ polyhydroxyalkoxy groups, an amino group, which is unsubstituted or substituted with at least one radical chosen from linear and branched $C_1$-$C_4$ alkyl and hydroxyalkyl radicals.

19. The composition according to claim 12, wherein the chromophores of the carbonyl family are chosen from radicals derived from dyes of families of acridones, benzoquinones, anthraquinones, naphthoquinones, benzanthrones, anthranthrones, pyranthrones, pyrazolanthrones, pyrimidinoanthrones, flavanthrones, idanthrones, flavones, (iso)violanthrones, isoindolinones, benzimidazolones, isoquinolinones, anthra-pyridones, pyrazoloquinazolones, perinones, quinacridones, quinophthalones, indigoids, thioindigos, naphthalimides, anthrapyrimidines, diketopyrrolopyrroles and coumarins.

20. The composition according to claim 12, wherein the chromophores of the carbonyl family are chosen from radicals derived from dyes of formula (XI) below:

(XI)

wherein the ring is a 5- or 6-membered ring, at least one of the ring members of which is optionally replaced with a hetero atom chosen from oxygen, nitrogen and sulfur atoms, or with an additional carbonyl functional group; wherein the ring is optionally substituted with at least one entity chosen from optionally substituted linear and branched $C_1$-$C_8$ alkyl radicals; a hydroxyl radical; halogen atoms; nitro, cyano, amino and alkylamino groups, wherein the ring is optionally fused with at least one $C_6$ aromatic ring, wherein the ring or the at least one $C_6$ aromatic ring is possibly fused with at least one aromatic ring, at least one of the carbon atoms of which is optionally replaced with at least one hetero atom chosen from oxygen, nitrogen and sulfur atoms.

21. The composition according to claim 12, wherein the chromophores of the cyclic azine family are chosen from radicals derived from dyes of families of azine, xanthene, thioxanthene, fluorindine, acridine, (di)oxazine, (di)thiazine and pyronine.

22. The composition according to claim 12, wherein the chromophores of the cyclic azine family are chosen from radicals derived from dyes of formula (XII) below, and also the tautomeric forms thereof:

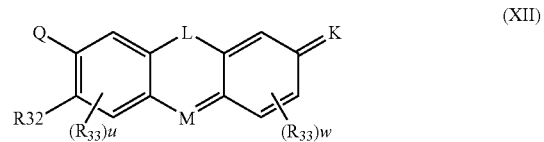

(XII)

wherein:
L is chosen from a hetero atom; an NH group; and a group N—$R_{34}$;
M is chosen from a hetero atom; a group $N^+$—$R_{34}$; a CH group; and a group C—$R_{35}$;
Q and K, which may be identical or different, are each chosen from a hydroxyl group; an amino radical; an amino radical substituted with at least one alkyl radical chosen from linear and branched $C_1$-$C_8$ alkyl radicals, which may be identical or different, optionally bearing at least one hydroxyl group; an optionally substituted aryl radical; an optionally substituted ($C_1$-$C_8$)alkylaryl radical; an ammonium group of $N^+(R_{36})_t$ wherein t equals to 2 for K and to 3 for Q, and $R_{36}$, which may be identical or different, is chosen from a hydrogen atom; linear and branched $C_1$-$C_8$ alkyl radicals, optionally bearing at least one hydroxyl group; an optionally substituted aryl radical; a ($C_1$-$C_8$)alkylaryl radical, wherein the aryl portion is optionally substituted; an optionally substituted linear or branched $C_1$-$C_8$ alkyl radical; and an optionally substituted linear or branched $C_1$-$C_8$ alkoxy radical;
provided that Q and K are not simultaneously an ammonium group of $N^+(R_{36})_t$;

$R_{32}$ and $R_{33}$, which may be identical or different, are each chosen from a hydrogen atom; an optionally substituted linear or branched $C_1$-$C_8$ alkyl radical; an amino radical; an amino radical optionally substituted with one or more radicals, which may be identical or different, chosen from linear and branched, optionally substituted $C_1$-$C_8$ alkyl radicals, optionally substituted phenyl radicals; and halogen atoms;

in the case where Q is a substituted or unsubstituted amino radical, or a hydroxyl group, $R_{32}$ may be chosen from alkylamino and alkoxy radicals forming, with the hetero atom of the radical M, a 6-membered ring, optionally fused with an aromatic radical, wherein the aromatic radical is optionally substituted with at least one amino group or an amino group that is optionally substituted with one or more radicals, which may be identical or different, chosen from optionally substituted linear and branched $C_1$-$C_8$ alkyl radicals and optionally substituted phenyl radicals;

$R_{34}$ and $R_{35}$, which may be identical or different, are each chosen from linear and branched $C_1$-$C_8$ alkyl radicals, which are optionally substituted; and aryl radicals, which are optionally substituted;

coefficient u ranges from 0 to 2; and coefficient w ranges from 0 to 3.

23. The composition according to claim 22, wherein, in defining $R_{34}$ and $R_{35}$, the linear and branched $C_1$-$C_8$ alkyl radicals are optionally substituted with at least one entity chosen from a hydroxyl group, linear and branched $C_1$-$C_8$ alkoxy radicals, an amino radical, an amino radical substituted with at least one alkyl radical chosen from linear and branched $C_1$-$C_8$ alkyl radicals, which may be identical or different, optionally bearing at least one hydroxyl radical.

24. The composition according to claim 22, wherein, in defining $R_{34}$ and $R_{35}$, the aryl radicals are optionally substituted with at least one entity chosen from linear and branched $C_1$-$C_8$ alkyl radicals; a hydroxyl group; linear and branched $C_1$-$C_8$ alkoxy radicals; an amino radical; an amino radical substituted with at least one alkyl radical chosen from linear and branched $C_1$-$C_8$ alkyl radicals, which may be identical or different, optionally bearing at least one hydroxyl group; halogen atoms; a nitro group; and a cyano group.

25. The composition according to claim 12, wherein the chromophore of the family of (hetero)aromatic nitro compounds are chosen from compounds of formulae (XIII) and (XIV) below, and also the tautomeric forms thereof:

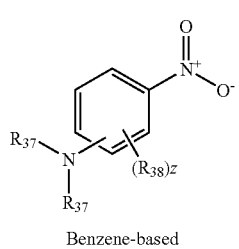

Benzene-based (XIII)

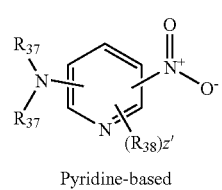

Pyridine-based (XIV)

wherein $R_{37}$, which may be identical or different, is chosen from a hydrogen atom; linear and branched $C_1$-$C_8$ alkyl radicals, optionally bearing at least one hydroxyl group; an optionally substituted aryl radical, a ($C_1$-$C_8$) alkylaryl radical, wherein the aryl portion is optionally substituted; linear and branched, optionally substituted $C_1$-$C_8$ alkyl radicals, and linear and branched, optionally substituted $C_1$-$C_8$ alkoxy radicals;

$R_{38}$, which may be identical or different, is chosen from a hydrogen atom; linear and branched, optionally substituted $C_1$-$C_4$ alkyl radicals; linear and branched, optionally substituted $C_1$-$C_8$ alkoxy radicals; an optionally substituted $C_6$ aryl radical; an amino radical; an amino radical substituted with at least one radical chosen from linear and branched $C_1$-$C_8$ alkyl radicals, which may be identical or different, which are optionally substituted, linear and branched $C_1$-$C_4$ alkoxy groups, linear and branched $C_1$-$C_4$ thioalkyl groups, and linear and branched $C_1$-$C_4$ alkylsulfonamido groups; optionally substituted $C_6$ aryl radicals, optionally substituted 5- to 6-membered heteroaryl radicals; a hydroxyl group; a nitro group; and a cyano group;

coefficient z is equal to 4; and coefficient z' is equal to 3.

26. The composition according to claim 1, wherein the at least one linker is cationic or non-cationic.

27. The composition according to claim 1, wherein the at least one linker is chosen from divalent, trivalent and tetravalent groups.

28. The composition according to claim 27, wherein the at least one linker is chosen from an arylene radical; a divalent terephthalamide radical; a divalent or trivalent radical, and linear and branched $C_1$-$C_{20}$ hydrocarbon-based chains, wherein at least one of the carbon atoms of the chains is possibly replaced with a hetero atom, or with a saturated or unsaturated $C_5$-$C_6$ heterocycle, and wherein the hydrocarbon-based chains are possibly unsaturated or comprise at least one arylene radical.

29. The composition according to claim 1, wherein the at least one mixed dye is present in an amount ranging from 0.001% to 20% by weight relative to the total weight of the composition.

30. The composition according to claim 1, comprising at least one additional direct dye other than the at least one mixed dye.

31. The composition according to claim 30, wherein the at least one additional direct dye is present in an amount ranging from 0.001% to 10% by weight relative to the total weight of the dye composition.

32. The composition according to claim 1, further comprising at least one oxidation base chosen from para-phenylenediamines, bis(phenyl)alkylenediamines, para-aminophenols, ortho-aminophenols and heterocyclic bases, and the addition salts thereof.

33. The composition according to claim 1, further comprising at least one coupler chosen from meta-phenylenediamines, meta-aminophenols, meta-diphenols, naphthalene-based couplers and heterocyclic couplers, and the addition salts thereof.

34. The composition according to claim 32, wherein the at least one oxidation base is present in an amount ranging from 0.001% to 10% by weight relative to the total weight of the dye composition.

35. The composition according to claim 33, wherein the at least one coupler is present in an amount ranging from 0.001% to 10% by weight relative to the total weight of the dye composition.

36. The composition according to claim 1, further comprising at least one oxidizing agent.

37. The composition according to claim 36, wherein the at least one oxidizing agent is chosen from hydrogen peroxide, alkali metal peroxides, alkaline-earth metal peroxides, urea peroxide, alkali metal bromates, alkali metal ferricyanides, persalts, and enzymes.

38. The composition according to claim 1, wherein the composition has a pH ranging from 8 to 11.

39. A process for dyeing keratin fibers, comprising:
 a) applying to wet or dry fibers a dye composition comprising, in a medium suitable for dyeing keratin fibers, optionally in the presence of at least one oxidizing agent, at least one mixed dye comprising at least two different chromophores, wherein at least one of the chromophores is chosen from chromophores of the azo family and chromophores of the tri(hetero)arylmethane family, wherein the chromophores are linked together via at least one linker that stops delocalization of the electrons of each of the chromophores,
 wherein the composition does not comprise mixed dyes whose chromophores are all of the azo family,
 b) leaving the composition to act for a time sufficient to obtain a desired coloration,
 c) optionally rinsing the fibers,
 d) washing and rinsing the fibers, and
 e) drying the fibers or leaving the fibers to dry.

40. A multi-compartment device, comprising
 at least one first compartment comprising a dye composition comprising, in a medium suitable for dyeing keratin fibers,
 at least one mixed dye comprising at least two different chromophores, wherein at least one of the chromophores is chosen from chromophores of the azo family and chromophores of the tri(hetero)arylmethane family, wherein the chromophores are linked together via at least one linker that stops delocalization of the electrons of each of the chromophores,
 wherein the composition does not comprise mixed dyes whose chromophores are all of the azo family;
 optionally at least one additional direct dye different from the at least one mixed dye;
 optionally at least one oxidation base; and
 optionally at least one coupler; and
 at least one second compartment comprising at least one oxidizing agent.

41. A mixed dye, comprising at least two different chromophores, wherein at least one of the chromophores is chosen from chromophores of azo the family and chromophores of the tri(hetero)arylmethane family, wherein the chromophores are linked together via at least one linker that stops delocalization of the electrons of each of the chromophores, with the exception of the following compounds:

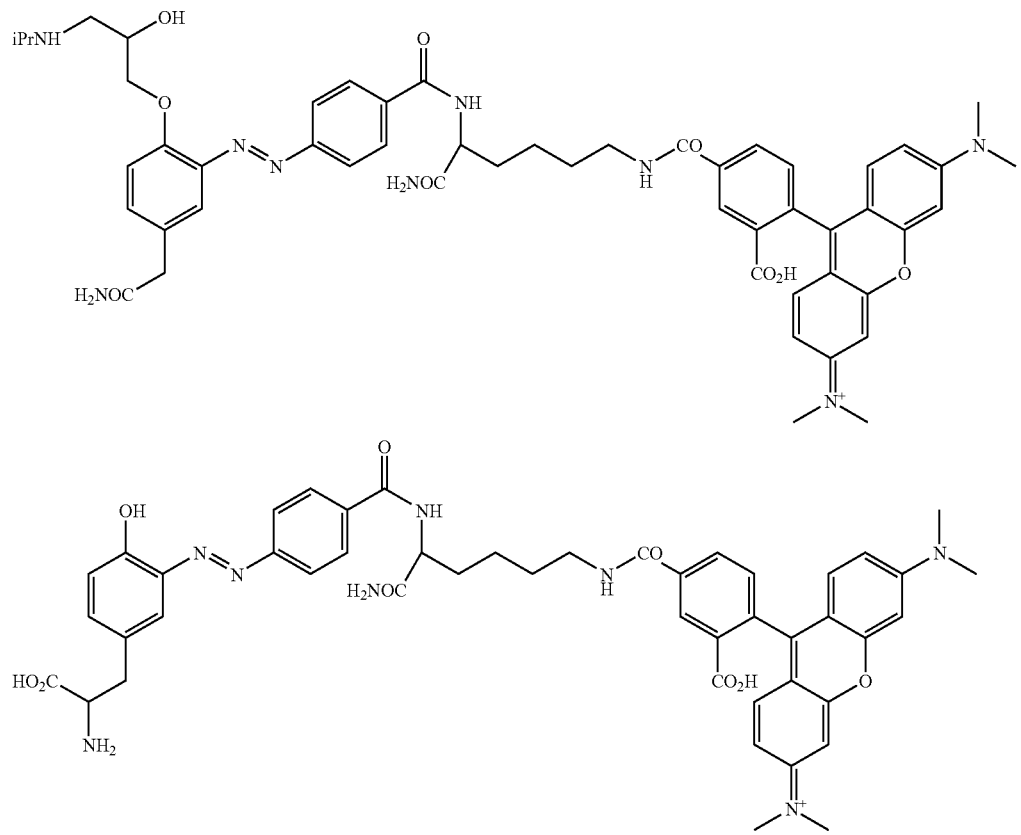

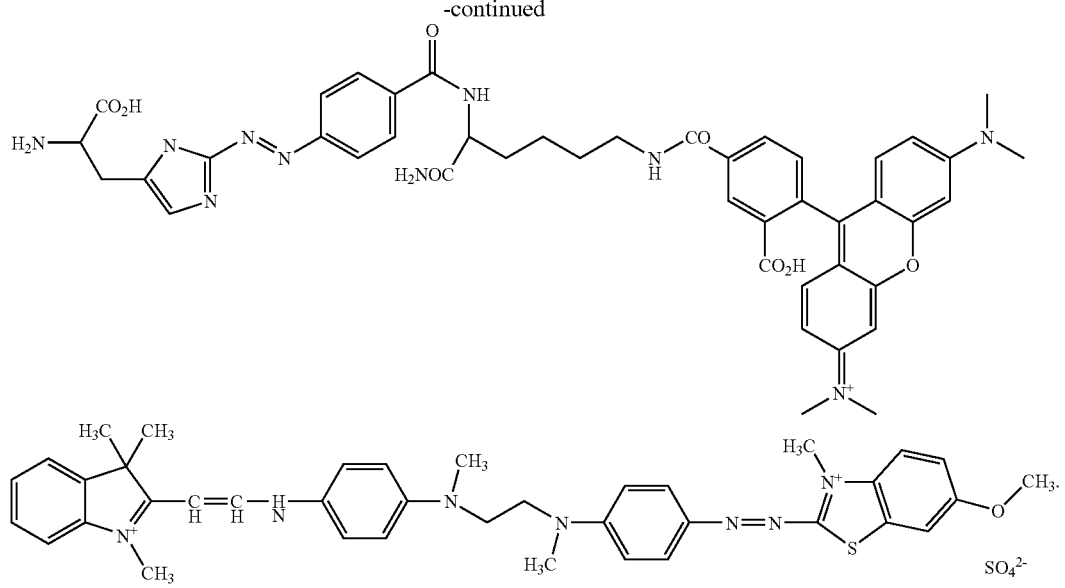
42. The mixed dye according to claim 41, wherein the mixed dye is chosen from compounds of the following formulae, and the addition salts thereof:
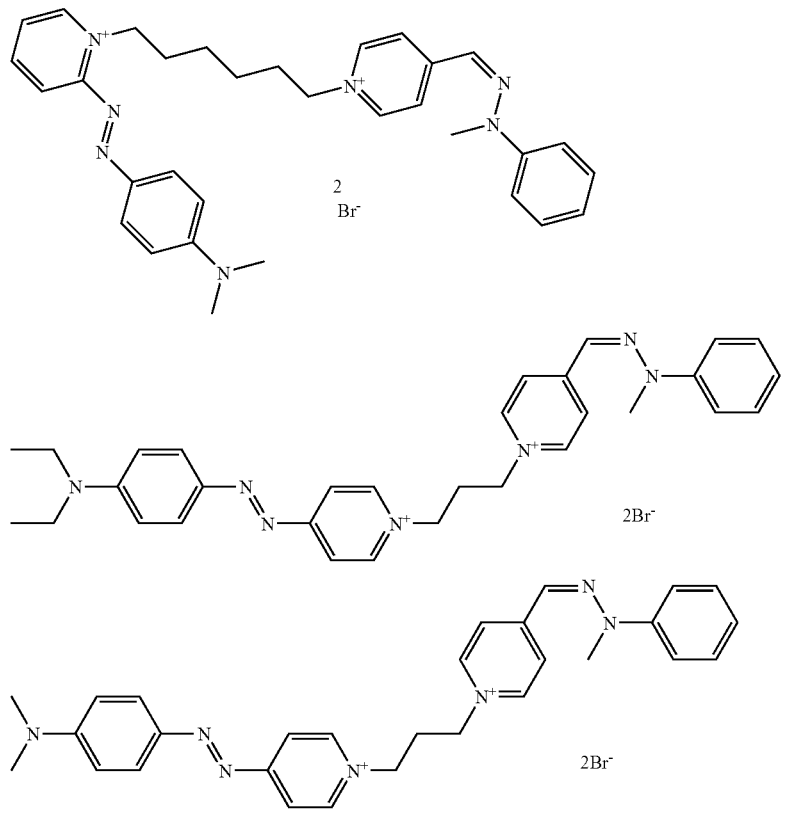

-continued
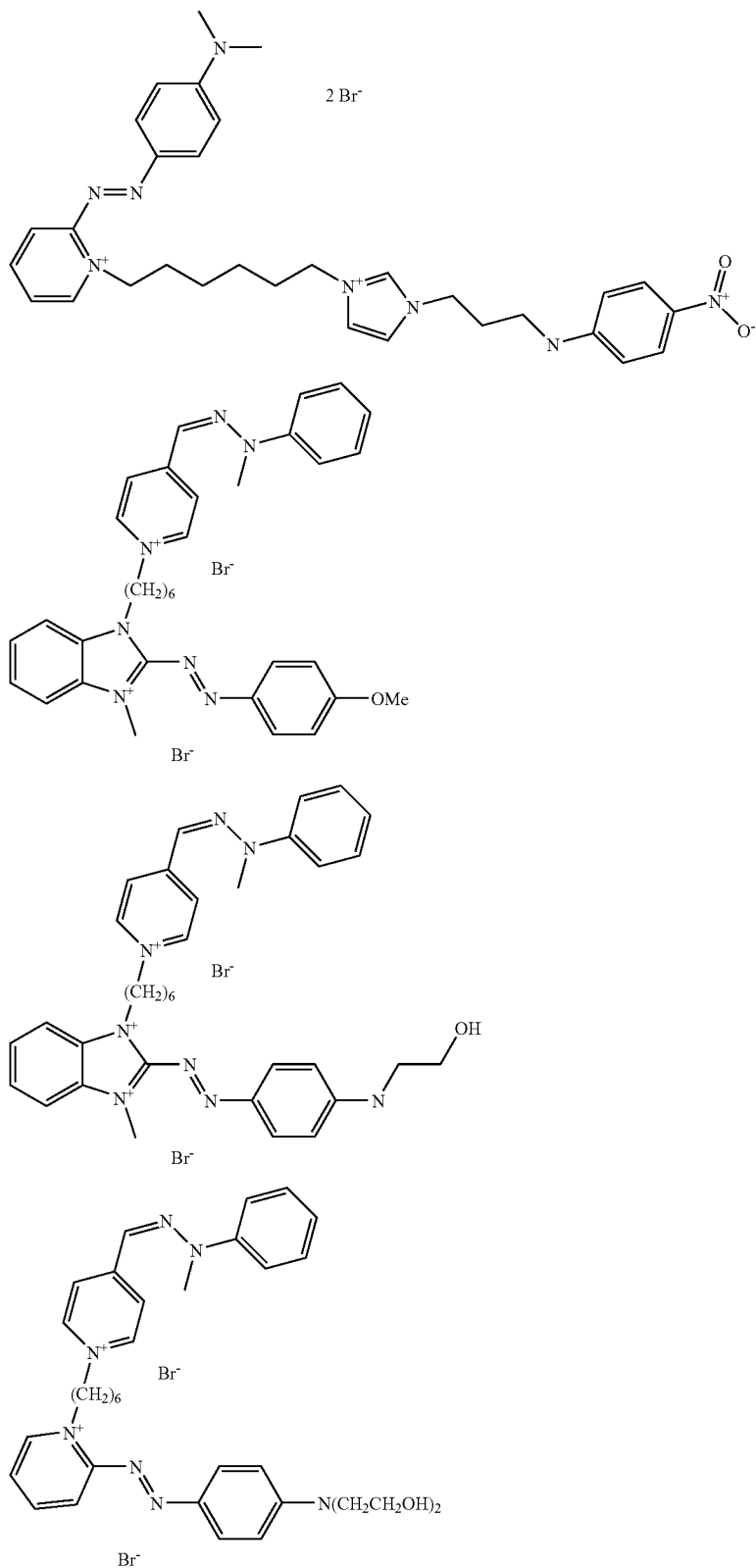

-continued
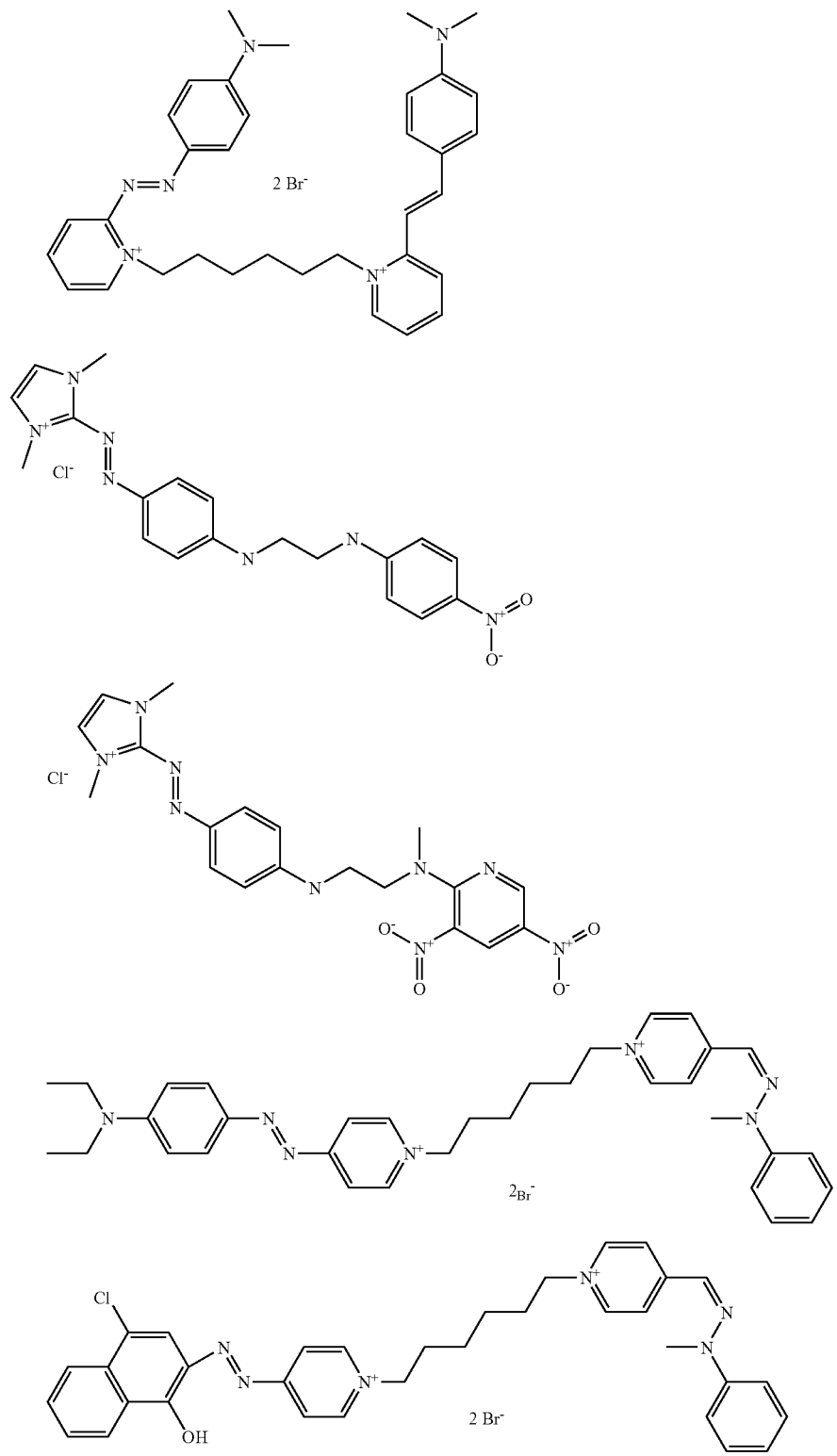

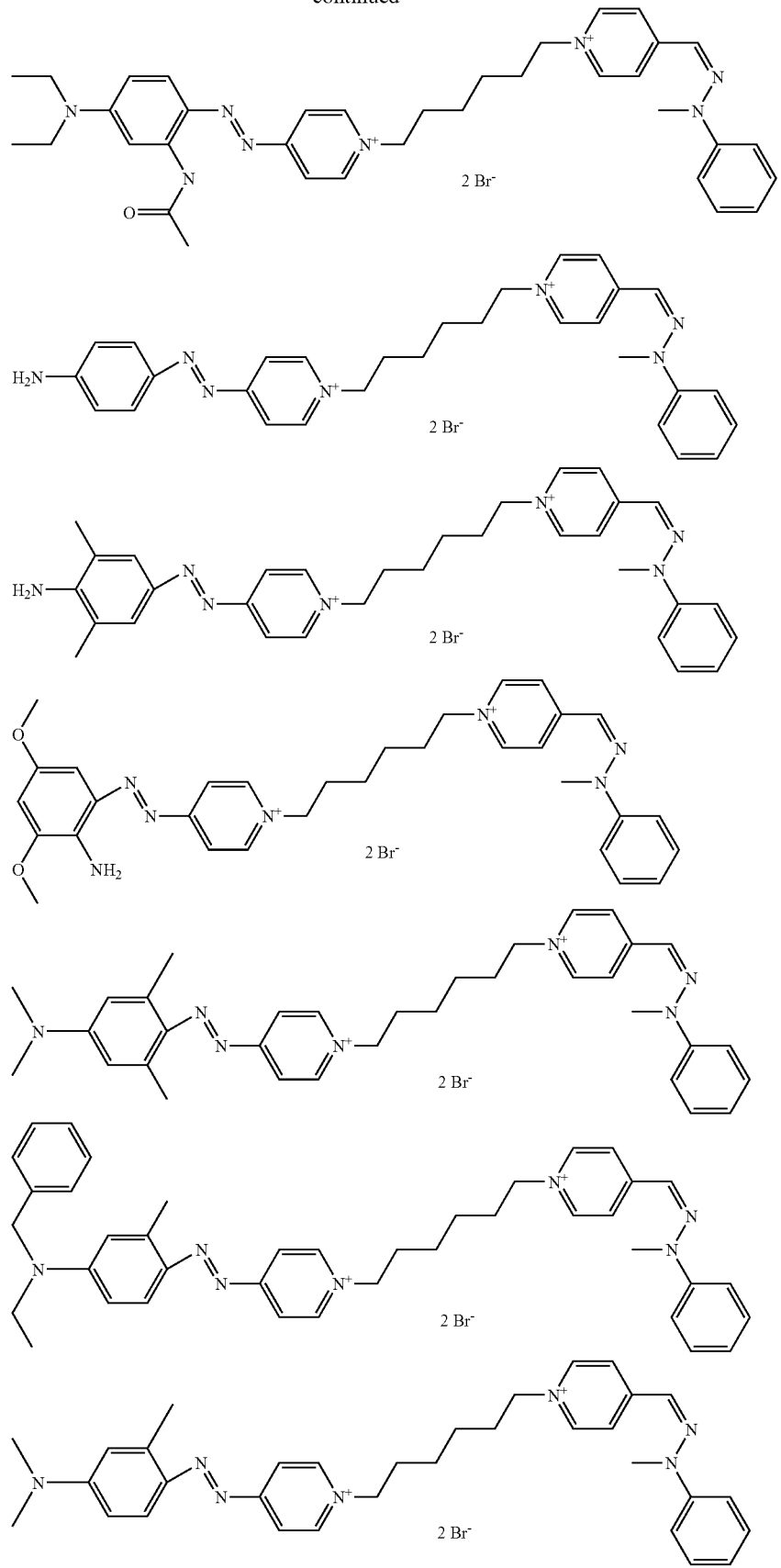

-continued
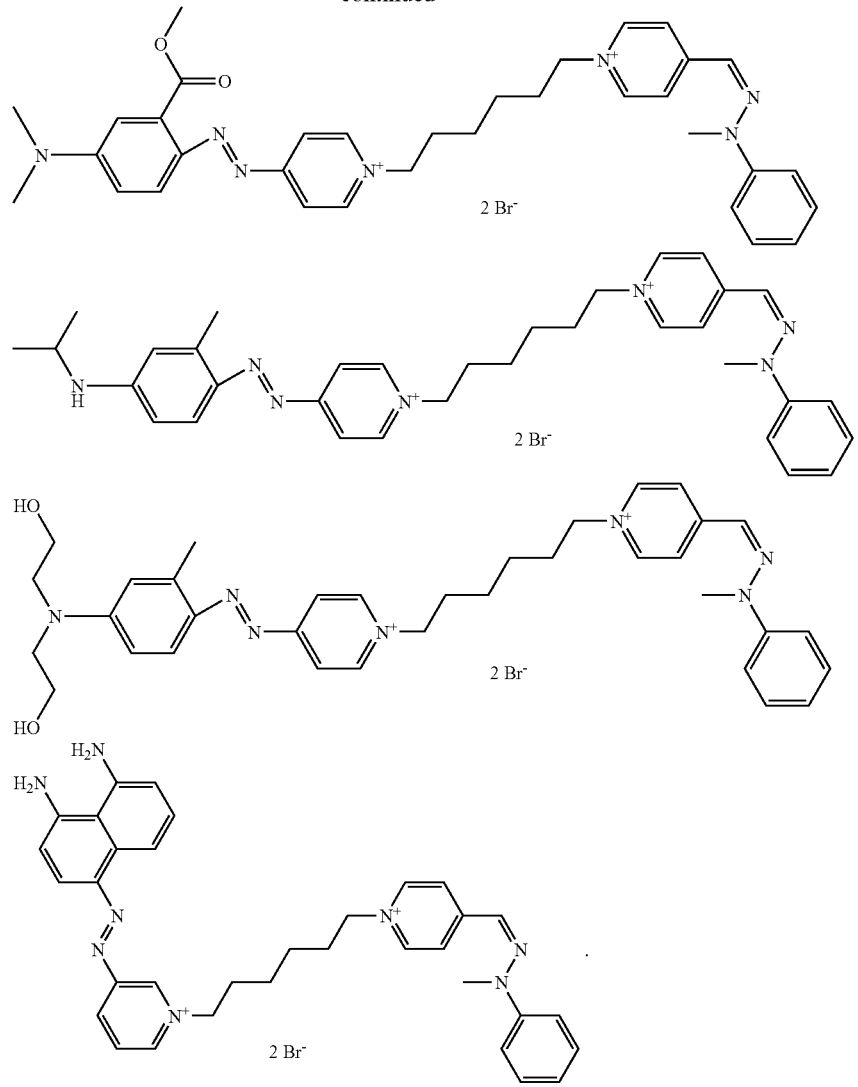

UNITED STATES PATENT AND TRADEMARK OFFICE
CERTIFICATE OF CORRECTION

PATENT NO. : 7,300,471 B2
APPLICATION NO. : 11/066459
DATED : November 27, 2007
INVENTOR(S) : Andrew Greaves et al.

It is certified that error appears in the above-identified patent and that said Letters Patent is hereby corrected as shown below:

Title Page, Item (54), line 3, "TRI(HETERO) ARYLMETHANE" should read --TRI(HETERO)ARYLMETHANE--.

Title Page, Item (54), line 5, "DYES." should read --DYES--.

Claim 9, col. 74, line 67, "$R_1$, R $R_2$" should read --$R_1$, $R_2$--.

Claim 19, col. 79, line 67, "anthra-pyridones," should read --anthrapyridones,--.

Claim 41, col. 84, line 22, "of azo the" should read --of the azo--.

Claim 41, cols. 85-86, lines 17-23,

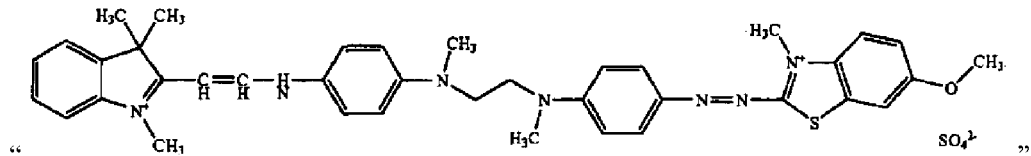

should read

UNITED STATES PATENT AND TRADEMARK OFFICE
CERTIFICATE OF CORRECTION

PATENT NO. : 7,300,471 B2  Page 2 of 2
APPLICATION NO. : 11/066459
DATED : November 27, 2007
INVENTOR(S) : Andrew Greaves et al.

It is certified that error appears in the above-identified patent and that said Letters Patent is hereby corrected as shown below:

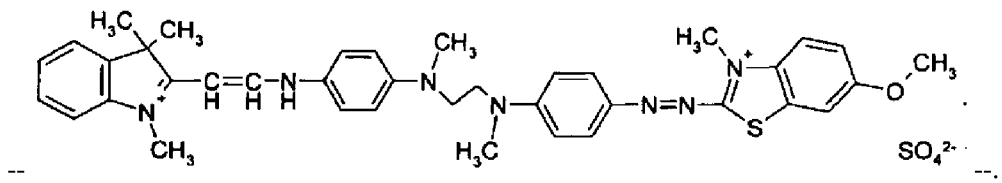

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,300,471 B2
APPLICATION NO. : 11/066459
DATED : November 27, 2007
INVENTOR(S) : Andrew Greaves et al.

It is certified that error appears in the above-identified patent and that said Letters Patent is hereby corrected as shown below:

Title Page, Item (54), line 4, and in Column 1, in the title, "TRI(HETERO) ARYLMETHANE" should read --TRI(HETERO)ARYLMETHANE--.

Title Page, Item (54), line 5, and in Column 1, in the title, "DYES." should read --DYES--.

Claim 9, col. 74, line 67, "$R_1$, R $R_2$" should read --$R_1$, $R_2$--.

Claim 19, col. 79, line 67, "anthra-pyridones," should read --anthrapyridones,--.

Claim 41, col. 84, line 22, "of azo the" should read --of the azo--.

Claim 41, cols. 85-86, lines 17-23,

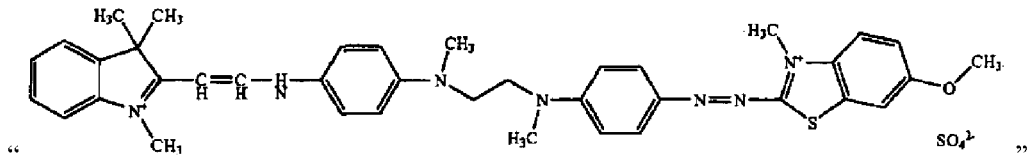

should read

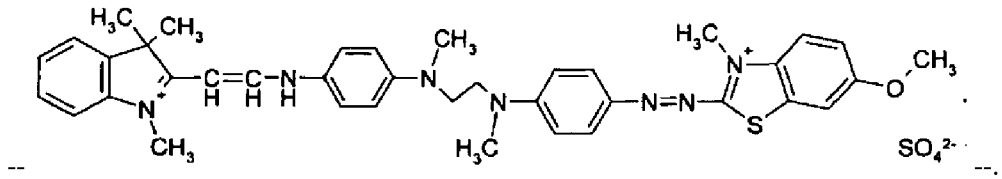

--.

This certificate supersedes the Certificate of Correction issued December 8, 2009.

Signed and Sealed this

Twenty-sixth Day of January, 2010

David J. Kappos
*Director of the United States Patent and Trademark Office*